(12) United States Patent
Manoharan et al.

(10) Patent No.: US 8,063,198 B2
(45) Date of Patent: Nov. 22, 2011

(54) PROCESSES AND REAGENTS FOR DESILYLATION OF OLIGONUCLEOTIDES

(75) Inventors: Muthiah Manoharan, Weston, MA (US); Michael E. Jung, Los Angeles, CA (US); Kallanthottathil G. Rajeev, Wayland, MA (US); Rajendra K. Pandey, South Grafton, MA (US); Gang Wang, Piscattaway, NJ (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 393 days.

(21) Appl. No.: 12/050,633

(22) Filed: Mar. 18, 2008

(65) Prior Publication Data
US 2009/0005549 A1   Jan. 1, 2009

Related U.S. Application Data

(63) Continuation of application No. 11/099,430, filed on Apr. 5, 2005, now abandoned.

(60) Provisional application No. 60/559,782, filed on Apr. 5, 2004.

(51) Int. Cl.
*C07H 21/00* (2006.01)
*C07C 17/07* (2006.01)

(52) U.S. Cl. .................................. 536/25.31; 570/123
(58) Field of Classification Search ............. 536/25.31; 570/123
See application file for complete search history.

(56) References Cited

U.S. PATENT DOCUMENTS

| | | | |
|---|---|---|---|
| 3,276,950 A | 10/1966 | Engelhard et al. | |
| 3,520,897 A | 7/1970 | Clapp et al. | |
| 3,621,030 A | 11/1971 | Seltzer | |
| 3,732,239 A | 5/1973 | Spatz et al. | |
| 3,740,396 A | 6/1973 | Haugwitz et al. | |
| 3,753,908 A | 8/1973 | de Vries et al. | |
| 3,956,303 A | 5/1976 | Bullock et al. | |
| 4,240,822 A | 12/1980 | Diehl et al. | |
| 4,474,948 A | 10/1984 | Hudson et al. | |
| 5,677,124 A | 10/1997 | DuBois et al. | |
| 5,750,672 A * | 5/1998 | Kempe .................. 536/25.31 | |
| 5,919,625 A | 7/1999 | DuBois et al. | |
| 5,939,262 A | 8/1999 | Pasloske et al. | |
| 6,057,134 A | 5/2000 | Lader et al. | |
| 6,096,881 A | 8/2000 | Han et al. | |
| 6,232,103 B1 | 5/2001 | Short | |
| 6,399,334 B1 | 6/2002 | Li et al. | |
| 6,593,464 B1 | 7/2003 | Gebeyehu et al. | |
| 6,610,490 B2 | 8/2003 | Schuster et al. | |
| 6,620,926 B2 | 9/2003 | Sproat | |
| 6,623,962 B1 | 9/2003 | Akhtar et al. | |
| 6,649,751 B2 | 11/2003 | Usman et al. | |
| 6,673,611 B2 | 1/2004 | Thompson et al. | |
| 6,673,918 B2 | 1/2004 | Bellon et al. | |
| 6,686,463 B2 | 2/2004 | Beigelman et al. | |
| 6,797,815 B2 | 9/2004 | Matulic-Adamic et al. | |
| 6,815,205 B2 | 11/2004 | Lin et al. | |
| 6,818,447 B1 | 11/2004 | Pavco et al. | |
| 6,818,759 B2 | 11/2004 | Beigelman et al. | |
| 6,830,902 B1 | 12/2004 | Astatke et al. | |
| 6,849,726 B2 | 2/2005 | Usman et al. | |
| 6,933,121 B2 | 8/2005 | Schuster et al. | |
| 6,972,330 B2 | 12/2005 | Beigelman et al. | |
| 6,977,295 B2 | 12/2005 | Belotserkovskii et al. | |
| 7,655,790 B2 | 2/2010 | Vargeese et al. | |
| 2002/0025526 A1 | 2/2002 | Schuster et al. | |
| 2002/0034750 A1 | 3/2002 | Short | |
| 2002/0086356 A1 | 7/2002 | Tuschl et al. | |
| 2002/0120129 A1* | 8/2002 | Beigelman et al. ......... 536/27.3 | |
| 2002/0132346 A1 | 9/2002 | Cibelli | |
| 2002/0143166 A1 | 10/2002 | Pires et al. | |

(Continued)

FOREIGN PATENT DOCUMENTS

DE   2228364 A1   12/1973

(Continued)

OTHER PUBLICATIONS

Fang et al. Nucleic Acids Research, 2003, 31(2), p. 708-715.*

(Continued)

*Primary Examiner* — Shaojia Anna Jiang
*Assistant Examiner* — Jonathan S Lau
(74) *Attorney, Agent, or Firm* — Jeffrey N. Townes; LeClairRyan

(57) ABSTRACT

The present invention relates to processes and reagents for oligonucleotide synthesis and purification. One aspect of the present invention relates to compounds useful for activating phosphoramidites in oligonucleotide synthesis. Another aspect of the present invention relates to a method of preparing oligonucleotides via the phosphoramidite method using an activator of the invention. Another aspect of the present invention relates to sulfur-transfer agents. In a preferred embodiment, the sulfur-transfer agent is a 3-amino-1,2,4-dithiazolidine-5-one. Another aspect of the present invention relates to a method of preparing a phosphorothioate by treating a phosphite with a sulfur-transfer reagent of the invention. In a preferred embodiment, the sulfur-transfer agent is a 3-amino-1,2,4-dithiazolidine-5-one. Another aspect of the present invention relates to compounds that scavenge acrylonitrile produced during the deprotection of phosphate groups bearing ethylnitrile protecting groups. In a preferred embodiment, the acrylonitrile scavenger is a polymer-bound thiol. Another aspect of the present invention relates to agents used to oxidize a phosphite to a phosphate. In a preferred embodiment, the oxidizing agent is sodium chlorite, chloroamine, or pyridine-N-oxide. Another aspect of the present invention relates to methods of purifying an oligonucleotide by annealing a first single-stranded oligonucleotide and second single-stranded oligonucleotide to form a double-stranded oligonucleotide; and subjecting the double-stranded oligonucleotide to chromatographic purification. In a preferred embodiment, the chromatographic purification is high-performance liquid chromatography.

39 Claims, 51 Drawing Sheets

U.S. PATENT DOCUMENTS

| | | |
|---|---|---|
| 2002/0162126 A1 | 10/2002 | Beach et al. |
| 2002/0182590 A1 | 12/2002 | Strange et al. |
| 2003/0084471 A1 | 5/2003 | Beach et al. |
| 2003/0108923 A1 | 6/2003 | Tuschl et al. |
| 2003/0143732 A1 | 7/2003 | Fosnaugh et al. |
| 2003/0148507 A1 | 8/2003 | Fosnaugh et al. |
| 2003/0157030 A1 | 8/2003 | Davis et al. |
| 2003/0167490 A1 | 9/2003 | Hunter et al. |
| 2003/0170891 A1 | 9/2003 | McSwiggen |
| 2003/0175950 A1 | 9/2003 | McSwiggen |
| 2003/0190635 A1 | 10/2003 | McSwiggen |
| 2003/0190661 A1 | 10/2003 | Gruber et al. |
| 2003/0204077 A1 | 10/2003 | Simms |
| 2003/0206887 A1 | 11/2003 | Morrissey et al. |
| 2004/0009522 A1 | 1/2004 | Wu |
| 2004/0009946 A1 | 1/2004 | Lewis et al. |
| 2004/0014113 A1 | 1/2004 | Yang et al. |
| 2004/0018181 A1 | 1/2004 | Kufe et al. |
| 2004/0018999 A1 | 1/2004 | Beach et al. |
| 2004/0019001 A1 | 1/2004 | McSwiggen |
| 2004/0044190 A1 | 3/2004 | Sproat |
| 2004/0058886 A1 | 3/2004 | Scaringe |
| 2004/0063654 A1 | 4/2004 | Davis et al. |
| 2004/0077574 A1 | 4/2004 | Klinghoffer et al. |
| 2004/0086884 A1 | 5/2004 | Beach et al. |
| 2004/0121353 A1 | 6/2004 | Lewis et al. |
| 2004/0138163 A1 | 7/2004 | McSwiggen et al. |
| 2004/0142895 A1 | 7/2004 | Lockridge et al. |
| 2004/0147735 A1* | 7/2004 | Laurent et al. ............... 536/25.3 |
| 2004/0161777 A1 | 8/2004 | Baker et al. |
| 2004/0191905 A1 | 9/2004 | Stevenson et al. |
| 2004/0192626 A1 | 9/2004 | McSwiggen et al. |
| 2004/0192629 A1 | 9/2004 | Xu et al. |
| 2004/0198640 A1 | 10/2004 | Leake et al. |
| 2004/0198682 A1 | 10/2004 | McSwiggen et al. |
| 2004/0203024 A1 | 10/2004 | Baker et al. |
| 2004/0203145 A1 | 10/2004 | Zamore et al. |
| 2004/0204420 A1 | 10/2004 | Rana |
| 2004/0209831 A1 | 10/2004 | McSwiggen et al. |
| 2004/0209832 A1 | 10/2004 | McSwiggen et al. |
| 2004/0214198 A1 | 10/2004 | Rana |
| 2004/0219671 A1 | 11/2004 | McSwiggen et al. |
| 2004/0220128 A1 | 11/2004 | Paveco et al. |
| 2004/0224405 A1 | 11/2004 | Leake et al. |
| 2004/0229266 A1 | 11/2004 | Tuschl et al. |
| 2004/0234504 A1 | 11/2004 | Verma et al. |
| 2004/0235775 A1 | 11/2004 | Kung et al. |
| 2004/0249178 A1 | 12/2004 | Vargeese et al. |
| 2004/0259247 A1 | 12/2004 | Tuschl et al. |
| 2004/0259248 A1 | 12/2004 | Tuschl et al. |
| 2004/0266707 A1 | 12/2004 | Leake et al. |
| 2005/0004063 A1 | 1/2005 | Kung et al. |
| 2005/0014172 A1 | 1/2005 | Richards et al. |
| 2005/0020525 A1 | 1/2005 | McSwiggen et al. |
| 2005/0026278 A1 | 2/2005 | Tuschl et al. |
| 2005/0032733 A1 | 2/2005 | McSwiggen et al. |
| 2005/0042646 A1 | 2/2005 | Davidson et al. |
| 2005/0048529 A1 | 3/2005 | McSwiggen |
| 2005/0054596 A1 | 3/2005 | McSwiggen et al. |
| 2005/0054598 A1 | 3/2005 | McSwiggen |
| 2005/0054847 A1 | 3/2005 | Madden et al. |
| 2005/0059817 A1 | 3/2005 | Beigelman et al. |
| 2005/0070497 A1 | 3/2005 | McSwiggen et al. |
| 2005/0075304 A1 | 4/2005 | McSwiggen et al. |
| 2005/0079610 A1 | 4/2005 | Polisky et al. |
| 2005/0096284 A1 | 5/2005 | McSwiggen |
| 2005/0106726 A1 | 5/2005 | McSwiggen et al. |
| 2005/0119211 A1 | 6/2005 | Chowrira et al. |
| 2005/0119212 A1 | 6/2005 | Haeberli et al. |
| 2005/0124566 A1 | 6/2005 | Robin et al. |
| 2005/0124567 A1 | 6/2005 | McSwiggen et al. |
| 2005/0124568 A1 | 6/2005 | Usman et al. |
| 2005/0124569 A1 | 6/2005 | Guerciolini et al. |
| 2005/0130181 A1 | 6/2005 | McSwiggen |
| 2005/0136436 A1 | 6/2005 | McSwiggen et al. |
| 2005/0137153 A1 | 6/2005 | McSwiggen et al. |
| 2005/0137155 A1 | 6/2005 | McSwiggen et al. |
| 2005/0142578 A1 | 6/2005 | Usman et al. |
| 2005/0143333 A1 | 6/2005 | Richards et al. |
| 2005/0148530 A1 | 7/2005 | McSwiggen et al. |
| 2005/0153914 A1 | 7/2005 | McSwiggen et al. |
| 2005/0153915 A1 | 7/2005 | Usman et al. |
| 2005/0153916 A1 | 7/2005 | McSwiggen et al. |
| 2005/0158735 A1 | 7/2005 | McSwiggen et al. |
| 2005/0159376 A1 | 7/2005 | McSwiggen et al. |
| 2005/0159378 A1 | 7/2005 | McSwiggen et al. |
| 2005/0159379 A1 | 7/2005 | McSwiggen et al. |
| 2005/0159380 A1 | 7/2005 | Guerciolini et al. |
| 2005/0159381 A1 | 7/2005 | McSwiggen et al. |
| 2005/0159382 A1 | 7/2005 | McSwiggen et al. |
| 2005/0164224 A1 | 7/2005 | McSwiggen et al. |
| 2005/0164966 A1 | 7/2005 | McSwiggen et al. |
| 2005/0164967 A1 | 7/2005 | McSwiggen et al. |
| 2005/0164968 A1 | 7/2005 | McSwiggen et al. |
| 2005/0170371 A1 | 8/2005 | McSwiggen et al. |
| 2005/0171039 A1 | 8/2005 | McSwiggen et al. |
| 2005/0171040 A1 | 8/2005 | Polisky et al. |
| 2005/0176018 A1 | 8/2005 | Thompson et al. |
| 2005/0176024 A1 | 8/2005 | McSwiggen et al. |
| 2005/0176025 A1 | 8/2005 | McSwiggen et al. |
| 2005/0176045 A1 | 8/2005 | Fedorov et al. |
| 2005/0176663 A1 | 8/2005 | McSwiggen et al. |
| 2005/0176664 A1 | 8/2005 | Richards et al. |
| 2005/0176665 A1 | 8/2005 | McSwiggen |
| 2005/0176666 A1 | 8/2005 | Richards et al. |
| 2005/0182006 A1 | 8/2005 | McSwiggen et al. |
| 2005/0182007 A1 | 8/2005 | McSwiggen et al. |
| 2005/0182008 A1 | 8/2005 | McSwiggen et al. |
| 2005/0182009 A1 | 8/2005 | McSwiggen et al. |
| 2005/0182010 A1 | 8/2005 | de Haan |
| 2005/0187174 A1 | 8/2005 | Richards et al. |
| 2005/0191618 A1 | 9/2005 | McSwiggen et al. |
| 2005/0191638 A1 | 9/2005 | McSwiggen |
| 2005/0196765 A1 | 9/2005 | McSwiggen et al. |
| 2005/0196767 A1 | 9/2005 | McSwiggen et al. |
| 2005/0196781 A1 | 9/2005 | Robin et al. |
| 2005/0197312 A1 | 9/2005 | Fitzgerald et al. |
| 2005/0202077 A1 | 9/2005 | Watson et al. |
| 2005/0203040 A1 | 9/2005 | Richards et al. |
| 2005/0203044 A1 | 9/2005 | Zinnen |
| 2005/0208658 A1 | 9/2005 | Castonguay |
| 2005/0209179 A1 | 9/2005 | McSwiggen et al. |
| 2005/0209180 A1 | 9/2005 | Jadhav et al. |
| 2005/0209182 A1 | 9/2005 | Morrissey et al. |
| 2005/0215777 A1 | 9/2005 | Vargeese et al. |
| 2005/0222064 A1 | 10/2005 | Vargeese et al. |
| 2005/0222066 A1 | 10/2005 | Richards et al. |
| 2005/0223427 A1 | 10/2005 | Leake et al. |
| 2005/0227935 A1 | 10/2005 | McSwiggen et al. |
| 2005/0227936 A1 | 10/2005 | McSwiggen et al. |
| 2005/0227937 A1 | 10/2005 | Pavco et al. |
| 2005/0233329 A1 | 10/2005 | McSwiggen et al. |
| 2005/0233344 A1 | 10/2005 | McSwiggen et al. |
| 2005/0233996 A1 | 10/2005 | McSwiggen |
| 2005/0233997 A1 | 10/2005 | Richards et al. |
| 2005/0233998 A1 | 10/2005 | Jadhav et al. |
| 2005/0234006 A1 | 10/2005 | Tuschl et al. |
| 2005/0234007 A1 | 10/2005 | Tuschl et al. |
| 2005/0234232 A1 | 10/2005 | Beigelman et al. |
| 2005/0239731 A1 | 10/2005 | McSwiggen et al. |
| 2005/0239739 A1 | 10/2005 | Matulic-Adamic et al. |
| 2005/0245475 A1 | 11/2005 | Khvorova et al. |
| 2005/0246794 A1 | 11/2005 | Khvorova et al. |
| 2005/0255120 A1 | 11/2005 | Simon |
| 2005/0255487 A1 | 11/2005 | Khvorova et al. |
| 2005/0256068 A1 | 11/2005 | McSwiggen et al. |
| 2005/0256076 A1 | 11/2005 | Bumcrot |
| 2005/0260214 A1 | 11/2005 | Simon |
| 2005/0260620 A1 | 11/2005 | Christiano et al. |
| 2005/0260652 A1 | 11/2005 | Ruvkun et al. |
| 2005/0261212 A1 | 11/2005 | McSwiggen |
| 2005/0261219 A1 | 11/2005 | Richards et al. |
| 2005/0261222 A1 | 11/2005 | Wolbert et al. |
| 2005/0266422 A1 | 12/2005 | Vagle et al. |
| 2005/0267058 A1 | 12/2005 | McSwiggen et al. |
| 2005/0277133 A1 | 12/2005 | McSwiggen |
| 2005/0277608 A1 | 12/2005 | Guerciolini et al. |

| | | | |
|---|---|---|---|
| 2005/0282188 A1 | 12/2005 | Haeberli et al. | |
| 2005/0287128 A1 | 12/2005 | Guerciolini et al. | |
| 2005/0287668 A1 | 12/2005 | Finney | |
| 2005/0288242 A1 | 12/2005 | McSwiggen | |
| 2005/0288243 A1 | 12/2005 | Xu et al. | |

FOREIGN PATENT DOCUMENTS

| | | | |
|---|---|---|---|
| DE | 3406011 A1 | 8/1985 |
| EP | 0108908 A | 5/1984 |
| EP | 0713132 B1 | 10/1995 |
| EP | 0 568 379 B1 | 11/1998 |
| EP | 0992506 B1 | 10/1999 |
| EP | 0 992 506 B1 | 8/2003 |
| GB | 1242955 A | 8/1971 |
| GB | 2011391 A | 7/1979 |
| GB | 1575202 | 9/1980 |
| JP | 61-167945 A | 7/1986 |
| JP | 02-304568 A | 12/1990 |
| JP | 06-047275 A | 2/1994 |
| JP | 06-279634 A | 10/1994 |
| JP | 9509323 | 9/1997 |
| JP | 2000-510872 A | 8/2000 |
| JP | 2005-515261 A | 5/2005 |
| NL | 8902521 A | 5/1991 |
| WO | WO 93/13118 A1 | 7/1993 |
| WO | 9523225 A2 | 2/1995 |
| WO | WO 95/25753 | 9/1995 |
| WO | WO 98/39290 A1 | 9/1998 |
| WO | 9854198 A1 | 12/1998 |
| WO | WO 03/062280 A2 | 7/2003 |
| WO | 2004007748 A2 | 1/2004 |

OTHER PUBLICATIONS

Soderberg et al. J. Carbohydrate Chemistry, 2001, 20(5), p. 397-410.*
Ogilvie et al. Can. J. Chem, 1978, 56, p. 2768-2780.*
Hogrefe et al. Nucleic Acids Research, 1993, 21(20), p. 4739-4741.*
Sanghvi, Y.S. et al.: Improved process for the preparation of nucleosidic phosphoramidites using a safer and cheaper activator, Org. Process Res. Dev., vol. 4, 2000, pp. 175-181, XP002350648.
Patent Abstracts of Japan, vol. 1998, No. 08, Jun. 30, 1998 & JP 10 072448 A (Toagosei Co. Ltd.) Mar. 17, 1998, Abstract.
Patent Abstracts of Japan. vol. 2003, No. 12, Dec. 5, 2003 & JP 2004 099532 A (Sigma Genosys Japan KK), Apr. 2, 2004, Abstract.
Tang, J. et al.: "Large-scale synthesis of oligonucleotide phosphorothioates using 3-amino-1,2,4-dithoazole-5-thione as an efficient sulfur-transfer reagent" Org. Process Res. Dev., vol. 4, 2000, pp. 194-198, XP002350649.
International Search Report for PCT/US2005/011490 mailed on Dec. 28, 2005.
Nurminen et al., "Alcoholysis of dialkyl tetrazolylphosphonites", J. Chem. Soc., Perkin Trans. 2, 1999, p. 2551-2556.
Dahl et al., Mechanistic studies on the phosphoramidite coupling reaction in oligonucleotide synthesis. I. Evidence for mucleophilic catalysis by tetrazole and rate variations with the phosphorus substituents, vol. 15, No. 4, Nucleic Acids Research, 1987, vol. 15, No. 4, pp. 1729-1743.
Office Action dated May 20, 2008 for U.S. Appl. No. 11/099,430.
Office Action dated Nov. 22, 2010 for U.S. Appl. No. 12/351,605.
Welz et al. "5(Benzylmercapto)-1H-tetrazole as activator for 2'-O-TBDMS phosphoramidite building blocks in RNA synthesis", Tetrahedron Letters, 2002, 43, pp. 795-797.
Hauptmann et. al. "Syntheses and ligand-binding studies of 1α- and 17α-aminoalkyl dihydrotestosterone derivatives to human sex hormone-binding globulin", Steroids, 68, 2003, pp. 629-639.
Vaman Rao et al., "Dibenzoyl Tetrasulphide—A Rapid Sulphure Transfer Agent in the Synthesis of Phosphorothioate Analogues of Oligonucleotides", Tetrahedron Letters, vol. 33, No. 33, pp. 4839-4842, 1992.
Entry for thiourea, Hawley's Condensed Chemical Dictionary, 2002, John Wiley & Sons, 14th ed, http://www.knovel.com/, accessed online on Nov. 17, 2010.
Xu et al., "Use of 1,2,4-dithiazolidine-3,5-dione (DtsNH) and 3-ethoxy-1,2,4-dithiazoline-5-one (EDITH) for synthesis of phosphorothioate-containing oligodeoxyribonucleotides," Nucleic Acids Research, 1996, 24(9), p. 1602-1607.
Iwakawa et al., "Cycloaddition in Synthesis of Sulfonamide Derivatives. Part 6. Unexpected Products from the Reaction of Dithiocarbamate with Chlorosulfonyl Isocyanate. A Novel Synthetic Route to 5-Amino-1,2,4- dithiazol-3-one and N,N-Disubstituted N'-Chlorosulfonylcarbamimidoyl Chloride," Heterocycles, 1994, 38(5), p. 1015-1024.
Yarovenko et al., "Synthesis of Carbamoyl-Containing N,S-Heterocyclic Compounds," Phosphorus, Sulfur, and Silicon, 2003, 178, p. 1283-1288.
Efimov et al., "New efficient sulfurizing reagents for the preparation of oligodeoxyribonucleotide phosphorothioate analogues", Nucleic Acids Research, 1995, vol. 23, No. 20, p. 4029-4033.
Bereman et al., "Coordination chemistry of new sulfur containing ligands—21. Selected transition element complexes of pyrrole-N-carbothioate: A new type of monothiocarbamate ligand", Journal of Inorganic and Nuclear Chemistry, 1981, vol. 43, No. 11, p. 2729-2734.
Throdahl et al., "Vulcanization of Buna-S (GR-S) With Organic Sulfur Compounds. II.", Rubber Chemistry and Technology, 1945, vol. 18, p. 110-115.
Lawson et al., "Derivatives of 5-amino-1,2,4-dithiazole-3-thione", The Michigan Academician 5(4):465-470 (1973).
Wobig, "Acylamino-1.2.4-dithiazolinthione aus Xanthanwasserstoff and Acylchloriden", Liebigs Ann. Chem. 745:119-123 (1971).
Wobig, "Alkylierung von 5-Acylamino-3H-1,2,4-dithiazol-3-thionen", Liebigs Ann. Chem. 5:1018-1024 (1975).
Zhang et al., "A novel polymer-supported sulfer-transfer reagent for the synthesis of phosphorothioates", Tetrahedron Letters 43:4347-4349 (2002).
Greene et al., "Protective groups in organic synthesis", John Wiley & Sons, Inc., 3 edition:113-148 (1999).

* cited by examiner

Figure 1
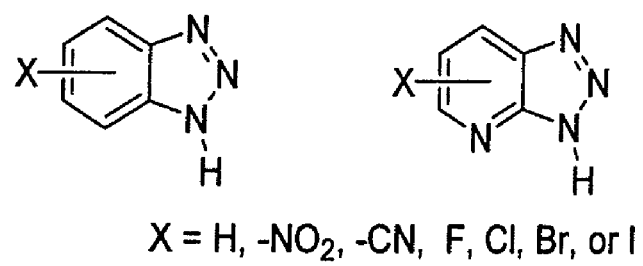
X = H, -NO₂, -CN, F, Cl, Br, or I
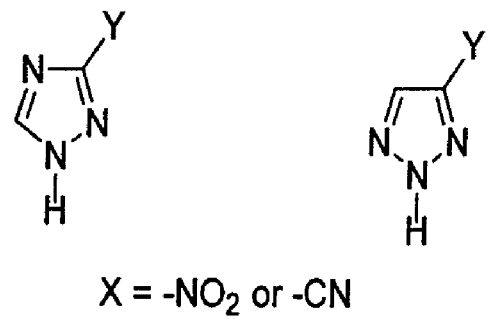
X = -NO₂ or -CN

Figure 2

| Entry | Chemical Composition of Activator |
|---|---|
| 35 |  with 1-40 mol % of its corresponding mono or di or trialkyl ammonium salt in acetonitrile or any other organic solvent. |
| 36 |  with 1-40 mol % of its corresponding mono or di or trialkyl ammonium salt in acetonitrile or any other organic solvent. |
| 37 | 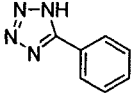 with 1-40 mol % of its corresponding mono or di or trialkyl ammonium salt in acetonitrile or any other organic solvent. |
| 38 | 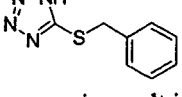 with 1-40 mol % of its corresponding mono or di or trialkyl ammonium salt in acetonitrile or any other organic solvent. |
| 39 |  with 1-40 mol % of its corresponding mono or di or trialkyl ammonium salt in acetonitrile or any other organic solvent. |
| 40 |  with 1-40 mol % of its corresponding mono or di or trialkyl ammonium salt in acetonitrile or any other organic solvent. |
| 41 |  with 1-40 mol % of its corresponding mono or di or trialkyl ammonium salt in acetonitrile or any other organic solvent. |
| 42 | 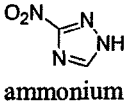 with 0-40 mol % of its corresponding mono or di or trialkyl ammonium salt in acetonitrile or any other organic solvent. |
| 43 |  with 0-40 mol % of its corresponding mono or di or trialkyl ammonium salt in acetonitrile or any other organic solvent. |

Figure 3

| Entry | Chemical Composition of Activator |
|---|---|
| 44 | 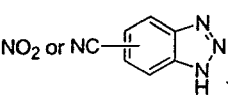 with 0-40 mol % of its corresponding mono or di or trialkyl ammonium salt in acetonitrile or any other organic solvent. |
| 45 | 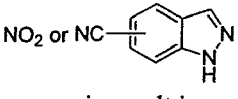 with 1-40 mol % of its corresponding mono or di or trialkyl ammonium salt in acetonitrile or any other organic solvent. |
| 46 |  with 1-40 mol % of its corresponding mono or di or trialkyl ammonium salt in acetonitrile or any other organic solvent. |
| 47 | 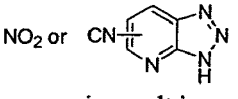 with 1-40 mol % of its corresponding mono or di or trialkyl ammonium salt in acetonitrile or any other organic solvent. |
| 48 |  with 1-40 mol % of its corresponding mono or di or trialkyl ammonium salt in acetonitrile or any other organic solvent. |

Figure 4
| | R' | R" |
|---|---|---|
| 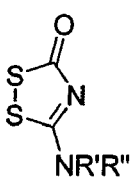 NR'R" | H | H |
| | H | Me |
| | H | Et |
| | H | iPr |
| | H | tBu |
| | Me | Me |
| | Et | Et |
| | iPr | iPr |
| | tBu | tBu |
| | H | Benzyl |
| | H | Phenyl |
| | H or (CH$_2$)$_n$-CH$_3$, Where n = 0-11 |  and X = any alkyl or aryl |
| | H or (CH$_2$)$_n$-CH$_3$, Where n = 0-11 |  and X = any alkyl or aryl |
| | H or (CH$_2$)$_n$-CH$_3$, Where n = 0-11 |  and X = any alkyl or aryl |
| | H or (CH$_2$)$_n$-CH$_3$, Where n = 0-11 |  and X = any alkyl or aryl |
| | H or (CH$_2$)$_n$-CH$_3$, Where n = 0-11 |  and X = any alkyl or aryl |
| | H or (CH$_2$)$_n$-CH$_3$, Where n = 0-11 |  and X = any alkyl or aryl |

Figure 6

| Sequence | Thiolation | | crude | | Purification |
|---|---|---|---|---|---|
| | Agent | Quantity | % Y | % fl IEX | |
| 25 | 0.05 M EDITH | 1CV in 1 min. | 23 | 55 | 1.2 kAU (= 11% of crude) @ 98%fl |
| 26 | 0.05 M EDITH | 1CV in 1 min. | 30 | 25% | not purified |
| 25 | 0.2 M PADS (fresh) | 4CV in 2.4 minutes | 27 | nd | 4.6 kAU (= 40% of crude) @ 43%fl) |
| 26 | 0.2 M PADS (fresh) | 4CV in 2.4 minutes | 23 | nd | 2.3 kAU (= 25% of crude) @ 85% Repurified to 1.0 kAU @ 93%fl |
| 25 | 0.2 M PADS (aged) | 2CV in 1.2 minutes | 33 | <20 | not purified |
| 26 | 0.2 M PADS (aged) | 2CV in 1.2 minutes | 29 | <20 | not purified |
| 25 | 0.2 M PADS (aged) | 4CV in 2.4 minutes | 33 | <20: small deprotectio n = 31 fl | not purified |
| 26 | 0.2 M PADS (aged) | 6CV in 7.2 minutes | 33 | <20 fl | not purified |

Figure 7
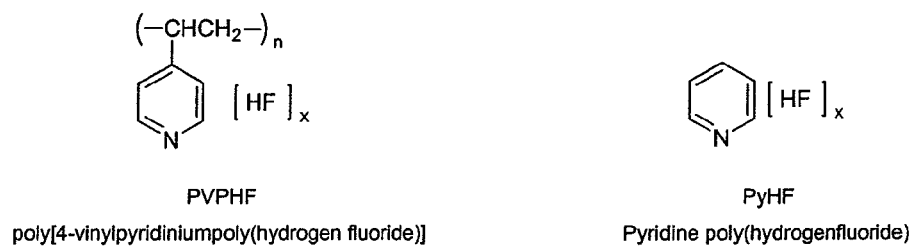
PVPHF
poly[4-vinylpyridiniumpoly(hydrogen fluoride)]
PyHF
Pyridine poly(hydrogenfluoride)
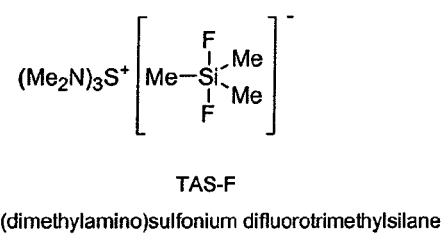
TAS-F
Tris(dimethylamino)sulfonium difluorotrimethylsilane
Bases used:
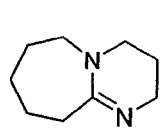 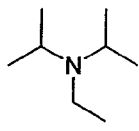  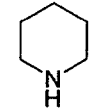 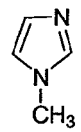
DBU · Hunig base · Pyridine · Piperidine · N-methylimidazole

AL-DP-4014
(M.W 13315.04)

5'-GCGGGAUCAAACCUCACCAAdTdT-3'     AL-4112 mw 6635.07
3'-dTdTCGCCUAGUUUGGAGUGGUU-5'      AL-4180 mw 6679.97

AL-DP-4127
(m.w 13475.7)

5'-G*G*GGAUCAAACCUCACCA*A*dT*dT-3'     AL-2200 mw 6715.40
3'-dT*dT*C*GCCUAGUUUGGAGUGG*U*U-5'     AL-2201 mw 6760.30

AL-DP-4139
(M.W 13315.04)

5'-GGGGGAACAAUCCUGACCAAdTdT-3'     AL-2299 mw 6675.09
3'-dTdTCGCCCUUGUUAGGACUGGUU-5'     AL-23mw 6639.94

AL-DP-4140
(m.w 13475.69)

5'-G*C*GGAACAAUCCUGACCA*A*dT*dT-3'     AL-2281 mw 6655.42
3'-dT*dT*C*GCCCUUGUUAGGACUGG*U*U-5'     AL-2282 mw 6720.27

FIG. 10

I. Cholesterol-Hyp Amidite

II. Cholesterol-Hyp Icaa CPG

III. Hydroxyproline-Amine Amidite

IV. Hydroxyproline-Amine Icaa CPG

PROCESSES AND REAGENTS FOR DESILYLATION OF OLIGONUCLEOTIDES

RELATED APPLICATIONS

This application is a continuation of U.S. patent application Ser. No. 11/099,430, filed Apr. 5, 2005; which claims the benefit of priority to U.S. Provisional Patent Application Ser. No. 60/559,782, filed Apr. 5, 2004; the entirety of both of which is hereby incorporated by reference.

BACKGROUND OF THE INVENTION

The study of oligonucleotides is a key area of research for many academic and industrial laboratories. See S. Agrawal *Trends in Biotechnology* 1996, 14, 375-382; J. Marr *Drug Discovery Today* 1996, 1, 94-102; and W. Rush *Science* 1997, 276, 1192-1193. The therapeutic and diagnostic potential of oligonucleotides has sparked a substantial amount of research activity. One important application of oligonucleotides is the ability to modulate gene and protein function in a sequence-specific manner. However, many research efforts are hampered by the small quantities of oligonucleotides that are available for study. A method to produce large quantities of oligonucleotide compounds having high purity would greatly facilitate oligonucleotide research. Furthermore, it would be highly useful to be able to prepare derivatives of certain oligonucleotides. However, the synthesis of oligonucleotides and their analogs is often a tedious and costly process.

RNA is generally synthesized and purified by methodologies based on the following steps: phosphoramidite coupling using tetrazole as the activating agent, oxidation of the phosphorus linker to the diester, deprotection of exocyclic amino protecting groups using $NH_4OH$, removal of 2'-OH alkylsilyl protecting groups using tetra-n-butylammonium fluoride (TBAF), and gel purification and analysis of the deprotected RNA. Examples of chemical synthesis, deprotection, purification and analysis procedures are provided by Usman et al. in *J. Am. Chem. Soc.* 1987, 109, 7845; Scaringe et al. in *Nucleic Acids Res.* 1990, 18, 5433-5341; Perreault et al. in *Biochemistry* 1991, 30, 4020-4025; and Slim and Gait in *Nucleic Acids Res.* 1991, 19, 1183-1188. Odai and coworkers describe reverse-phase chromatographic purification of RNA fragments used to form a ribozyme. See Odai et al. *FEBS Lett.* 1990, 267, 150-152. Unfortunately, the aforementioned chemical synthesis, deprotection, purification and analysis procedures are time consuming (10-15 min. coupling times), subject to inefficient activation of the RNA amidites by tetrazole, incomplete deprotection of the exocyclic amino protecting groups by $NH_4OH$, limited by the low capacity of RNA purification using gel electrophoresis, and further limited by low resolution analysis of the RNA by gel electrophoresis. Therefore, the need exists for improved synthetic processes for the synthesis of oligonucleotides.

One important class of oligonucleotide analogues are compounds that have a phosphorothioate in place of the phosphodiester linkage. Phosphorothioate analogues are important compounds in nucleic acid research and protein research. For example, phosphorothioate-containing antisense oligonucleotides have been used in vitro and in vivo as inhibitors of gene expression. Site-specific attachment of reporter groups onto the DNA or RNA backbone is facilitated by incorporation of single phosphorothioate linkages. Phosphorothioates have also been introduced into oligonucleotides for mechanistic studies on DNA-protein and RNA-protein interactions, as well as catalytic RNAs.

Introduction of phosphorothioate linkages into oligonucleotides, assembled by solid-phase synthesis, can be achieved using either an H-phosphonate approach or a phosphoramidite approach. The H-phosphonate approach involves a single sulfur-transfer step, carried out after the desired sequence has been assembled, to convert all of the internucleotide linkages to phosphorothioates. Alternatively, the phosphoramidite approach features a choice at each synthetic cycle: a standard oxidation provides the normal phosphodiester internucleotide linkage, whereas a sulfurization step introduces a phosphorothioate at that specific position in the sequence. An advantage of using phosphoramidite chemistry is the capability to control the state of each linkage, $P=O$ vs. $P=S$, in a site-specific manner. The earliest studies to create phosphorothioates used elemental sulfur, but the success of the phosphoramidite approach is dependent on the availability and application of more efficient, more soluble sulfur-transfer reagents that are compatible with automated synthesis. Therefore, the need exists for novel sulfur-transfer reagents that are compatible with automated oligonucleotide synthesis.

Another important class of oligonucleotides is double-stranded RNA which can be used to initiate a type of gene silencing known as RNA interference (RNAi). RNA interference is an evolutionarily conserved gene-silencing mechanism, originally discovered in studies of the nematode *Caenorhabditis elegans* (Lee et al, Cell 75:843 (1993); Reinhart et al., Nature 403:901 (2000)). It is triggered by introducing dsRNA into cells expressing the appropriate molecular machinery, which then degrades the corresponding endogenous mRNA. The mechanism involves conversion of dsRNA into short RNAs that direct ribonucleases to homologous mRNA targets (summarized, Ruvkun, Science 2294: 797 (2001)). This process is related to normal defenses against viruses and the mobilization of transposons.

Double-stranded ribonucleic acids (dsRNAs) are naturally rare and have been found only in certain microorganisms, such as yeasts or viruses. Recent reports indicate that dsRNAs are involved in phenomena of regulation of expression, as well as in the initiation of the synthesis of interferon by cells (Declerq et al., Meth. Enzymol. 78:291 (1981); Wu-Li, Biol. Chem. 265:5470 (1990)). In addition, dsRNA has been reported to have anti-proliferative properties, which makes it possible also to envisage therapeutic applications (Aubel et al., Proc. Natl. Acad. Sci., USA 88:906 (1991)). For example, synthetic dsRNA has been shown to inhibit tumor growth in mice (Levy et al. Proc. Nat. Acad. Sci. USA, 62:357-361 (1969)), is active in the treatment of leukemic mice (Zeleznick et al., Proc. Soc. Exp. Biol. Med. 130:126-128 (1969)); and inhibits chemically-induced tumorigenesis in mouse skin (Gelboin et al., Science 167:205-207 (1970)).

Treatment with dsRNA has become an important method for analyzing gene functions in invertebrate organisms. For example, Dzitoveva et al. showed for the first time, that RNAi can be induced in adult fruit flies by injecting dsRNA into the abdomen of anesthetized *Drosophila*, and that this method can also target genes expressed in the central nervous system (Mol. Psychiatry 6(6):665-670 (2001)). Both transgenes and endogenous genes were successfully silenced in adult *Drosophila* by intra-abdominal injection of their respective dsRNA. Moreover, Elbashir et al., provided evidence that the direction of dsRNA processing determines whether sense or antisense target RNA can be cleaved by a small interfering RNA (siRNA)-protein complex (Genes Dev. 15(2): 188-200 (2001)).

Two recent reports reveal that RNAi provides a rapid method to test the function of genes in the nematode *Cae-* norhabditis elegans; and most of the genes on *C. elegans* chromosome I and III have now been tested for RNAi phenotypes (Barstead, Curr. Opin. Chem. Biol. 5(1):63-66 (2001); Tavernarakis, Nat. Genet. 24(2):180-183 (2000); Zamore, Nat. Struct. Biol. 8(9):746-750 (2001).). When used as a rapid approach to obtain loss-of-function information, RNAi was used to analyze a random set of ovarian transcripts and have identified 81 genes with essential roles in *C. elegans* embryogenesis (Piano et al., Curr. Biol. 10(24):1619-1622 (2000). RNAi has also been used to disrupt the pupal hemocyte protein of *Sarcophaga* (Nishikawa et al., Eur. J. Biochem. 268(20):5295-5299 (2001)).

Like RNAi in invertebrate animals, post-transcriptional gene silencing (PTGS) in plants is an RNA-degradation mechanism. In plants, this can occur at both the transcriptional and the post-transcriptional levels; however, in invertebrates only post-transcriptional RNAi has been reported to date (Bernstein et al., Nature 409(6818):295-296 (2001). Indeed, both involve double-stranded RNA (dsRNA), spread within the organism from a localized initiating area, to correlate with the accumulation of small interfering RNA (siRNA) and require putative RNA-dependent RNA polymerases, RNA helicases and proteins of unknown functions containing PAZ and Piwi domains.

Some differences are evident between RNAi and PTGS were reported by Vaucheret et al., J. Cell Sci. 114(Pt 17): 3083-3091 (2001). First, PTGS in plants requires at least two genes—SGS3 (which encodes a protein of unknown function containing a coil-coiled domain) and MET1 (which encodes a DNA-methyltransferase)—that are absent in *C. elegans*, and thus are not required for RNAi. Second, all of the *Arabidopsis* mutants that exhibit impaired PTGS are hyper-susceptible to infection by the cucumovirus CMV, indicating that PTGS participates in a mechanism for plant resistance to viruses. RNAi-mediated oncogene silencing has also been reported to confer resistance to crown gall tumorigenesis (Escobar et al., Proc. Natl. Acad. Sci. USA, 98(23):13437-13442 (2001)).

RNAi is mediated by RNA-induced silencing complex (RISC), a sequence-specific, multicomponent nuclease that destroys messenger RNAs homologous to the silencing trigger. RISC is known to contain short RNAs (approximately 22 nucleotides) derived from the double-stranded RNA trigger, but the protein components of this activity remained unknown. Hammond et al. (Science 293(5532):1146-1150 (August 2001)) reported biochemical purification of the RNAi effector nuclease from cultured *Drosophila* cells, and protein microsequencing of a ribonucleoprotein complex of the active fraction showed that one constituent of this complex is a member of the Argonaute family of proteins, which are essential for gene silencing in *Caenorhabditis elegans, Neurospora*, and *Arabidopsis*. This observation suggests links between the genetic analysis of RNAi from diverse organisms and the biochemical model of RNAi that is emerging from *Drosophila* in vitro systems.

Svoboda et al. reported in Development 127(19):4147-4156 (2000) that RNAi provides a suitable and robust approach to study the function of dormant maternal mRNAs in mouse oocytes. Mos (originally known as c-mos) and tissue plasminogen activator mRNAs are dormant maternal mRNAs that are recruited during oocyte maturation, and translation of Mos mRNA results in the activation of MAP kinase. The dsRNA directed towards Mos or TPA mRNAs in mouse oocytes specifically reduced the targeted mRNA in both a time- and concentration-dependent manner, and inhibited the appearance of MAP kinase activity. See also, Svoboda et al. Biochem. Biophys. Res. Commun. 287(5):1099-1104 (2001).

The need exists for small interfering RNA (siRNA) conjugates having improved pharmacologic properties. In particular, the oligonucleotide sequences have poor serum solubility, poor cellular distribution and uptake, and are rapidly excreted through the kidneys. It is known that oligonucleotides bearing the native phosphodiester (P=O) backbone are susceptable to nuclease-mediated degradation. See L. L. Cummins et al. *Nucleic Acids Res.* 1995, 23, 2019. The stability of oligonucleotides has been increased by converting the P=O linkages to P=S linkages which are less susceptible to degradation by nucleases in vivo. Alternatively, the phosphate group can be converted to a phosphoramidate or alkyl phosphonate, both of which are less prone to enzymatic degradation than the native phosphate. See Uhlmann, E.; Peyman, A. *Chem. Rev.* 1990, 90, 544. Modifications to the sugar groups of the oligonucleotide can confer stability to enzymatic degradation. For example, oligonucleotides comprising ribonucleic acids are less prone to nucleolytic degradation if the 2'-OH group of the sugar is converted to a methoxyethoxy group. See M. Manoharan *ChemBioChem.* 2002, 3, 1257 and references therein.

Therefore, the need exists for improved synthetic processes that facilitate the synthesis of oligonucleotides. Representative examples of needed improvements are better activating agents for phosphoramidite coupling of nucleotides, better sulfur-transfer reagents for preparing phosphorothioate-containing oligonucleotides, and improved procedures for purifying oligonucleotides.

SUMMARY OF THE INVENTION

The present invention relates to processes and reagents for oligonucleotide synthesis and purification. One aspect of the present invention relates to compounds useful for activating phosphoramidites in oligonucleotide synthesis. Another aspect of the present invention relates to a method of preparing oligonucleotides via the phosphoramidite method using an activator of the invention. Another aspect of the present invention relates to sulfur-transfer agents. In a preferred embodiment, the sulfur-transfer agent is a 3-amino-1,2,4-dithiazolidine-5-one. Another aspect of the present invention relates to a method of preparing a phosphorothioate by treating a phosphite with a sulfur-transfer reagent of the invention. In a preferred embodiment, the sulfur-transfer agent is a 3-amino-1,2,4-dithiazolidine-5-one. Another aspect of the present invention relates to compounds that scavenge acrylonitrile produced during the deprotection of phosphate groups bearing ethylnitrile protecting groups. In a preferred embodiment, the acrylonitrile scavenger is a polymer-bound thiol. Another aspect of the present invention relates to agents used to oxidize a phosphite to a phosphate. In a preferred embodiment, the oxidizing agent is sodium chlorite, chloroamine, or pyridine-N-oxide. Another aspect of the present invention relates to methods of purifying an oligonucleotide by annealing a first single-stranded oligonucleotide and second single-stranded oligonucleotide to form a double-stranded oligonucleotide; and subjecting the double-stranded oligonucleotide to chromatographic purification. In a preferred embodiment, the chromatographic purification is high-performance liquid chromatography.

BRIEF DESCRIPTION OF FIGURES

FIG. 1 depicts activator compounds useful in phosphoramidite-mediated oligonucleotide synthesis.

FIG. 2 depicts activating agents useful in phosphoramidite-mediated oligonucleotide synthesis.

FIG. 3 depicts activating agents useful in phosphoramidite-mediated oligonucleotide synthesis.

FIG. 4 depicts sulfur-transfer agents useful in preparing phosphorothioate linkages in oligonucleotides.

FIG. 6 depicts the results of the synthesis of 25 and 26 with PADS or EDITH. Note that 25=5'-GsCsGGAUCAAACCU-CACCAsAsdTsdT-3' (SEQ ID NO: 1), 26=5'-UsUsG-GUGAGGUUUGAUCCGsCsdTsdT-3' (SEQ ID NO: 2), PADS (fresh) indicates that less than 24 hours had elapsed since dissolving, PADS (aged) indicates that greater than 48 hours had elapsed since dissolving, and the term "nd" indicates that the value was not determined. The term "PADS" refers to the compound (benzylC(O)S)$_2$. The term "EDITH" refers to 3-ethoxy-1,2,4-dithiazolidine-5-one.

FIG. 7 depicts desilylating reagents and assorted bases used in oligonucleotide synthesis.

FIG. 10 depicts the structure of AL-4112, AL-4180, AL-DP-4014, AL-2200, AL-2201, AL-DP-4127, AL-2299, AL-2300, AL-DP-4139, AL-2281, AL-2282, and AL-DP-4140 (SEQ ID NOS: 3-6).

DETAILED DESCRIPTION OF THE INVENTION

Figure 5:
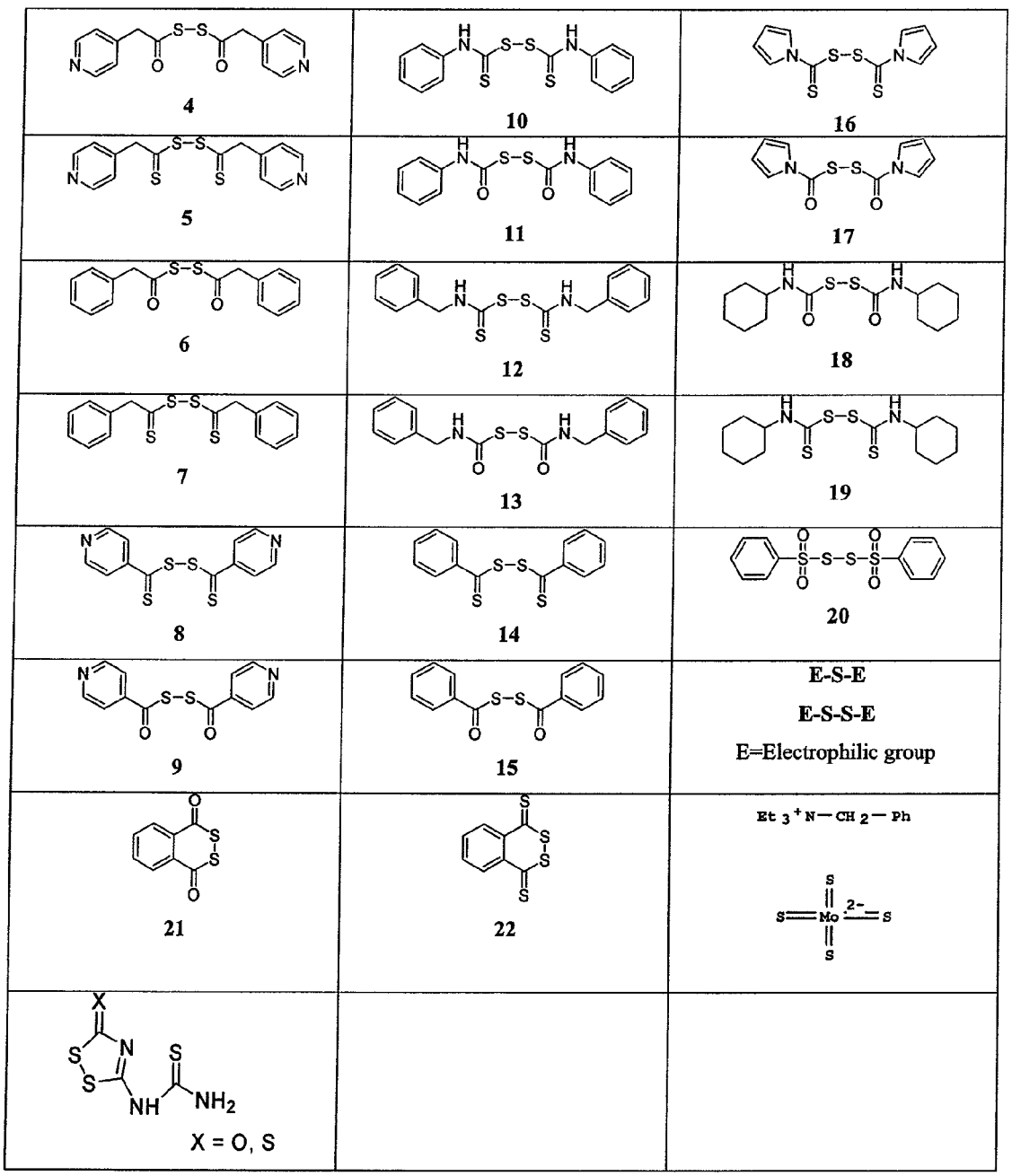
FIG. 5 depicts sulfur-transfer agents useful in preparing phosphorothioate linkages in oligonucleotides.

The present invention relates to processes and reagents for oligonucleotide synthesis and purification. Aspects of the processes and reagents are described in the paragraphs below.
Activators for Phosphoramidite-Mediated Synthesis of Oligonucleotides The most commonly used process in oligonucleotide synthesis using solid phase chemistry is the phosphoramidite approach. In a typical procedure, a phosphoramidite is reacted with a support-bound nucleotide, or oligonucleotide, in the presence of an activator. The phosphoroamidite coupling-product is oxidized to afford a protected phosphate. A variety of different phosphoramidite derivatives are known to be compatible with this procedure, and the most commonly used activator is 1H-tetrazole. Similar processes have been described using a soluble support. See Bonora et al. *Nucleic Acids Res.*, 1993, 21, 1213-1217. The phosphoramidite approach is also widely used in solution phase chemistries for oligonucleotide synthesis. In addition, deoxyribonucleotide phosphoramidite derivatives have been used in the synthesis of oligonucleotides. See Beaucage et al. *Tetrahedron Lett.* 1981, 22, 1859-1862.

Phosphoramidites derivatives from a variety of nucleosides are commercially available. 3'-O-phosphoramidites are the most widely used amidites, but the synthesis of oligonucleotides can involve the use of 5'-O- and 2'-O-phosphoramidites. See Wagner et al. *Nuclosides & Nucleotides* 1997, 17, 1657-1660 and Bhan et al. *Nuclosides & Nucleotides* 1997, 17, 1195-1199. There are also many phosphoramidites available that are not nucleosides (Cruachem Inc., Dulles, Va.; Clontech, Palo Alto, Calif., Glen Research, Sterling, Va., ChemGenes, Wilmington, Mass.).

Prior to performing the phosphoramidite coupling procedure described above, the 3'-OH group of the 5'-O-protected nucleoside has to be phosphityled. Additionally, exocyclic amino groups and other functional groups present on nucleobase moieties are normally protected prior to phosphitylation. Traditionally, phosphitylation of nucleosides is performed by treatment of the protected nucleosides with a phosphitylating reagent such as chloro-(2-cyanoethoxy)-N,N-diisopropylaminophosphine which is very reactive and does not require an activator or 2-cyanoethyl-N,N,N',N'-tetraiso-propylphosphorodiamidite (bis amidite reagent) which requires an activator. After preparation, the nucleoside 3'-O-phosphoramidite is coupled to a 5'-OH group of a nucleoside, nucleotide, oligonucleoside or oligonucleotide. The activator most commonly used in phosphitylation reactions is 1H-tetrazole.

Despite the common usage of 1H-tetrazole in phosphoramidite coupling and phosphitylation reactions, there are inherent problems with the use of 1H-tetrazole, especially when performing larger scale syntheses. For example, 1H-tetrazole is known to be explosive. According to the material safety data sheet (MSDS) 1H-tetrazole (1H-tetrazole, 98%) can be harmful if inhaled, ingested or absorbed through the skin. The MSDS also states that 1H-tetrazole can explode if heated above its melting temperature of 155° C. and may form very sensitive explosive metallic compounds. Hence, 1H-tetrazole requires special handling during its storage, use, and disposal.

In addition to its toxicity and explosive nature, 1H-tetrazole is acidic and can cause deblocking of the 5'-O-protecting group and can also cause depurination during the phosphitylation step of amidite synthesis. See Krotz et al. *Tetrahedron Lett.* 1997, 38, 3875-3878. Inadvertent deblocking of the 5'-O-protecting group is also a problem when chloro-(2-cyanoethoxy)-N,N-diisopropylaminophosphine is used. Recently, trimethylchlorosilane has been used as an activator in the phosphitylation of 5'-O-DMT nucleosides with bis amidite reagent, but this reagent is usually contaminated with HCl which leads to deprotection and formation of undesired products. See W. Dabkowski et al. *Chem. Comm.* 1997, 877. The results for this phosphitylation are comparable to those for 1H-tetrazole. Activators with a higher pKa (i.e., less acidic) than 1H-tetrazole (pKa 4.9) such as 4,5-dicyanoimidazole (pKa 5.2) have been used in the phosphitylation of 5'-O-DMT thymidine. See C. Vargeese *Nucleic Acids Res.* 1998, 26, 1046-1050.

Another disadvantage to using 1H-tetrazole is the cost of the reagent. The 2003 Aldrich Chemical Company catalog lists 1H-tetrazole at over seven dollars a gram. Furthermore, due to the explosive nature of 1H-tetrazole it is only listed as a dilute solution in acetonitrile. This reagent is used in excess of the stoichiometric amount of nucleoside present in the reaction mixture resulting in considerable cost, especially during large-scale syntheses.

The solubility of 1H-tetrazole is also a factor in the large-scale synthesis of phosphoramidites, oligonucleotides and their analogs. The solubility of 1H-tetrazole is about 0.5 M in acetonitrile. This low solubility is a limiting factor on the volume of solvent that is necessary to run a phosphitylation reaction. An activator having higher solubility would be preferred in order to minimize the volume of solvents used in the reactions, thereby lowering the cost and the production of waste effluents. Furthermore, commonly used 1H-tetrazole (0.45 M solution) for oligonucleotide synthesis precipitates 1H-tetrazole when the room temperature drops below 20° C. Inadvertent precipitation of 1H-tetrazole can block the lines on an automated synthesizer leading to synthesis failure.

In response to the problems associated with the use of 1H-tetrazole, several activators for phosphoramidite coupling have been reported. 5-Ethylthio-1H-tetrazole (Wincott, F., et al. *Nucleic Acids Res.* 1995, 23, 2677) and 5-(4-nitrophenyl)-1H-tetrazole (Pon, R. T. *Tetrahedron Lett.* 1987, 28, 3643) have been used for the coupling of sterically crowded ribonucleoside monomers e.g. for RNA-synthesis. The pKa's for theses activators are 4.28 and 3.7 (1:1 ethanol:water), respectively. The use of pyridine hydrochloride/imidazole (pKa 5.23 (water)) as an activator for coupling of monomers was demonstrated by the synthesis of a dimer (Gryaznov, S. M.; Letsinger, L. M. *Nucleic Acids Res.* 1992, 20, 1879). Benzimidazolium triflate (pKa 4.5 (1:1 ethanol:water)) (Hayakawa et al. *J. Org. Chem.* 1996, 61, 7996-7997) has been used as an activator for the synthesis of oligonucleotides having bulky or sterically crowded phosphorus protecting groups such as aryloxy groups. The use of imidazolium triflate (pKa 6.9 (water)) was demonstrated for the synthesis of a dimer in solution (Hayakawa, Y.; Kataoka, M. *Nucleic Acids and Related Macromolecules: Synthesis, Structure, Function and Applications*, Sep. 4-9, 1997, Ulm, Germany). The use of 4,5-dicyanoimidazole as an activator for the synthesis of nucleoside phosphoramidite and several 2'-modified oligonucleotides including phosphorothioates has also been reported.

Due to ongoing clinical demand, the synthesis of oligonucleotides and their analogs is being performed on increasingly larger scale reactions than in the past. See Crooke et al. *Biotechnology and Genetic Engineering Reviews* 1998, 15, 121-157. There exists a need for phosphoramidite activators that pose fewer hazards, are less acidic, and less expensive than activating agents that are currently being used, such as 1H-tetrazole. This invention is directed to this, as well as other, important ends.

Activators of the Invention

The activator compounds of the invention have superior properties for activating phosphoramidites used in oligonucleotide synthesis. The activator compounds are generally less explosive and more soluble in acetonitrile than 1H-tetrazole. In addition, the activator compounds of the invention required shorter reaction times in the synthesis of a decamer RNA molecule compared to 1H-tetrazole. See Example 1. In certain instances, the activator compound of the invention has an electron-withdrawing group to decrease the pKa of the compound. More acidic activator compounds can increase the rate of the phosphoramidite coupling reaction in certain instances. Importantly, shorter reaction times minimize the opportunity for side reactions to occur, thereby providing the desired product in higher purity. In addition, activator compounds of the invention can be the free heterocyclic compound or a mixture of the activator and its corresponding monoalkyl, dialkyl, or trialkyl ammonium salt with varying salt to activator molar ratio. Select preferred activator compounds of the invention are presented in FIGS. 1, 2, and 3.

One aspect of the present invention relates to a compound represented by formula I:

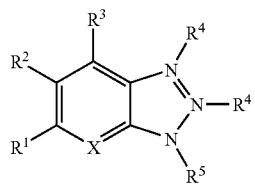

I wherein

X is $C(R^6)$ or N;

$R^1$, $R^2$, $R^3$, and $R^6$ each independently represent H, —$NO_2$, —CN, —$CF_3$, —$SO_2R^8$, —$SR^8$, halogen, alkyl, alkenyl, alkynyl, aryl, aralkyl, alkoxyl, —$OR^7$, —$N(R^7)_2$, —$N(R^7)C(O)R^8$, —$C(O)R^7$, or —$CO_2R^8$; or an instance of $R^1$ and $R^2$, or $R^2$ and $R^3$ can be taken together to form a 4-8 member ring containing 0-4 heteroatoms selected from the group consisting of O, N and S;

$R^4$ is absent or represents independently for each occurrence —$(C(R^9)_2)_nCH_3 \cdot Y$;

$R^5$ is H or —$(C(R^9)_2)_nCH_3$;

$R^7$ represents independently for each occurrence H, alkyl, aryl, or aralkyl;

$R^8$ represents independently for each occurrence alkyl, aryl, or aralkyl;

$R^9$ represents independently for each occurrence H or alkyl;

n represents independently for each occurrence 0 to 15 inclusive; and

Y represents independently for each occurrence halogen or $R^8CO_2^-$.

In certain embodiments, the present invention relates to the aforementioned compound, wherein X is $C(R^6)$.

In certain embodiments, the present invention relates to the aforementioned compound, wherein X is N.

In certain embodiments, the present invention relates to the aforementioned compound, wherein X is $C(R^6)$; $R^1$, $R^2$, $R^3$, and $R^6$ each independently represent H, —$NO_2$, or —CN; $R^4$ is absent; and $R^5$ is H.

In certain embodiments, the present invention relates to the aforementioned compound, wherein X is $C(R^6)$; $R^1$, $R^2$, $R^3$, and $R^6$ are H; $R^4$ is absent; and $R^5$ is H.

In certain embodiments, the present invention relates to the aforementioned compound, wherein X is N; $R^1$, $R^2$, and $R^3$ are H; $R^4$ is absent; and $R^5$ is H.

Another aspect of the present invention relates to a compound represented by formula II:

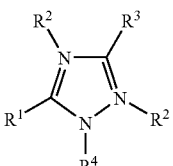

II wherein $R^1$ and $R^3$ each represent independently H, —$NO_2$, —CN, —$CF_3$, —$SO_2R^6$, —$SR^6$, halogen, alkyl, alkenyl, alkynyl, aryl, aralkyl, —$N(R^5)C(O)R^6$, —$C(O)R^5$, or —$CO_2R^6$;

$R^2$ is absent or represents independently for each occurrence —$(C(R^7)_2)_nCH_3 \cdot Y$;

$R^4$ is H or —$(C(R^7)_2)_nCH_3$;

$R^5$ represents independently for each occurrence H, alkyl, aryl, or aralkyl;

$R^6$ represents independently for each occurrence alkyl, aryl, or aralkyl;

$R^7$ represents independently for each occurrence H or alkyl;

n represents independently for each occurrence 0 to 15 inclusive; and

Y represents independently for each occurrence halogen or $R^6CO_2^-$.

In certain embodiments, the present invention relates to the aforementioned compound, wherein $R^1$ and $R^3$ each represent independently H, —$NO_2$, or —CN; $R^2$ is absent; and $R^4$ is H.

In certain embodiments, the present invention relates to the aforementioned compound, wherein $R^1$ is H; $R^3$ is —$NO_2$; $R^2$ is absent; and $R^4$ is H.

Another aspect of the present invention relates to a compound represented by formula II:

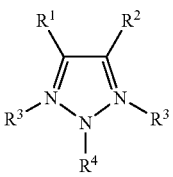

III wherein $R^1$ and $R^2$ each represent independently H, —$NO_2$, —CN, —$CF_3$, —$SO_2R^6$, —$SR^6$, halogen, alkyl, alkenyl, alkynyl, aryl, aralkyl, —$N(R^5)C(O)R^6$, —$C(O)R^5$, or —$CO_2R^6$;

$R^3$ is absent or represents independently for each occurrence —$(C(R^7)_2)_nCH_3 \cdot Y$;

$R^4$ is H or —$(C(R^7)_2)_nCH_3$;

$R^5$ represents independently for each occurrence H, alkyl, aryl, or aralkyl;

$R^6$ represents independently for each occurrence alkyl, aryl, or aralkyl;

$R^7$ represents independently for each occurrence H or alkyl;

n represents independently for each occurrence 0 to 15 inclusive; and

Y represents independently for each occurrence halogen or $R^6CO_2^-$.

In certain embodiments, the present invention relates to the aforementioned compound, wherein $R^1$ and $R^2$ each represent independently H, —$NO_2$, or —CN; $R^4$ is absent; and $R^4$ is H.

In certain embodiments, the present invention relates to the aforementioned compound, wherein $R^1$ is H; $R^2$ is —$NO_2$; $R^3$ is absent; and $R^4$ is H.

Another aspect of the present invention relates to a compound represented by formula IV:

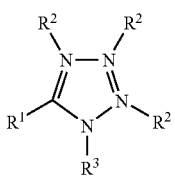

IV wherein
$R^1$ is H, —$SR^5$, alkyl, aryl, —$N(R^4)_2$, —$(C(R^4)_2)_mCO_2R^5$, —$NO_2$, —CN, —$CF_3$, —$SO_2R^5$, —$SR^5$, halogen, alkenyl, alkynyl, aralkyl, —$N(R^4)C(O)R^5$, —$C(O)R^4$, or —$CO_2R^5$;

$R^2$ is absent or represents independently for each occurrence —$(C(R^6)_2)_nCH_3 \cdot Y$;

$R^3$ is H or —$(C(R^6)_2)_nCH_3$;

$R^4$ represents independently for each occurrence H, alkyl, aryl, or aralkyl;

$R^5$ represents independently for each occurrence alkyl, aryl, or aralkyl;

$R^6$ represents independently for each occurrence H or alkyl;

n represents independently for each occurrence 0 to 15 inclusive;

m is 1, 2, 3, 4, 5, 6, 7, or 8; and

Y represents independently for each occurrence halogen or $R^5CO_2^-$.

In certain embodiments, the present invention relates to the aforementioned compound, wherein $R^1$ is —$SR^5$, alkyl, aryl, —$N(R^4)_2$, or —$(C(R^4)_2)_mCO_2R^5$.

In certain embodiments, the present invention relates to the aforementioned compound, wherein $R^2$ is absent, and $R^3$ is H.

In certain embodiments, the present invention relates to the aforementioned compound, wherein $R^1$ is —$SR^5$, alkyl, aryl, —$N(R^4)_2$, or —$(C(R^4)_2)_mCO_2R^5$; $R^2$ is absent; $R^3$ is H; $R^4$ is H; $R^5$ is alkyl or aralkyl; and m is 1.

Another aspect of the present invention relates to a compound represented by formula V:

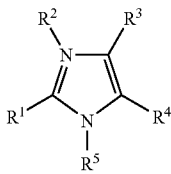

V wherein
$R^1$, $R^3$, and $R^4$ each represent independently H, —$NO_2$, —CN, —$CF_3$, —$SO_2R^7$, —$SR^7$, halogen, alkyl, alkenyl, alkynyl, aryl, aralkyl, —$N(R^6)C(O)R^5$, —$C(O)R^6$, or —$CO_2R^7$;

$R^2$ is absent or represents independently for each occurrence —$(C(R^8)_2)_nCH_3 \cdot Y$;

$R^5$ is H or —$(C(R^8)_2)_nCH_3$;

$R^6$ represents independently for each occurrence H, alkyl aryl, or aralkyl;

$R^7$ represents independently for each occurrence alkyl, aryl, or aralkyl;

$R^8$ represents independently for each occurrence H or alkyl;

n represents independently for each occurrence 0 to 15 inclusive; and

Y represents independently for each occurrence halogen or $R^7CO_2^-$.

In certain embodiments, the present invention relates to the aforementioned compound, wherein $R^2$ is absent, and $R^5$ is H.

In certain embodiments, the present invention relates to the aforementioned compound, wherein $R^1$ is H, $R^2$ is absent, $R^3$ and $R^4$ are —CN, and $R^5$ is H.

Another aspect of the present invention relates to a method of forming a phosphite compound, comprising the steps of:

admixing a phosphoramidite, alcohol, and activating agent to form a phosphite compound, wherein said activating agent is selected from the group consisting of

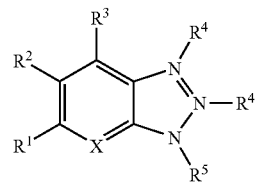

I wherein
X is $C(R^6)$ or N;
$R^1$, $R^2$, $R^3$, and $R^6$ each independently represent H, —$NO_2$, —CN, —$CF_3$, —$SO_2R^8$, —$SR^8$, halogen, alkyl, alkenyl, alkynyl, aryl, aralkyl, alkoxyl, —$OR^7$, —$N(R^7)_2$, —$N(R^7)C(O)R^8$, —$C(O)R^7$, or —$CO_2R^8$; or an instance of $R^1$ and $R^6$, $R^1$ and $R^2$, or $R^2$ and $R^3$ can be taken together for form a 4-8 member ring containing 0-4 heteratoms selected from the group consisting of O, N and S;

$R^4$ is absent or represents independently for each occurrence —$(C(R^9)_2)_nCH_3 \cdot Y$;

$R^5$ is H or —$(C(R^9)_2)_nCH_3$;

$R^7$ represents independently for each occurrence H, alkyl, aryl, or aralkyl;

$R^8$ represents independently for each occurrence alkyl, aryl, or aralkyl;

$R^9$ represents independently for each occurrence H or alkyl;

n represents independently for each occurrence 0 to 15 inclusive; and

Y represents independently for each occurrence halogen or $R^8CO_2^-$;

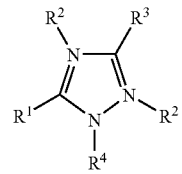

II wherein $R^1$ and $R^3$ each represent independently H, —NO$_2$, —CN, —CF$_3$, —SO$_2$R$^6$, —SR$^6$, halogen, alkyl, alkenyl, alkynyl, aryl, aralkyl, —N(R$^5$)C(O)R$^6$, —C(O)R$^5$, or —CO$_2$R$^6$;

$R^2$ is absent or represents independently for each occurrence —(C(R$^7$)$_2$)$_n$CH$_3$.Y;

$R^4$ is H or —(C(R$^7$)$_2$)$_n$CH$_3$;

$R^5$ represents independently for each occurrence H, alkyl, aryl, or aralkyl;

$R^6$ represents independently for each occurrence alkyl, aryl, or aralkyl;

$R^7$ represents independently for each occurrence H or alkyl;

n represents independently for each occurrence 0 to 15 inclusive; and

Y represents independently for each occurrence halogen or R$^6$CO$_2^-$;

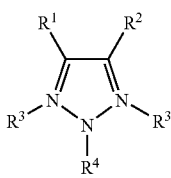

III wherein $R^1$ and $R^2$ each represent independently H, —NO$_2$, —CN, —CF$_3$, —SO$_2$R$^6$, —SR$^6$, halogen, alkyl, alkenyl, alkynyl, aryl, aralkyl, —N(R$^5$)C(O)R$^6$, —C(O)R$^5$, or —CO$_2$R$^6$;

$R^3$ is absent or represents independently for each occurrence —(C(R$^7$)$_2$)$_n$CH$_3$.Y;

$R^4$ is H or —(C(R$^7$)$_2$)$_n$CH$_3$;

$R^5$ represents independently for each occurrence H, alkyl, aryl, or aralkyl;

$R^6$ represents independently for each occurrence alkyl, aryl, or aralkyl;

$R^7$ represents independently for each occurrence H or alkyl;

n represents independently for each occurrence 0 to 15 inclusive; and

Y represents independently for each occurrence halogen or R$^6$CO$_2^-$;

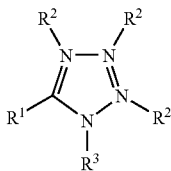

IV wherein $R^1$ is H, —SR$^5$, alkyl, aryl, —N(R$^4$)$_2$, —(R$^4$)$_2$)$_m$CO$_2$R$^5$, —NO$_2$, —CN, —CF$_3$, —SO$_2$R$^5$, —SR$^5$, halogen, alkenyl, alkynyl, aralkyl, —N(R$^4$)C(O)R$^5$, —C(O)R$^4$, or —CO$_2$R$^5$;

$R^2$ is absent or represents independently for each occurrence —(C(R$^6$)$_2$)$_n$CH$_3$.Y;

$R^3$ is H or —(C(R$^6$)$_2$)$_n$CH$_3$;

$R^4$ represents independently for each occurrence H, alkyl, aryl, or aralkyl;

$R^5$ represents independently for each occurrence alkyl, aryl, or aralkyl;

$R^6$ represents independently for each occurrence H or alkyl;

n represents independently for each occurrence 0 to 15 inclusive;

m is 1, 2, 3, 4, 5, 6, 7, or 8; and

Y represents independently for each occurrence halogen or R$^5$CO$_2^-$; and

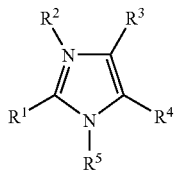

V wherein $R^1$, $R^3$, and $R^4$ each represent independently H, —NO$_2$, —CN, —CF$_3$, —SO$_2$R$^7$, —SR$^7$, halogen, alkyl, alkenyl, alkynyl, aryl, aralkyl, —N(R$^6$)C(O)R$^5$, —C(O)R$^6$, or —CO$_2$R$^7$;

$R^2$ is absent or represents independently for each occurrence —(C(R$^8$)$_2$)$_n$CH$_3$.Y;

$R^5$ is H or —(C(R$^8$)$_2$)$_n$CH$_3$;

$R^6$ represents independently for each occurrence H, alkyl, aryl, or aralkyl;

$R^7$ represents independently for each occurrence alkyl, aryl, or aralkyl;

$R^8$ represents independently for each occurrence H or alkyl;

n represents independently for each occurrence 0 to 15 inclusive; and

Y represents independently for each occurrence halogen or R$^7$CO$_2^-$.

In certain embodiments, the present invention relates to the aforementioned method, wherein said phosphoramidite is a 3'-nucleoside phosphoramidite, 3'-nucleotide phosphoramidite, or 3'-oligonucleotide phosphoramidite.

In certain embodiments, the present invention relates to the aforementioned method, wherein said phosphoramidite is represented by formula A:

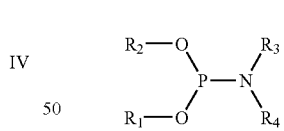

A wherein $R_1$ is alkyl, aryl, aralkyl, or —Si(R$_5$)$_3$; wherein said alkyl, aryl, and aralkyl group is optionally substituted with —CN, —NO$_2$, —CF$_3$, halogen, —O$_2$CR$_5$, or —OSO$_2$R$_5$;

$R_2$ is optionally substituted alkyl, cycloalkyl, heterocycloalkyl, aryl, aralkyl, or alkenyl;

$R_3$ and $R_4$ each represent independently alkyl, cycloalkyl, heterocycloalkyl, aryl, or aralkyl; or $R_3$ and $R_4$ taken together form a 3-8 member ring; and $R_5$ is alkyl, cycloalkyl, heterocycloalkyl, aryl, or aralkyl.

In certain embodiments, the present invention relates to the aforementioned method, wherein $R_1$ is —CH$_2$CH$_2$CN.

In certain embodiments, the present invention relates to the aforementioned method, wherein $R_2$ is an optionally substituted heterocycloalkyl.

In certain embodiments, the present invention relates to the aforementioned method, wherein $R_2$ is an optionally substituted ribose.

In certain embodiments, the present invention relates to the aforementioned method, wherein $R_2$ is an optionally substituted deoxyribose.

In certain embodiments, the present invention relates to the aforementioned method, wherein $R_2$ is a nucleoside or nucleotide.

In certain embodiments, the present invention relates to the aforementioned method, wherein $R_3$ and $R_4$ are alkyl.

In certain embodiments, the present invention relates to the aforementioned method, wherein said alcohol is an optionally substituted ribose.

In certain embodiments, the present invention relates to the aforementioned method, wherein said alcohol is an optionally substituted deoxyribose.

In certain embodiments, the present invention relates to the aforementioned method, wherein alcohol is a nucleoside, nucleotide, or oligonucleotide.

In certain embodiments, the present invention relates to the aforementioned method, wherein said alcohol is represented by $R_5$—OH, wherein $R_5$ is optionally substituted alkyl, cycloalkyl, heterocycloalkyl, aryl, aralkyl, alkenyl, or —(C($R_6$)$_2$)$_p$heterocycloalkyl; $R_6$ is H or alkyl; and p is 1, 2, 3, 4, 5, 6, 7, or 8.

In certain embodiments, the present invention relates to the aforementioned method, wherein $R_5$ is —(C($R_6$)$_2$)$_p$heterocycloalkyl.

In certain embodiments, the present invention relates to the aforementioned method, further comprising the step of admixing a proton-shuttle compound to the mixture comprising said phosphoramidite, said alcohol, and said activating agent, wherein the pKa of said proton-shuttle compound is greater than the pKa of said activating agent, and the pKa of said proton-shuttle compound is less than the pKa of said phosphoramidite.

In certain embodiments, the present invention relates to the aforementioned method, wherein said proton-shuttle compound is a primary, secondary, or tertiary amine.

In certain embodiments, the present invention relates to the aforementioned method, wherein said proton-shuttle compound is represented by N($R_7$)($R_8$)$R_9$, wherein $R_7$, $R_8$, and $R_9$ each represent independently for each occurrence H, alkyl, cycloalkyl, aryl, aralkyl, alkenyl; or $R_7$ and $R_8$ taken together form a 3-8 membered ring; and $R_9$ is H, alkyl, cycloalkyl, aryl, or aralkyl.

Sulfur-transfer Reagents

Modified oligonucleotides are of great value in molecular biological research and in applications such as anti-viral therapy. Modified oligonucleotides which can block RNA translation, and are nuclease resistant, are useful as antisense reagents. Sulfurized oligonucleotides containing phosphorothioate (P=S) linkages are of interest in these areas. Phosphorothioate-containing oligonucleotides are also useful in determining the stereochemical pathways of certain enzymes which recognize nucleic acids.

Standard techniques for sulfinurization of phosphorus-containing compounds have been applied to the synthesis of sulfurized deoxyribonucleotides. Examples of sulfurization reagents which have been used include elemental sulfur, dibenzoyl tetrasulfide, 3-H-1,2-benzidithiol-3-one 1,1-dioxide (also known as Beaucage reagent), tetraethylthiuram disulfide (TETD), and bis(O,O-diisopropoxy phosphinothioyl) disulfide (known as Stec reagent). Most of the known sulfurization reagents, however, have one or more significant disadvantages.

Elemental sulfur presents problems and is not suitable for automation because of its insolubility in most organic solvents. Furthermore, carbon disulfide, a preferred source of sulfur, has undesirable volatility and an undesirably low flash point. Unwanted side products are often observed with the use of dibenzoyl tetrasulfide. The Beaucage reagent, while a relatively efficient sulfurization reagent, is difficult to synthesize and not particularly stable. Furthermore, use of Beaucage reagent forms a secondary reaction product which is a potent oxidizing agent. See R. P. Iyer et al. *J. Am. Chem. Soc.* 1990, 112, 1253-1254 and R. P. Iyer et al. *J Org. Chem.* 1990, 55, 4693-4699. This can lead to unwanted side products which can be difficult to separate from the desired reaction product. Tetraethylthiuram disulfide, while relatively inexpensive and stable, has a sulfurization reaction rate which can be undesirable slow.

A method for producing a phosphorothioate ester by reaction of a phosphite ester with an acyl disulfide is disclosed in Dutch patent application No. 8902521. The disclosed method is applied to a purified phosphotriester dimer utilizing solution-phase chemistry. The method is time and labor intensive in that it was only shown to work in a complex scheme which involved carrying out the first stage of synthesis (formation of a phosphite) in acetonitrile, removing the acetonitrile, purifying the intermediate phosphotriester, and proceeding with the sulfurization in a solvent mixture of dichloroethane (DCE) and 2,4,6-collidine. Furthermore, the method was demonstrated only with a dinucleotide. There was no suggestion that the Dutch method could be employed with larger nucleic acid structures, that the same could employ a common solvent throughout all steps of synthesis, that improved yields could be obtained, or that the method could be adapted for conventional automated synthesis without extensive modification of the scheme of automation. Although acetonitrile is mentioned as one of several possible solvents, utility of the method for carrying out all steps of the synthesis in acetonitrile as a common solvent was not demonstrated. While other publications (Kamer et al. *Tetrahedron Lett.* 1989, 30(48), 6757-6760 and Roelen et al. *Rech. Trav. Chim. Pays-Bas* 1991, 110, 325-331) show sulfurization of oligomers having up to six nucleotides, the aforementioned shortcomings are not overcome by the methods disclosed in these references.

A thioanhydride derivative EDITH (3-ethoxy-1,2,4-dithiazolidine-5-one) is disclosed in U.S. Pat. No. 5,852,168 (the '168 application). Herein we have established that, contrary to expectations, this reagent can be used in the synthesis of 2'-substituted RNA and chimeric RNA. Importantly, even though these reaction conditions are basic they do not result in elimination of the 2'-substitutent or other degradation of the RNA.

Finally, PADS (phenylacetyl disulfide) is disclosed in U.S. Pat. Nos. 6,242,591 and 6,114,519. These patents disclose a methof of sulfurization carried out by contacting a deoxynucleic acid with an acetyl disulfide for a time sufflient to effect formation of a phosphorothioate functional group. However, these patents do not provide examples of such a reaction in the syntheis of RNA (including 2'-substituted RNA and chimeric RNA), as is demonstrated herein. In addition, even though these reaction conditions are basic they do not result in elimination of the 2'-substitutent or other degradation of the RNA.

Thus, the need exists for improved methods and reagents for preparing sulfur-containing phosphorous groups, such as phosphorothioate linkages, in oligonucleotides and other organic compounds. The present invention relates to sulfur-transfer reagents and methods for the formation of phosphorothioates. The methods are amenable to the formation of phosphorothioate linkages in oligonucleotides or derivatives, without the need for complex solvent mixtures, repeated washing, or solvent changes.

Figure 50:
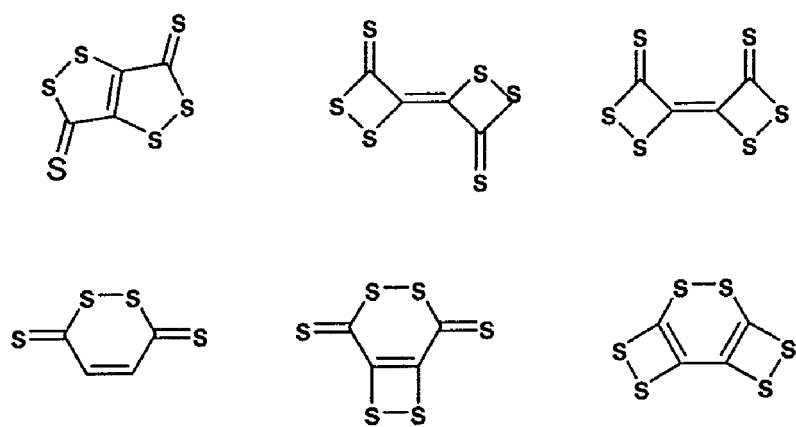
FIG. 50 depicts sulfur-transfer agents useful in preparing phosphorothioate linkages in oligonucleotides.
Figure 51:
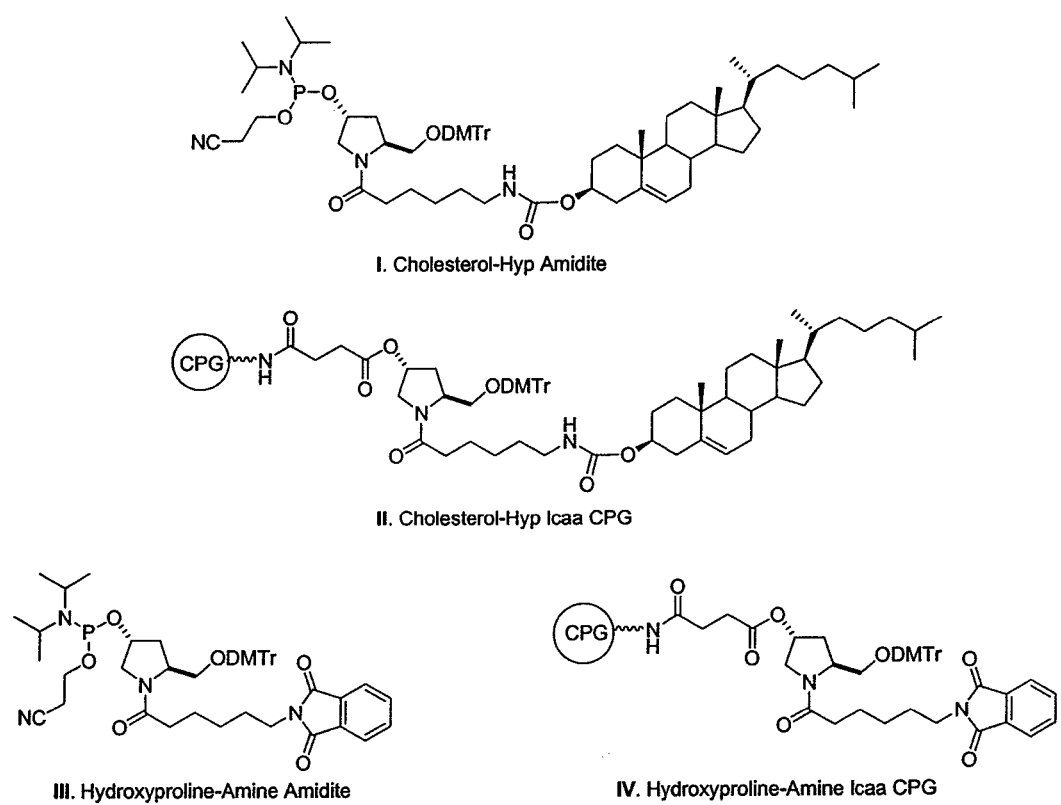
FIG. 51 depicts building blocks for conjugation of cholesteryl- and aminoalkyl-hydroxyprolinol at the 5' and 3'-ends of oligonucleotides. I and III are for 5'-conjugation, and II and IV are for 3'-conjugation. See Example 8.

Certain preferred sulfur-transfer reagents of the invention are presented in FIGS. 4, 5, and 50.

One aspect of the present invention relates to the compound represented by formula D:

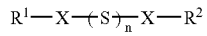
D wherein
X represents independently for each occurrence C(O), C(S), SO$_2$, CO$_2$, CS$_2$, or SO;
R$^1$ and R$^2$ represent independently for each occurrence alkyl, cycloalkyl, aryl, heteroaryl; aralkyl, heteroaralkyl, or —N(R$^3$)R$^4$; or R$^1$ and R$^2$ taken together form an optionally substituted aromatic ring;
R$^3$ is H, alkyl, cycloalkyl, aryl, heteroaryl, aralkyl, or heteroaralkyl;
R$^4$ is H, alkyl, cycloalkyl, aryl, heteroaryl, aralkyl, or heteroaralkyl;
n is 2, 3, or 4; and
provided that when X is C(O), R$^1$ is not benzyl.

In certain embodiments, the present invention relates to the aforementioned compound, wherein n is 2.

In certain embodiments, the present invention relates to the aforementioned compound, wherein R$^1$ and R$^2$ are phenyl, benzyl, cyclohexyl, pyrrole, pyridine, or —CH$_2$-pyridine.

In certain embodiments, the present invention relates to the aforementioned compound, wherein X is C(O), R$^1$ is phenyl, and R$^2$ is phenyl.

In certain embodiments, the present invention relates to the aforementioned compound, wherein X is SO$_2$, R$^1$ is phenyl, and R$^2$ is phenyl.

In certain embodiments, the present invention relates to the aforementioned compound, wherein X is C(O), R$^1$ is pyrrole, and R$^2$ is pyrrole.

In certain embodiments, the present invention relates to the aforementioned compound, wherein X is C(O), and R$^1$ and R$^2$ taken together form a phenyl ring.

Another aspect of the present invention relates to the compound represented by formula D1:

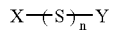
D1 wherein
X is CN, P(OR$^2$)$_2$, P(O)(OR$^2$)$_2$, C(O)R$^1$, C(S)R$^1$, SO$_2$R$^1$, CO$_2$R$^1$, CS$_2$R$^1$, or SOR$^1$;
Y is CN, P(OR$^2$)$_2$, or P(O)(OR$^2$)$_2$;
R$^1$ represents independently for each occurrence alkyl, cycloalkyl, aryl, heteroaryl; aralkyl, heteroaralkyl, or —N(R$^3$)R$^4$;
R$^2$ represents independently for each occurrence H, alkyl, cycloalkyl, aryl, heteroaryl; aralkyl, heteroaralkyl, alkali metal, or transition metal; or two instances of R$^2$ taken together form an alkaline earth metal or transitional metal with an overall charge of +2.
R$^3$ is H, alkyl, cycloalkyl, aryl, heteroaryl, aralkyl, or heteroaralkyl;
R$^4$ is H, alkyl, cycloalkyl, aryl, heteroaryl, aralkyl, or heteroaralkyl; and
n is 2, 3, or 4.

In certain embodiments, the present invention relates to the aforementioned compound, wherein n is 2.

In certain embodiments, the present invention relates to the aforementioned compound, wherein Y is CN.

In certain embodiments, the present invention relates to the aforementioned compound, wherein Y is P(OR$^2$)$_2$.

Another aspect of the present invention relates to the compound represented by formula E:

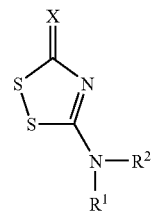
E wherein
X is O or S;
R$^1$ is H, alkyl, cycloalkyl, aryl, heteroaryl, aralkyl, or heteroaralkyl;
R$^2$ is H, alkyl, cycloalkyl, aryl, heteroaryl, aralkyl, heteroaralkyl, —C(O)N(3)R$^4$, —C(S)N(R$^3$)R$^4$, —C(S)N(R$^3$)$_2$, —C(S)OR$^4$, —CO$_2$R$^4$, —C(O)R$^4$, or —C(S)R$^4$;
R$^3$ is H or alkyl; and
R$^4$ is H, alkyl, cycloalkyl, aryl, heteroaryl, aralkyl, or heteroaralkyl.

In certain embodiments, the present invention relates to the aforementioned compound, wherein X is O.

In certain embodiments, the present invention relates to the aforementioned compound, wherein R$^2$ is H, alkyl, or cycloalkyl.

In certain embodiments, the present invention relates to the aforementioned compound, wherein R$^2$ is aryl or aralkyl.

In certain embodiments, the present invention relates to the aforementioned compound, wherein R$^2$ is —C(O)N(R$^3$)R$^4$, —C(S)N(R$^3$)R$^4$, —C(S)N(R$^3$)$_2$, —C(S)OR$^4$, —CO$_2$R$^4$, —C(O)R$^4$, or —C(S)R$^4$.

In certain embodiments, the present invention relates to the aforementioned compound, wherein R$^3$ is H.

In certain embodiments, the present invention relates to the aforementioned compound, wherein R$^4$ is alkyl or aryl.

In certain embodiments, the present invention relates to the aforementioned compound, wherein X is O, and R$^2$ is H.

Another aspect of the present invention relates to a compound formed by the process, comprising the steps of:
admixing about 1 equivalent of chlorocarbonyl sulfenyl chloride, about 1 equivalent of thiourea, and about 1 equivalent of triethylamine in a container cooled with a ice-bath at about 0° C. under an atmosphere of argon, stirring the resultant mixture for about 6 hours, filtering said mixture, concentrating said mixture to give a residue, and recrystallizing said residue from dichloromethane-hexanes to give the compound.

Another aspect of the present invention relates to a method of forming a phosphorothioate compound, comprising the steps of:
admixing a phosphite and a sulfur transfer reagent to form a phosphorothioate, wherein said sulfur transfer reagent is selected from the group consisting of MoS$_4$.Et$_3$NCH$_2$Ph,

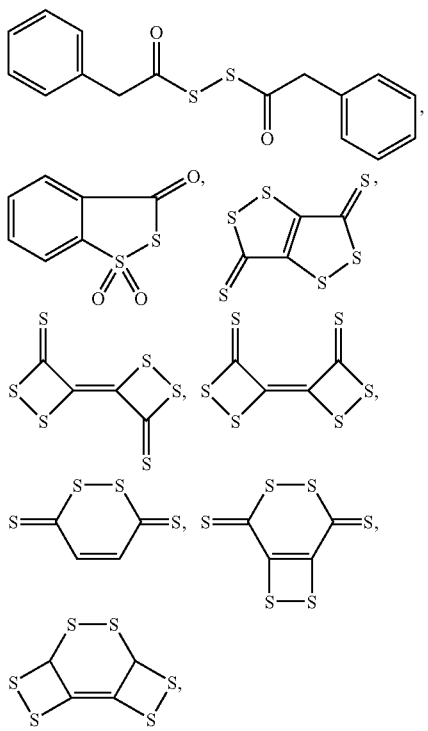

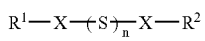

D wherein

X represents independently for each occurrence C(O), C(S), SO$_2$, CO$_2$, CS$_2$, or SO;

R$^1$ and R$^2$ represent independently for each occurrence alkyl, cycloalkyl, aryl, heteroaryl; aralkyl, heteroaralkyl, or —N(R$^3$)R$^4$; or R$^1$ and R$^2$ taken together form an optionally substituted aromatic ring;

R$^3$ is H, alkyl, cycloalkyl, aryl, heteroaryl, aralkyl, or heteroaralkyl;

R$^4$ is H, alkyl, cycloalkyl, aryl, heteroaryl, aralkyl, or heteroaralkyl;

n is 2, 3, or 4; and provided that when X is C(O), R$^1$ is not benzyl;

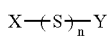

D1 wherein

X is CN, P(OR$^2$)$_2$, P(O)(OR$^2$)$_2$, C(O)R$^1$, C(S)R$^1$, SO$_2$R$^1$, CO$_2$R$^1$, CS$_2$R$^1$, or SOR$^1$;

Y is CN, P(OR$^2$)$_2$, or P(O)(OR$^2$)$_2$;

R$^1$ represents independently for each occurrence alkyl, cycloalkyl, aryl, heteroaryl; aralkyl, heteroaralkyl, or —N(R$^3$)R$^4$;

R$^2$ represents independently for each occurrence H, alkyl, cycloalkyl, aryl, heteroaryl; aralkyl, heteroaralkyl, alkali metal, or transition metal; or two instances of R$^2$ taken together form an alkaline earth metal or transitional metal with an overall charge of +2.

R$^3$ is H, alkyl, cycloalkyl, aryl, heteroaryl, aralkyl, or heteroaralkyl;

R$^4$ is H, alkyl, cycloalkyl, aryl, heteroaryl, aralkyl, or heteroaralkyl; and n is 2, 3, or 4; and

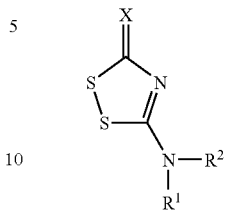

E wherein

X is O or S;

R$^1$ is H, alkyl, cycloalkyl, aryl, heteroaryl, aralkyl, or heteroaralkyl;

R$^2$ is H, alkyl, cycloalkyl, aryl, heteroaryl, aralkyl, heteroaralkyl, —C(O)N(R$^3$)R$^4$, —C(S)N(R$^3$)R$^4$, —C(S)N(R$^3$)$_2$, —C(S)OR$^4$, —CO$_2$R$^4$, —C(O)R$^4$, or —C(S)R$^4$;

R$^3$ is H or alkyl; and

R$^4$ is H, alkyl, cycloalkyl, aryl, heteroaryl, aralkyl, or heteroaralkyl.

In certain embodiments, the present invention relates to the aforementioned method, wherein said phosphite is represented by formula F:

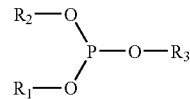

F wherein

R$_1$ is alkyl, aryl, aralkyl, or —Si(R$_4$)$_3$; wherein said alkyl, aryl, and aralkyl group is optionally substituted with —CN, —NO$_2$, —CF$_3$, halogen, —O$_2$CR$_5$, or —OSO$_2$R$_4$;

R$_2$ is optionally substituted alkyl, cycloalkyl, heterocycloalkyl, aryl, aralkyl, or alkenyl;

R$_3$ is optionally substituted alkyl, cycloalkyl, heterocycloalkyl, aryl, aralkyl, alkenyl, or —(C(R$_5$)$_2$)$_p$heterocycloalkyl;

R$_4$ is alkyl, cycloalkyl, heterocycloalkyl, aryl, or aralkyl;

R$_5$ is H or alkyl; and p is 1, 2, 3, 4, 5, 6, 7, or 8.

In certain embodiments, the present invention relates to the aforementioned method, wherein R$_1$ is —CH$_2$CH$_2$CN.

In certain embodiments, the present invention relates to the aforementioned method, wherein R$_2$ is an optionally substituted heterocycloalkyl.

In certain embodiments, the present invention relates to the aforementioned method, wherein R$_2$ is an optionally substituted ribose.

In certain embodiments, the present invention relates to the aforementioned method, wherein R$_2$ is an optionally substituted deoxyribose.

In certain embodiments, the present invention relates to the aforementioned method, wherein R$_2$ is a nucleoside, nucleotide, or oligonucleotide.

In certain embodiments, the present invention relates to the aforementioned method, wherein R$_2$ is

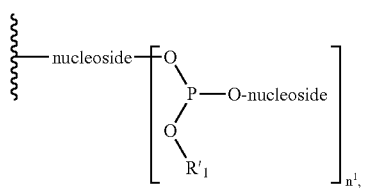

wherein $R'_1$ represents independently for each occurrence alkyl, aryl, aralkyl, or —Si($R_4$)$_3$; wherein said alkyl, aryl, and aralkyl group is optionally substituted with —CN, —NO$_2$, —CF$_3$, or halogen; and $n^1$ is 1 to 50 inclusive.

In certain embodiments, the present invention relates to the aforementioned method, wherein $n^1$ is 1 to 25 inclusive.

In certain embodiments, the present invention relates to the aforementioned method, wherein $n^1$ is 1 to 15 inclusive.

In certain embodiments, the present invention relates to the aforementioned method, wherein $n^1$ is 1 to 10 inclusive.

In certain embodiments, the present invention relates to the aforementioned method, wherein $n^1$ is 1 to 5 inclusive.

Acrylonitrile Quenching Agents

Ethylnitrile is a common phosphate protecting group used in oligonucleotide synthesis. One of the advantages of this protecting group is that it can be easily removed by treating the protected phosphate with a base. The overall transformation is illustrated below.

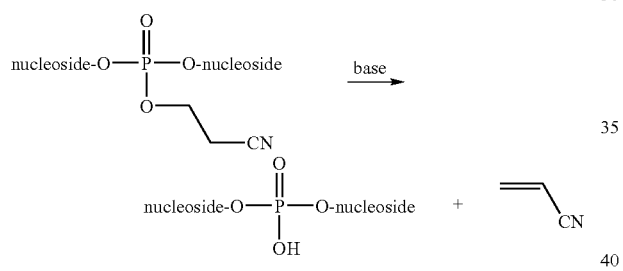

However, the acrylonitrile generated from the deprotection reaction is a good electrophile which can react with nucleophilic functional groups on the desired nucleotide or oligonucleotide product. This side-reaction reduces the yield of the desired product and introduces impurities which can be difficult to remove. Therefore, the need exists for a reagent that will react selectively with the acrylonitrile produced during the deprotection reaction. Representative examples of compounds that would serve as acrylonitrile scavenging agents during the deprotection reaction are polymer-bound thiols, alkane thiol having at least 10 carbon atoms, heteroarylthiol, the sodium salt of an alkane thiol, and thiols that have sufficiently low volitility so that they are odorless, e.g., thiols that have a high molecular weight.

Odorless thiols have been described by K. Nishide and M. Node in *Green Chem.* 2004, 6, 142. Some examples of odorless thiols include dodecanethiol, 4-n-heptylphenylmethanethiol, 4-trimethylsilylphenylmethanethiol, and 4-trimethylsilylbenzenethiol. For additional examples see Development of Odorless Thiols and Sulfides and Their Applications to Organic Synthesis. Nishide, Kiyoharu; Ohsugi, Shin-ichi; Miyamoto, Tetsuo; Kumar, Kamal; Node, Manabu. Kyoto Pharmaceutical University, Misasagi, Yamashina, Kyoto, Japan. *Monatshefte fuer Chemie* 2004, 135(2), 189-200. Benzene thiol and benzyl mercaptan derivatives having only faint odors have been described by Nishide and coworkers. Representative examples include: 4-RC$_6$H$_4$X, 3-RC$_6$H$_4$X and 2-C$_6$H$_4$X (R=Me$_3$Si, Et$_3$Si or Pr$_3$Si; X=SH or CH$_2$SH) See Nishide, Kiyoharu; Miyamoto, Tetsuo; Kumar, Kamal; Ohsugi, Shin-ichi; Node, Manabu of Kyoto Pharmaceutical University, Misasagi, Yamashina, Kyoto, Japan. in "Synthetic Equivalents of Benzenethiol and Benzyl Mercaptan Having Faint Smell: Odor Reducing Effect of Trialkylsilyl Group." *Tetrahedron Lett.* 2002, 43(47), 8569-8573. See Node and coworkers for a description of odorless 1-dodecanethiol. and p-heptylphenylmethanethiol. Node, Manabu; Kumar, Kamal; Nishide, Kiyoharu; Ohsugi, Shin-ichi; Miyamoto, Tetsuo. of Kyoto Pharmaceutical University, Yamashina, Misasagi, Kyoto, Japan. in "Odorless substitutes for foul-smelling thiols: syntheses and applications." *Tetrahedron Lett.* 2001, 42(52), 9207-9210.

Figure 8:
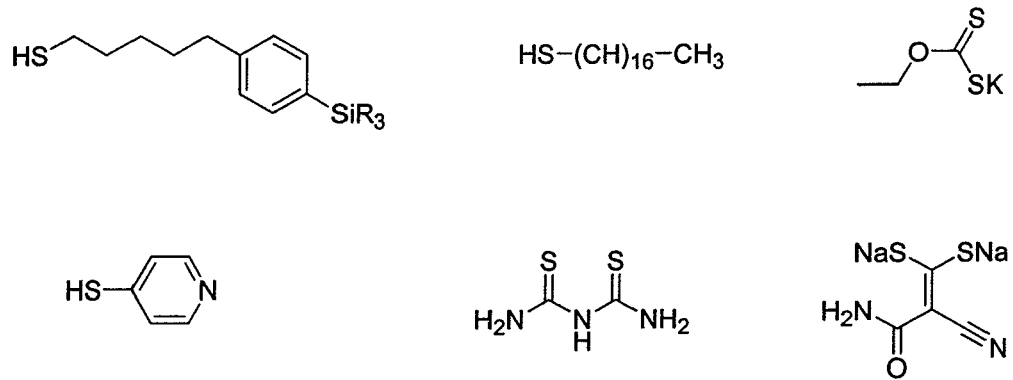
FIG. 8 depicts acrylonitrile quenching agents.

Representative examples of acrylonitrile quenching agents are shown in FIG. 8.

One aspect of the present invention relates to a method of removing an ethylcyanide protecting group, comprising the steps of:

admixing a phosphate compound bearing a ethylcyanide group with a base in the presence acrylonitrile scavenger, wherein said acrylonitrile scavenger is a polymer-bound thiol, 4-n-heptylphenylmethanethiol, alkane thiol having at least 10 carbon atoms, heteroarylthiol, the sodium salt of an alkyl thiol,

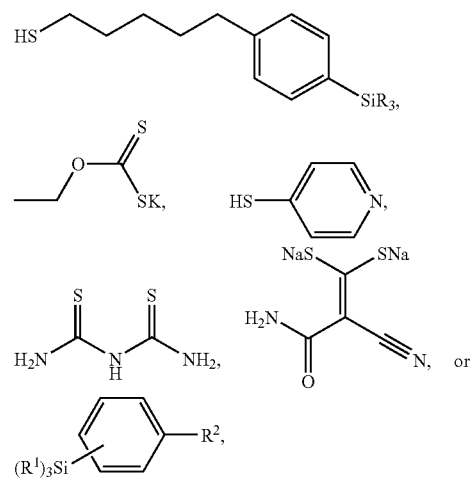

wherein $R^1$ is alkyl; and $R^2$ is —SH, or —CH$_2$SH.

In certain embodiments, the present invention relates to the aforementioned method, wherein said acrylonitrile scavenger is

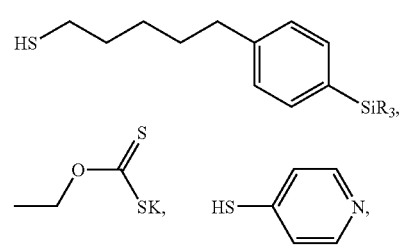

-continued

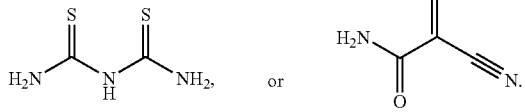

In certain embodiments, the present invention relates to the aforementioned method, wherein said phosphate compound is an oligonucleotide.

In certain embodiments, the present invention relates to the aforementioned method, wherein said phosphate compound is an oligonucleotide containing at least one phosphorothioate group.

In certain embodiments, the present invention relates to the aforementioned method, wherein said phosphate compound is an oligomer of ribonucleotides.

In certain embodiments, the present invention relates to the aforementioned method, wherein said phosphate is represented by formula G:

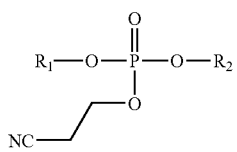

G wherein
$R_1$ is optionally substituted alkyl, cycloalkyl, heterocycloalkyl, aryl, aralkyl, or alkenyl;
$R_2$ is optionally substituted alkyl, cycloalkyl, heterocycloalkyl, aryl, aralkyl, alkenyl, or $-(C(R_3)_2)_p$heterocycloalkyl;
$R_3$ is H or alkyl; and
p is 1, 2, 3, 4, 5, 6, 7, or 8.

In certain embodiments, the present invention relates to the aforementioned method, wherein $R_1$ is an optionally substituted heterocycloalkyl.

In certain embodiments, the present invention relates to the aforementioned method, wherein $R_1$ is an optionally substituted ribose.

In certain embodiments, the present invention relates to the aforementioned method, wherein $R_1$ is an optionally substituted deoxyribose.

In certain embodiments, the present invention relates to the aforementioned method, wherein $R_1$ is a nucleoside, nucleotide, or oligonucleotide.

In certain embodiments, the present invention relates to the aforementioned method, wherein $R_1$ is

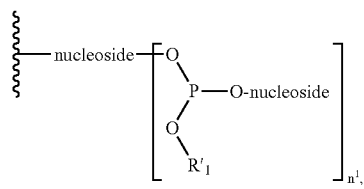

wherein $R'_1$ represents independently for each occurrence alkyl, aryl, aralkyl, or $-Si(R_4)_3$; wherein said alkyl, aryl, and aralkyl group is optionally substituted with $-CN$, $-NO_2$, $-CF_3$, or halogen; $R_4$ is alkyl, aryl, or aralkyl; and $n^1$ is 1 to 50 inclusive.

In certain embodiments, the present invention relates to the aforementioned method, wherein $n^1$ is 1 to 25 inclusive.

In certain embodiments, the present invention relates to the aforementioned method, wherein $n^1$ is 1 to 15 inclusive.

In certain embodiments, the present invention relates to the aforementioned method, wherein $n^1$ is 1 to 10 inclusive.

In certain embodiments, the present invention relates to the aforementioned method, wherein $n^1$ is 1 to 5 inclusive.

Methods for Preserving P=S Bonds

The P=S bond of phosphorothioate nucleotides is sensitive to oxidizing agents, resulting in conversion of the P=S bond to a P=O bond. One aspect of the present invention relates to methods of preventing unwanted oxidation of the P=S bond. One method of preventing unwanted oxidation of the P=S bond is to mix a compound which is more readily oxidized than the P=S bond of a phosphothioate group with the phosphorothioate-containing nucleotide. Examples of compounds that are oxidized more readily than the P=S bond of a phosphothioate group include 2-hydroxylethanethiol, EDTA, vitamin E, thiols including odorless thiols, and vitamin C. Other such compounds can be readily identified by one of ordinary skill in the art by comparing the oxidation potential of the P=S bond of a phosphorothioate to the antioxidant additive. The antioxidant should be oxidized more easily than the P=S bond of the phosphorothioate.

Oxidizing Agents for Preparing P=O Bonds

As described above, oligonucleotides having a phosphorothioate linkage are promising therapeutic agents. In certain instances, it is advantageous to prepare an oligonucleotide having a mixture of phosphate and phosphorothioate linkages. One procedure to prepare oligonucleotides having a mixture of phosphate and phosphorothioate linkages involves attaching a first oligonucleotide to a second oligonucleotide, wherein the first oligonucleotide consists of nucleosides linked via phosphorothioate groups, and the second oligonucleotide consists of nucleosides linked by phosphite groups. Then, the phosphite groups are oxidized to give the phosphate linkage. Alternatively, oligonucleotides can be added sequentially to the first oligonucleotide using the phosphoramide method. Then, the newly added nucleosides, which are linked via phosphite groups, are oxidized to convert the phosphite linkage to a phosphate linkage. One of the most commonly used oxidizing agents for converting a phosphite to a phosphate is $I_2$/amine. Consequently, the $I_2$/amine reagent is a very strong oxidant which also oxidizes phosphorothioates to phosphates. Hence, milder oxidizing agents are needed which will oxidize a phosphite to a phosphate, but will not oxidize a phosphorothioate group. Three examples of oxidizing agents that will oxidize a phosphite to a phosphate, but will not oxidize a phosphorothioate group, are $NaClO_2$, chloroamine, and pyridine-N-oxide. Additional oxidizing agents amenable to the present invention are $CCl_4$, $CCl_4$/water/acetonitrile, $CCl_4$/water/pyridine, dimethyl carbonate, mixture of $KNO_3$/TMSCl in $CH_2Cl_2$, NBS, NCS, or a combination of oxidizing agent, an aprotic organic solvent, a base and water.

One aspect of the present invention relates to a method of oxidizing a phosphite to a phosphate, comprising the steps of:
admixing a phosphite with an oxidizing agent to produce a phosphate, wherein said oxidizing agent is $NaClO_2$, chloroamine, pyridine-N-oxide, $CCl_4$, $CCl_4$/water/acetonitrile, $CCl_4$/water/pyridine, dimethyl carbonate, mixture of $KNO_3$/TMSCl in $CH_2Cl_2$, NBS, or NCS.

In certain embodiments, the present invention relates to the aforementioned method, wherein said oxidizing agent is $NaClO_2$, chloroamine, or pyridine-N-oxide.

In certain embodiments, the present invention relates to the aforementioned method, wherein said phosphite is an oligomer of a nucleoside linked via phosphite groups.

In certain embodiments, the present invention relates to the aforementioned method, wherein said nucleoside is a ribonucleoside.

In certain embodiments, the present invention relates to the aforementioned method, wherein said phosphite is represented by formula H:

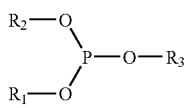

wherein
$R_1$ is alkyl, aryl, aralkyl, or —Si($R_4$)$_3$; wherein said alkyl, aryl, and aralkyl group is optionally substituted with —CN, —NO$_2$, —CF$_3$, halogen, —O$_2$CR$_5$, or —OSO$_2$R$_4$;

$R_2$ is optionally substituted alkyl, cycloalkyl, heterocycloalkyl, aryl, aralkyl, or alkenyl;

$R_3$ is optionally substituted alkyl, cycloalkyl, heterocycloalkyl, aryl, aralkyl, alkenyl, or —(C($R_5$)$_2$)$_p$heterocycloalkyl;

$R_4$ is alkyl, cycloalkyl, heterocycloalkyl, aryl, or aralkyl;

$R_5$ is H or alkyl; and p is 1, 2, 3, 4, 5, 6, 7, or 8.

In certain embodiments, the present invention relates to the aforementioned method, wherein $R_1$ is —CH$_2$CH$_2$CN.

In certain embodiments, the present invention relates to the aforementioned method, wherein $R_2$ is an optionally substituted heterocycloalkyl.

In certain embodiments, the present invention relates to the aforementioned method, wherein $R_2$ is an optionally substituted ribose.

In certain embodiments, the present invention relates to the aforementioned method, wherein $R_2$ is an optionally substituted deoxyribose.

In certain embodiments, the present invention relates to the aforementioned method, wherein $R_2$ is a nucleoside, nucleotide, or oligonucleotide.

In certain embodiments, the present invention relates to the aforementioned method, wherein $R_2$ is

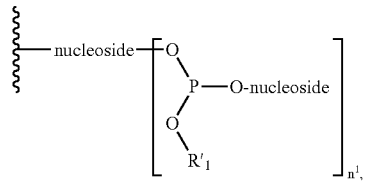

wherein R'$_1$ represents independently for each occurrence alkyl, aryl, aralkyl, or —Si(R$_4$)$_3$; wherein said alkyl, aryl, and aralkyl group is optionally substituted with —CN, —NO$_2$, —CF$_3$, or halogen; and n$^1$ is 1 to 50 inclusive.

In certain embodiments, the present invention relates to the aforementioned method, wherein n$^1$ is 1 to 25 inclusive.

In certain embodiments, the present invention relates to the aforementioned method, wherein n$^1$ is 1 to 15 inclusive.

In certain embodiments, the present invention relates to the aforementioned method, wherein n$^1$ is 1 to 10 inclusive.

In certain embodiments, the present invention relates to the aforementioned method, wherein n$^1$ is 1 to 5 inclusive.

Agents for the Deprotection/Cleavage of Protecting Groups

RNA is often synthesized and purified by methodologies based on: tetrazole to activate the RNA amidite, NH$_4$OH to remove the exocyclic amino protecting groups, n-tetrabutylammonium fluoride (TBAF) to remove the 2'-OH alkylsilyl protecting groups, and gel purification and analysis of the deprotected RNA. The RNA compounds may be formed either chemically or using enzymatic methods.

One important component of oligonucleotide synthesis is the installation and removal of protecting groups. Incomplete installation or removal of a protecting group lowers the overall yield of the synthesis and introduces impurities that are often very difficult to remove from the final product. In order to obtain a reasonable yield of a large RNA molecule (i.e., about 20 to 40 nucleotide bases), the protection of the amino functions of the bases requires either amide or substituted amide protecting groups. The amide or substituted amide protecting groups must be stable enough to survive the conditions of synthesis, and yet removable at the end of the synthesis. These requirements are met by the following amide protecting groups: benzoyl for adenosine, isobutyryl or benzoyl for cytidine, and isobutyryl for guanosine. The amide protecting groups are often removed at the end of the synthesis by incubating the RNA in NH$_3$/EtOH or 40% aqueous MeNH$_2$. In the case of the phenoxyacetyl type protecting groups on guanosine and adenosine and a cetyl protecting groups on cytidine, an incubation in ethanolic ammonia for 4 h at 65° C. is used to obtain complete removal of these protecting groups. However, deprotection procedures using mixtures of NH$_3$ or MeNH$_2$ are complicated by the fact that both ammonia and methylamine are corrosive gases. Therefore, handling the reagents can be dangerous, particulary when the reaction is conducted at a large scale, e.g, manufacturing scale. The volatile nature of NH$_3$ and MeNH$_2$ also requires special procedures to capture and neutralize any excess NH$_3$ and MeNH$_2$ once the deprotection reaction is complete. Therefore, the need exists for less volatile reagents that are capable of effecting the amide deprotection reaction in high yield.

One aspect of the present invention relates to amino compounds with relatively low volatility capable of effecting the amide deprotection reaction. The classes of compounds with the aforementioned desirable characteristics are listed below. In certain instances, preferred embodiments within each class of compounds are listed as well.

1) Polyamines

The polyamine compound used in the invention relates to polymers containing at least two amine functional groups, wherein the amine functional group has at least one hydrogen atom. The polymer can have a wide range of molecular weights. In certain embodiment, the polyamine compound has a molecular weight of greater than about 5000 g/mol. In other embodiments, the polyamine compound compound has a molecular weight of greater than about 10,000; 20,000; or 30,000 g/mol.

2) PEHA

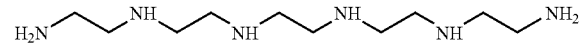

3) PEG-NH$_2$

The PEG-NH$_2$ compound used in the invention relates to polyethylene glycol polymers comprising amine functional groups, wherein the amine functional group has at least one hydrogen atom. The polymer can have a wide range of molecular weights. In certain embodiment, the PEG-NH$_2$ compound has a molecular weight of greater than about 5000 g/mol. In other embodiments, the PEG-NH$_2$ compound has a molecular weight of greater than about 10,000; 20,000, or 30,000 g/mol.

4) Short PEG-NH$_2$

The short PEG-NH$_2$ compounds used in the invention relate to polyethylene glycol polymers comprising amine functional groups, wherein the amine functional group has at least one hydrogen atom. The polymer has a relatively low molecular weight range.

5) Cycloalkylamines and Hydroxycycloalkyl Amines

The cycloalkylamines used in the invention relate to cycloalkyl compounds comprising at least one amine functional group, wherein the amine functional group has at least one hydrogen atom. The hydroxycycloalkyl amines used in the invention relate to cycloalkyl compounds comprising at least one amine functional group and at least one hydroxyl functional group, wherein the amine functional group has at least one hydrogen atom. Representative examples are listed below.

 

6) Hydroxyamines

The hydroxyamines used in the invention relate to alkyl, aryl, and aralkyl compounds comprising at least one amine functional group and at least one hydroxyl functional group, wherein the amine functional group has at least one hydrogen atom. Representative examples are 9-aminononanol, 4-aminophenol, and 4-hydroxybenzylamine.

7) K$_2$CO$_3$/MeOH with or without Microwave
8) Cysteamine (H$_2$NCH$_2$CH$_2$SH) and Thiolated Amines
9) β-Amino-ethyl-sulfonic Acid, or the Sodium Sulfate of β-amino-ethyl-sulfonic Acid One aspect of the present invention relates to a method of removing an amide protecting group from an oligonucleotide, comprising the steps of:

admixing an oligonucleotide bearing an amide protecting group with a polyamine, PEHA, PEG-NH$_2$, Short PEG-NH$_2$, cycloalkyl amine, hydroxycycloalkyl amine, hydroxyamine, K$_2$CO$_3$/MeOH microwave, thioalkylamine, thiolated amine, β-amino-ethyl-sulfonic acid, or the sodium sulfate of β-amino-ethyl-sulfonic acid.

In certain embodiments, the present invention relates to the aforementioned method, wherein said oligonucleotide is an oligomer of ribonucleotides.

Reagents for Deprotection of a Silyl Group

As described in the previous section, the use of protecting groups is a critical component of oligonucleotide synthesis. Furthermore, the installation and removal of protecting groups must occur with high yield to minimize the introduction of impurities into the final product. The Applicants have found that the following reagents are superior for removing a silyl protecting group during the synthesis of a oligonucleotide: pyridine-HF, DMAP-HF, urea-HF, ammonia-HF, ammonium fluoride-HF, TSA-F, DAST, and polyvinyl pyridine-HF. For example, see FIG. 7 and Example 5. Other aryl amine-HF reagents useful in this invention include compounds represented by AA:

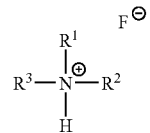

AA wherein
R$^1$ is alkyl, aryl, heteroaryl, aralkyl or heteroaralkyl;
R$^2$ is alkyl, aryl, heteroaryl, aralkyl or heteroaralkyl; and
R$^3$ is aryl or heteroaryl.

For example, aryl amines of the hydrofluoride salts are selected from the group consisting of (dialkyl)arylamines, (alkyl)diarylamines, (alkyl)(aralkyl)arylamines, (diaralkyl)arylamines, (dialkyl)heteroarylamines, (alkyl)diheteroarylamines, (alkyl)(heteroaryl)arylamines, (alkyl)(heteroaralkyl)arylamines, (alkyl)(aralkyl)heteroarylamines, (diaralkyl)heteroarylamines, (diheteroaralkyl)heteroarylamines, and (aralkyl)(heteroaralkyl)heteroarylamines.

In addition, the aforementioned methods can be practised with a hydrofluoride salt of a compound selected from the group consisting of

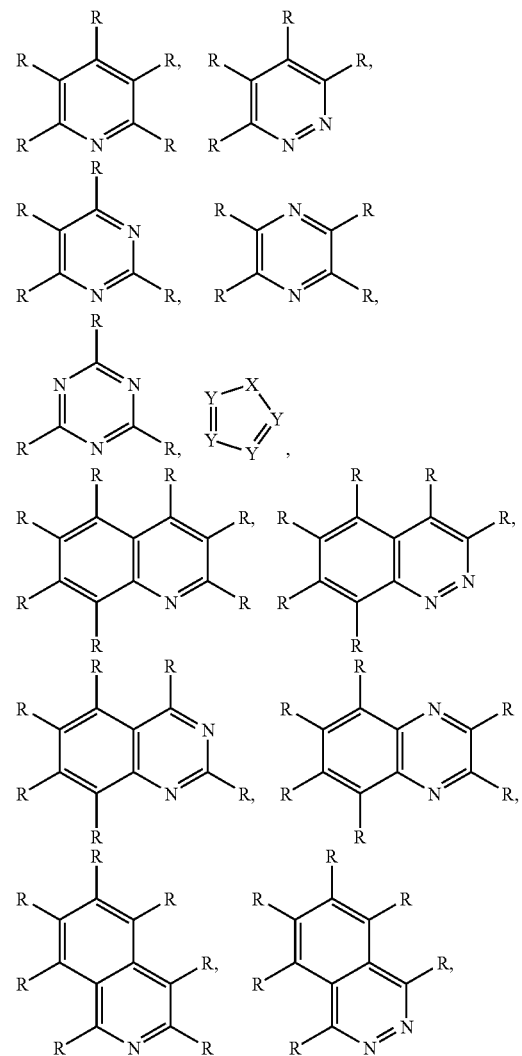

-continued

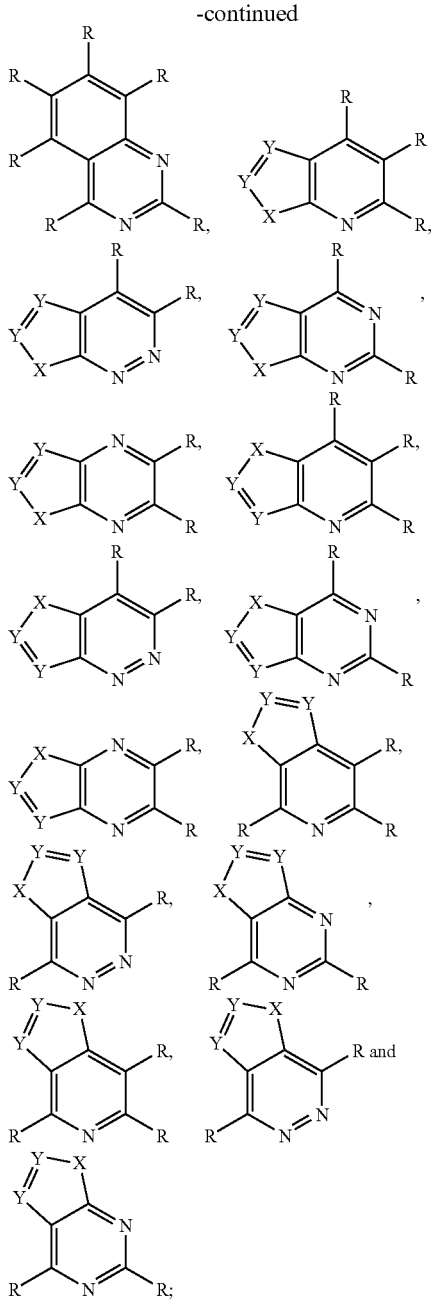

wherein, independently for each occurrence: X is O, S, $NR^1$ or $CR_2$; Y is N or CR; R is hydrogen, halogen, alkyl, cycloalkyl, heterocycloalkyl, aryl, heteroaryl, aralkyl, heteroaralkyl, —C(═O)—, —C(═O)X—, —$OR^1$, —$N(R^1)_2$, —$SR^1$ or —$(CH_2)_m$—$R^1$; $R^1$ is hydrogen, halogen, alkyl, cycloalkyl, heterocycloalkyl, aryl, heteroaryl, aralkyl or heteroaralkyl; and m is 0-10 inclusive.

In certain instances, the rate of the deprotection reaction can be excelerated by conducting the deprotection reaction in the presence of microwave radiation. As illustrated in Example 6, the tert-butyldimethylsilyl groups on a 10-mer or 12-mer could be removed in 2 minutes or 4 minutes, respectively, by treatment with 1 M TBAF in THF, $Et_3N$—HF, or pyridine-HF/DBU in the presence of microwave radiation (300 Watts, 2450 MHz).

One aspect of the present invention relates to a method removing a silyl protecting group from a oligonucleotide, comprising the steps of:

admixing an oligonucleotide bearing a silyl protecting group with pyridine-HF, DMAP-HF, Urea-HF, TSA-F, DAST, polyvinyl pyridine-HF, or an aryl amine-HF reagent of formula AA:

AA wherein
$R^1$ is alkyl, aryl, heteroaryl, aralkyl or heteroaralkyl;
$R^2$ is alkyl, aryl, heteroaryl, aralkyl or heteroaralkyl; and
$R^3$ is aryl or heteroaryl.

In certain embodiments, the present invention relates to the aforementioned method, wherein said oligonucleotide is an oligomer of ribonucleotides.

In certain embodiments, the present invention relates to the aforementioned method, wherein the reaction is carried out in the presence of microwave radiation.

Solid Supports for Oligonucleotide Synthesis

Solid-phase oligonucleotide synthesis is often performed on controlled pore glass. However, solid-phase oligonucleotide synthesis can be carried out on:
1) Fractosil
2) Non CPG, but silica based solid supports not including controlled pore glass
3) Universal linker on polystyrene beads.
4) Argogel
5) Argopore
6) AM Polystyrene
7) Novagel
8) PEGA; EM Merck poly(vinyl alcohol) (PVA); and Nitto Denko polystyrene Experiments conducted using ArgoGel (dT succinate loaded on the support, loading=229.35 µmole/g) revealed that Poly-T synthesis was quite good. However, the material can be sticky leading to difficulties when weighing and loading the column.

Experiments conducted using Argopore-1 (dT succinate loaded on the support, loading=322.14 µmole/g) revealed that the material exhibited good flow through, and the material was not sticky. However, the synthesis coupling efficiency was reduced after 4-5 couplings.

Experiments conducted using Argopore-2 (dT succinate loaded on the support, loading=194 µmole/g) revealed that Poly-T synthesis was quite good.

Linkers to Solid Supports

The oligonucleotide is generally attached to the solid support via a linking group. Suitable linking groups are an oxalyl linker, succinyl, dicarboxylic acid linkers, glycolyl linker, or thioglycolyl linker. Silyl linkers can also be used. See, e.g., DiBlasi, C. M.; Macks, D. E.; Tan, D. S. "An Acid-Stable tert-Butyldiarylsilyl (TBDAS) Linker for Solid-Phase Organic Synthesis" Org. Lett. 2005; ASAP Web Release Date: 30 Mar. 2005; (Letter) DOI: 10.1021/ol050370y. DiBlasi et al. describe a robust tert-butyldiarylsilyl (TBDAS) linker for solid-phase organic synthesis. Importantly, the TBDAS linker is stable to aqueous HF in $CH_3CN$, which allows for the use of orthogonal HF-labile protecting groups in solid-phase synthetic schemes. In one approach, they established that cleavage of the linker could be achieved with tris(dimethylamino)-sulfonium (trimethylsilyl)-difluoride (TAS-F).

Solvents

In response to the growing emphasis on conducting reactions in solvents that are more environmentally friendly, we have found that oligonucleotides can be prepared using non-halogenated solvents. For example, oligonucleotides can be prepared using toluene, tetrahydrofuran, or 1,4-dioxane as the solvent.

RNA Synthesis via H-Phosphonate Coupling

Synthesis of RNA using the H-phosphonate coupling method involves reacting a nucleoside substituted with an H-phosphonate with the hydroxyl group of a second nucleoside in the presence of an activating agent. One of the most commonly used activating agents is pivaloyl chloride. However, pivaloyl chloride is not ideal for large-scale preparations because it is flammable, corrosive, volatile (bp 105-106° C.), and has a relatively low flashpoint (Fp 8° C.). Therefore, the need exists for new activating agents devoid of the aforementioned drawbacks.

There are currently many useful condensing reagents known to the art skilled that are amenable to the H-phosphonate method of oligonucleotide synthesis. See Wada et al. *J. Am. Chem. Soc.* 1997, 119, 12710-12721. Useful condensing reagents include acid chlorides, chlorophosphates, carbonates, carbonium type compounds and phosphonium type compounds. In a preferred embodiment the condensing reagent is selected from a group consisting of pivaloyl chloride, adamantyl chloride, 2,4,6-triisopropyl-benzenesulfonyl chloride, 2-chloro-5,5-dimethyl-2-oxo-1,3,2-dioxaphosphinane, diphenyl phosphorochloridate, bis(2-oxo-3-oxazolidinyl)phosphinic chloride, bis(pentafluorophenyl)carbonate, 2-(1H-benzotriazole-1-yl)-1,1,3,3-tetramethyluronium hexafluorophosphate, O-(azabenzotriazol-1-yl)-1,1,3,3-tetramethyl uronium hexafluorophosphate, 6-(trifluoromethyl)benzotriazol-1-yl-oxy-tris-pyrrolidino-phosphonium hexafluorophosphate, bromo-tris-pyrrolidino-phosphonium hexafluorophosphate, benzotriazole-1-yl-oxy-tris-pyrrolidino-phosphonium hexafluorophosphate and 2-(benzotriazol-1-yloxy)-1,3-dimethyl-2-pyrrolidin-1-yl-1,3,2-diazaphospholidinium hexafluorophosphate. Additionally, 2-chloro-5,5-dimethyl-2-oxo-1,3,2-dioxaphosphinanane, NEP-Cl/pyridine/MeCN system has been described. See U.S. Pat. No. 6,639,061.

The Applicants disclose herein other activating agents that can be used in the H-phosphonate coupling method. Classes of compound that are better activating agents include acid chlorides of long-chain alkyl groups, acid chlorides of aromatic groups, acid chlorides of alkyl groups substituted with aromatic groups, and polymer bound acyl chlorides. Representative examples of activiting agents are decanoyl chloride, dodecanoyl chloride, benzoyl chloride, 1,2-dibenzyl ethanoyl chloride, naphthoyl chloride, anthracenecarbonyl chloride, and fluorenecarbonyl chloride.

The Applicants disclose herein other oxidizing agents that can be used in the H-phosphonate coupling method. One of the most common oxidizing agents is iodine. However, iodine is a very strong oxidizing agent that can lead to unwanted oxidation of sensitive functional groups on the nucleotide or oligonucleotide. Representative examples of oxidizing agents that can be used in the H-phosphonate coupling method include: camphorylsulfonyloxaziridine and N,O-bis(trimethylsilyl)-acetamide in MeCN/pyridine, CCl₄/pyridine/water/MeCN, and DMAP in pyridine/CCl₄/water.

Another aspect of the present invention relates to a method of forming a phosphodiester compound, comprising the steps of:

admixing a H-phosphonate, alcohol, and activating agent to form a phosphodiester compound, wherein said activating agent is selected from the group consisting of $C_8$-$C_{20}$ alkylcarbonyl chloride, arylcarbonyl chloride, and aralkylcarbonyl chloride.

In certain embodiments, the present invention relates to the aforementioned method, wherein said activating agent is decanoyl chloride, dodecanoyl chloride, benzoyl chloride, 1,2-dibenzyl ethanoyl chloride, naphthoyl chloride, anthracenecarbonyl chloride, or fluorenecarbonyl chloride.

In certain embodiments, the present invention relates to the aforementioned method, wherein said H-phosphonate is represented by formula I:

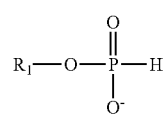

wherein $R_1$ is optionally substituted alkyl, cycloalkyl, heterocycloalkyl, aryl, aralkyl, or alkenyl.

In certain embodiments, the present invention relates to the aforementioned method, wherein $R_1$ is an optionally substituted heterocycloalkyl.

In certain embodiments, the present invention relates to the aforementioned method, wherein $R_1$ is an optionally substituted ribose.

In certain embodiments, the present invention relates to the aforementioned method, wherein $R_1$ is an optionally substituted deoxyribose.

In certain embodiments, the present invention relates to the aforementioned method, wherein $R_1$ is a nucleoside or nucleotide.

In certain embodiments, the present invention relates to the aforementioned method, wherein said alcohol is an optionally substituted ribose.

In certain embodiments, the present invention relates to the aforementioned method, wherein said alcohol is an optionally substituted deoxyribose.

In certain embodiments, the present invention relates to the aforementioned method, wherein said alcohol is a nucleoside, nucleotide, or oligonucleotide.

In certain embodiments, the present invention relates to the aforementioned method, wherein said alcohol is represented by $R_5$—OH, wherein $R_5$ is optionally substituted alkyl, cycloalkyl, heterocycloalkyl, aryl, aralkyl, alkenyl, or —(C($R_6$)$_2$)$_p$heterocycloalkyl; $R_6$ is H or alkyl; and p is 1, 2, 3, 4, 5, 6, 7, or 8.

In certain embodiments, the present invention relates to the aforementioned method, wherein said phosphodiester is represented by formula J:

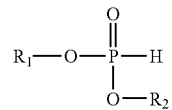

wherein

R₁ is optionally substituted alkyl, cycloalkyl, heterocycloalkyl, aryl, aralkyl, or alkenyl; and R₂ is optionally substituted alkyl, cycloalkyl, heterocycloalkyl, aryl, aralkyl, alkenyl, or —$(C(R_6)_2)_p$heterocycloalkyl; $R_6$ is H or alkyl; and p is 1, 2, 3, 4, 5, 6, 7, or 8.

In certain embodiments, the present invention relates to the aforementioned method, wherein $R_1$ is an optionally substituted heterocycloalkyl.

In certain embodiments, the present invention relates to the aforementioned method, wherein $R_1$ is an optionally substituted ribose.

In certain embodiments, the present invention relates to the aforementioned method, wherein $R_1$ is an optionally substituted deoxyribose.

In certain embodiments, the present invention relates to the aforementioned method, wherein $R_1$ is a nucleoside or nucleotide.

In certain embodiments, the present invention relates to the aforementioned method, wherein $R_2$ is $(C(R_6)_2)_p$heterocycloalkyl.

In certain embodiments, the present invention relates to the aforementioned method, wherein $R_2$ is an optionally substituted ribose.

In certain embodiments, the present invention relates to the aforementioned method, wherein $R_2$ is an optionally substituted deoxyribose.

In certain embodiments, the present invention relates to the aforementioned method, wherein $R_2$ is a nucleoside or nucleotide.

Purification of Double-Stranded RNA

One common problem encountered in RNA preparation is obtaining the desired oligonucleotide in high purity. In many cases, reactions used to prepare the oligonucleotide do not achieve 100% conversion, or they generate side-products. Unfortunately, the unreacted starting materials and side-products often have similar chemical properties, making it very difficult to separate the desired product from these impurities.

The most quantitative procedure for recovering a fully deprotected RNA molecule is by either ethanol precipitation, or an anion exchange cartridge desalting, as described in Scaringe et al. *Nucleic Acids Res.* 1990, 18, 5433-5341. Purification of long RNA sequences is often performed using a two-step chromatographic procedure in which the molecule is first purified on a reverse phase column with either the trityl group at the 5' position on or off. This purification is carried out using an acetonitrile gradient with triethylammonium or bicarbonate salts as the aqueous phase. In the case where the trityl group is still attached to the RNA during purification, the trityl group may be removed by the addition of an acid and drying of the partially purified RNA molecule. The final purification is carried out on an anion exchange column, using alkali metal perchlorate salt gradients to elute the fully purified RNA molecule as the appropriate metal salts, e.g. Na⁺, Li⁺ etc. A final de-salting step on a small reverse-phase cartridge completes the purification procedure.

In certain instances, purification of long RNA molecules is carried out using anion exchange chromatography, particularly in conjunction with alkali perchlorate salts. This system is used to purify very long RNA molecules. In particular, it is advantageous to use a Dionex NUCLEOPAK 100® or a Pharmacia MONO Q® anion exchange column for the purification of RNA by the anion exchange method. This anion exchange purification may be used following a reverse-phase purification or prior to reverse-hase purification. This method results in the formation of a sodium salt of the ribozyme during the chromatography. Replacement of the sodium alkali earth salt by other metal salts, e.g., lithium, magnesium or calcium perchlorate, yields the corresponding salt of the RNA molecule during the purification.

In the case of the two-step purification procedure wherein the first step is a reverse-phase purification followed by an anion exchange step, the reverse-phase purification is usually performed using polymeric, e.g., polystyrene based, reverse-phase media using either a 5'-trityl-on or 5'-trityl-off method. Either molecule may be recovered using this reverse-phase method, and then, once detritylated, the two fractions may be pooled and submitted to an anion exchange purification step as described above.

However, many synthetic RNA products still contain substantial quantities of impurities despite performing the arduous purification steps, as described above. Therefore, the need exists for a new purification procedure to provide RNA in a highly pure form.

Figure 11:
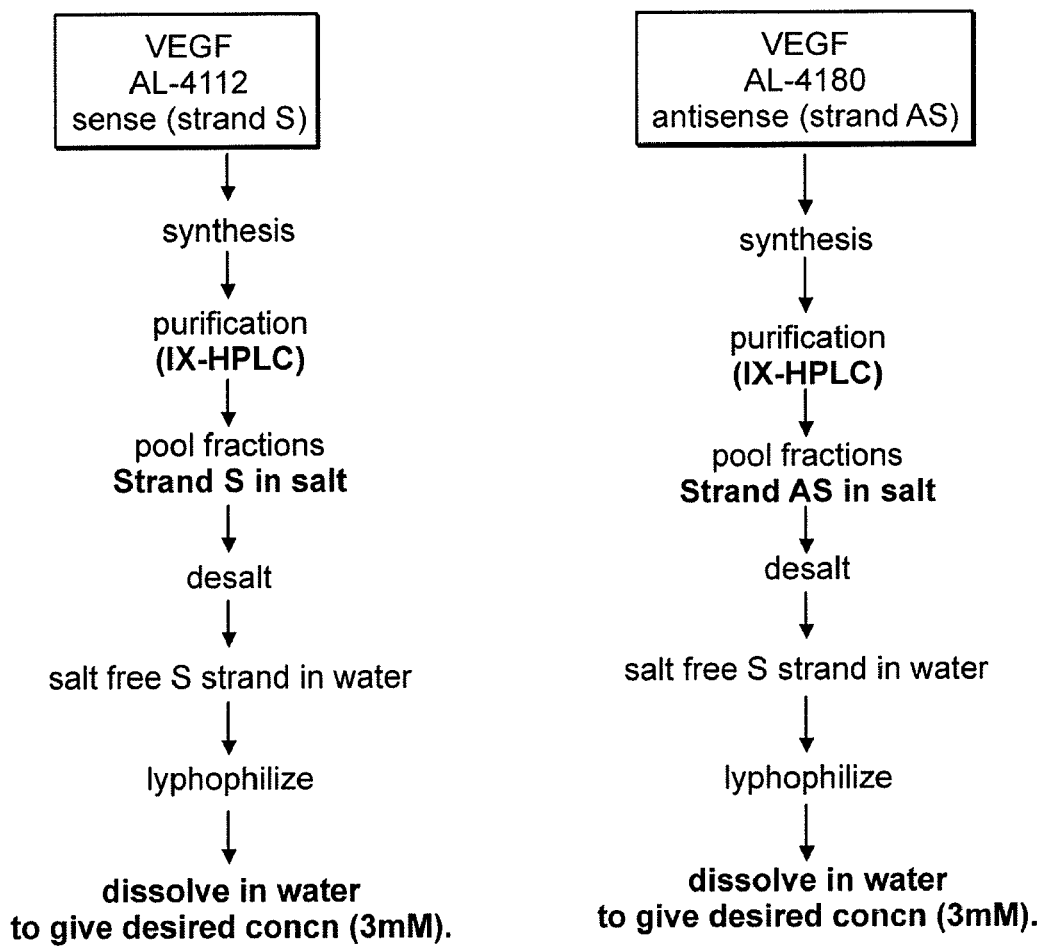
FIG. 11 depicts the first part of the two-strand approach to purification of AL-DP-4014, the components of which are AL-4112 and AL-4180.
Figure 12:
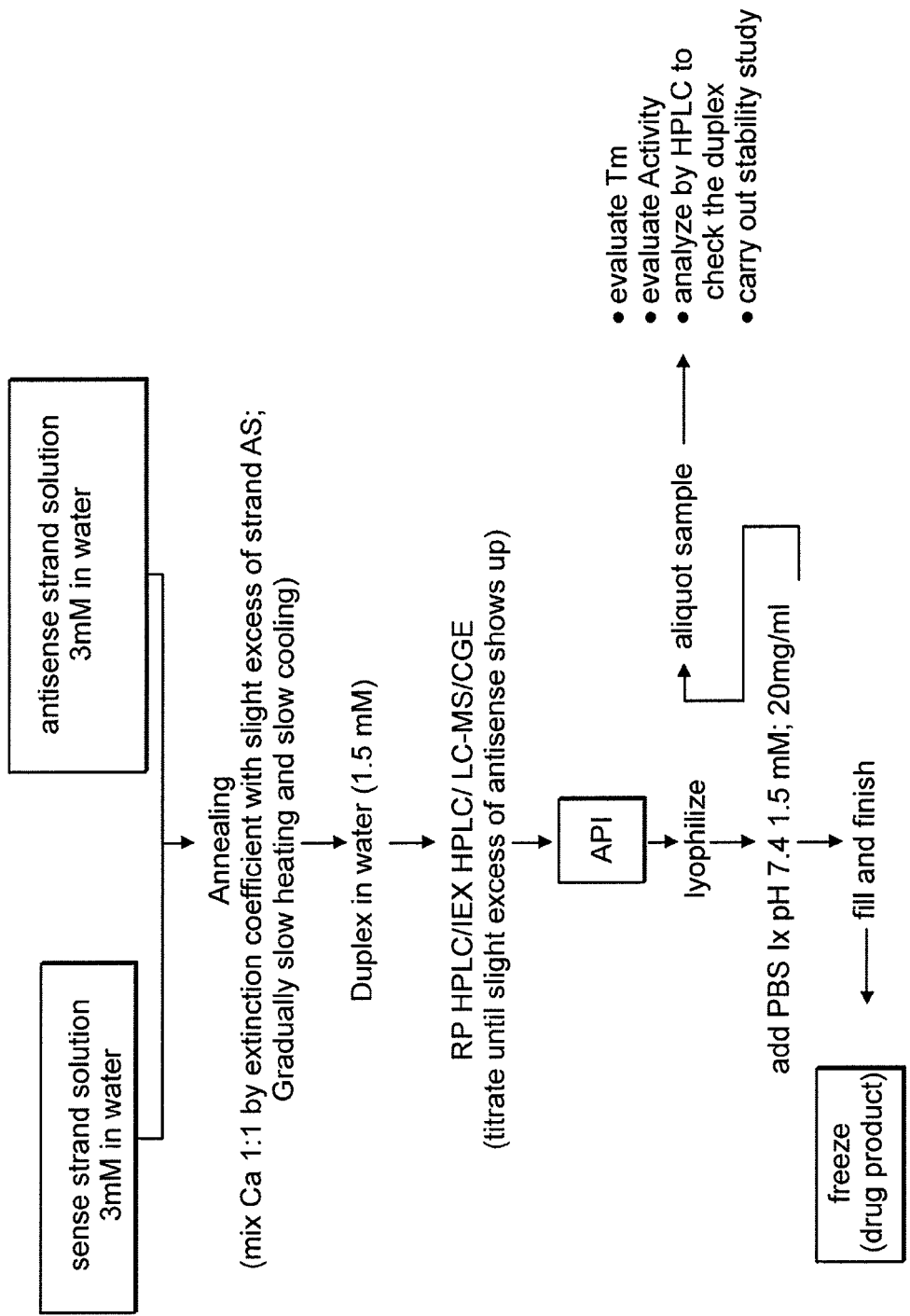
FIG. 12 depicts the second part of the two-strand approach to purification of AL-DP-4014, the components of which are AL-4112 and AL-4180. Note: RP HPLC indicates reverse phase high-performance liquid chromatographic analysis. IEX HPLC indicates ion exchange high-performance liquid chromatographic analysis.
Figure 13:
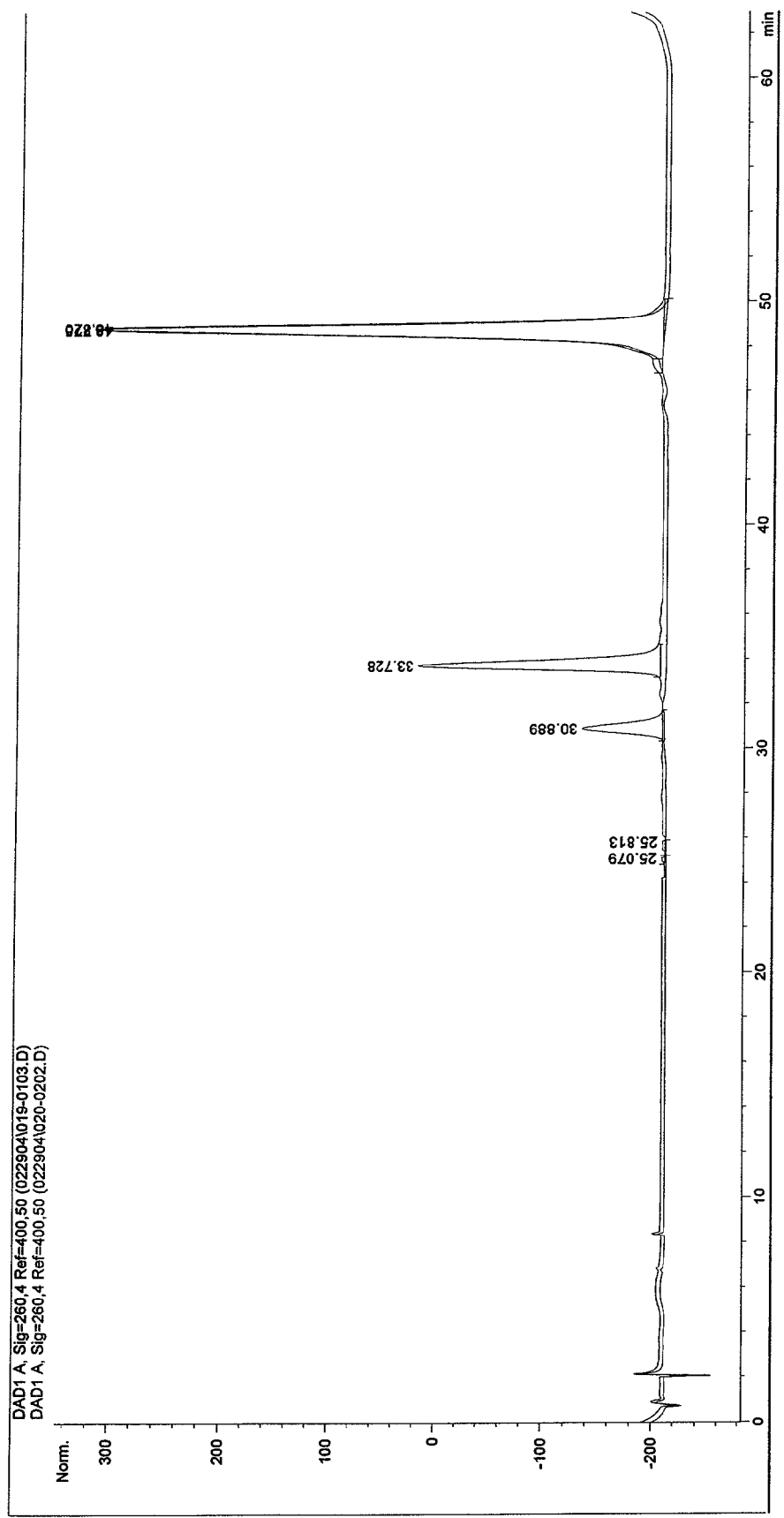
FIG. 13 depicts a reverse phase HPLC chromatogram of AL-DP-4014.
Figure 14:
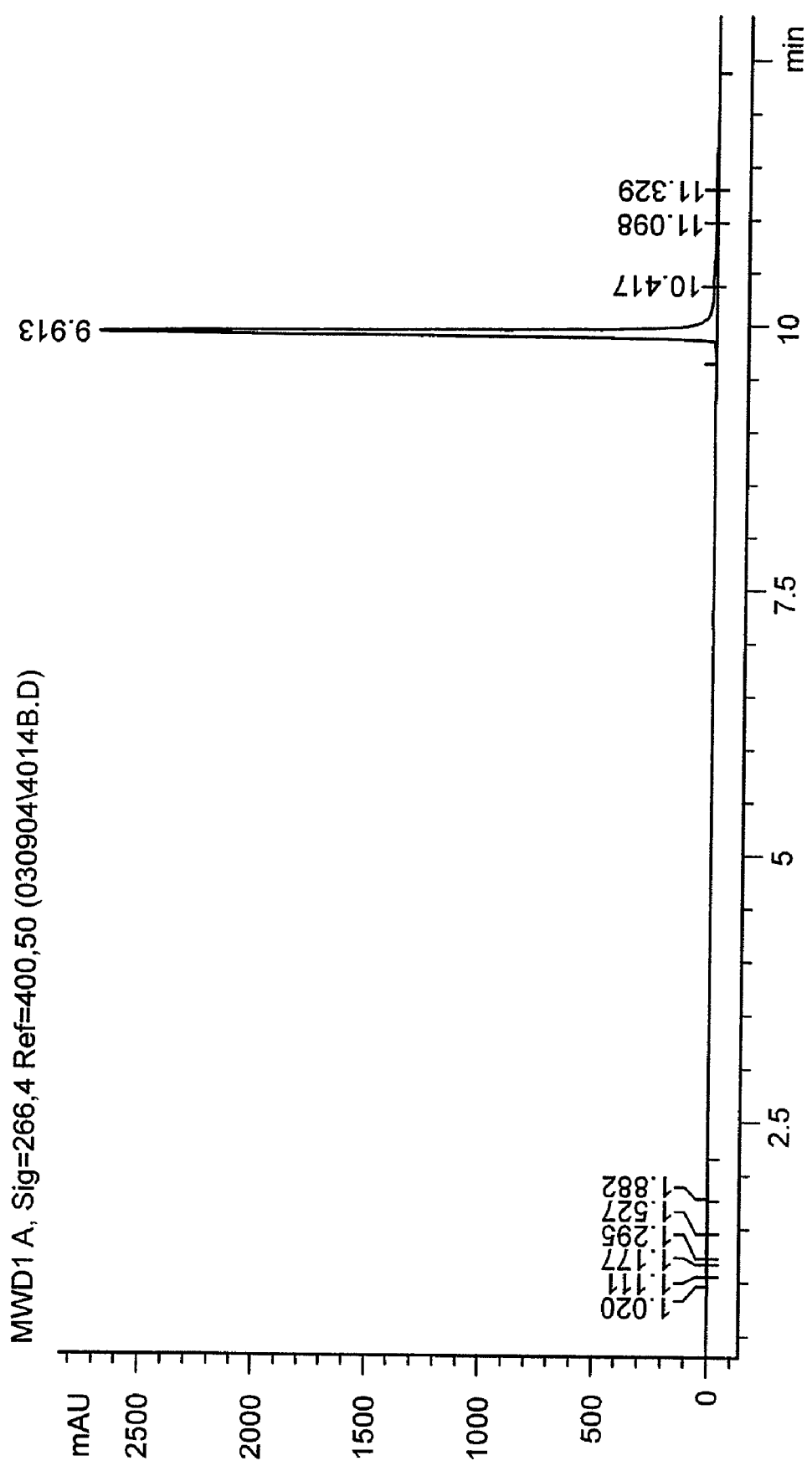
FIG. 14 depicts a LC-MS chromatogram of AL-DP-4014.
Figure 15:
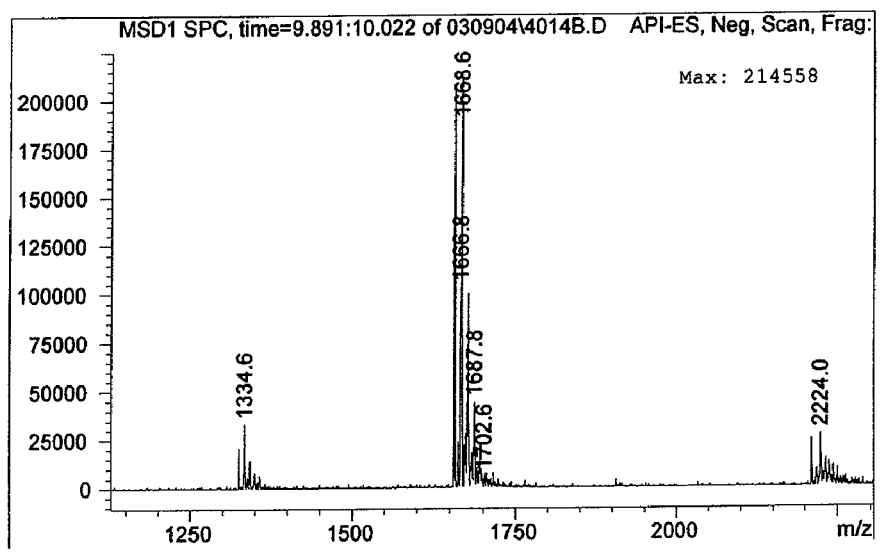
FIG. 15 depicts a mass spectrum of the peak at 9.913 minutes in the LC chromatogram of AL-DP-4014 shown in FIG. 14.
Figure 16:
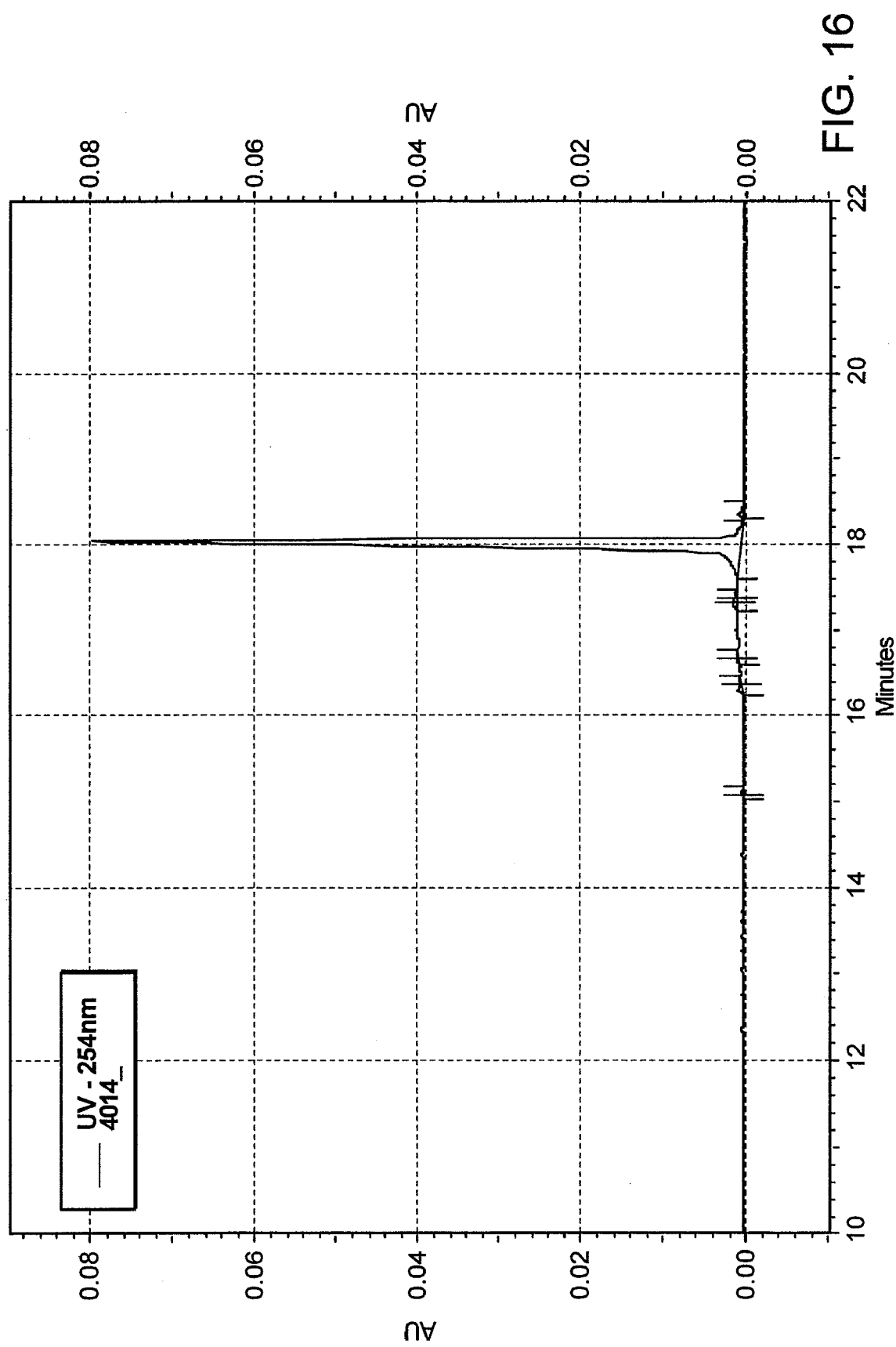
FIG. 16 depicts a capillary gel electrophoresis chromatogram of AL-DP-4014.
Figure 17:
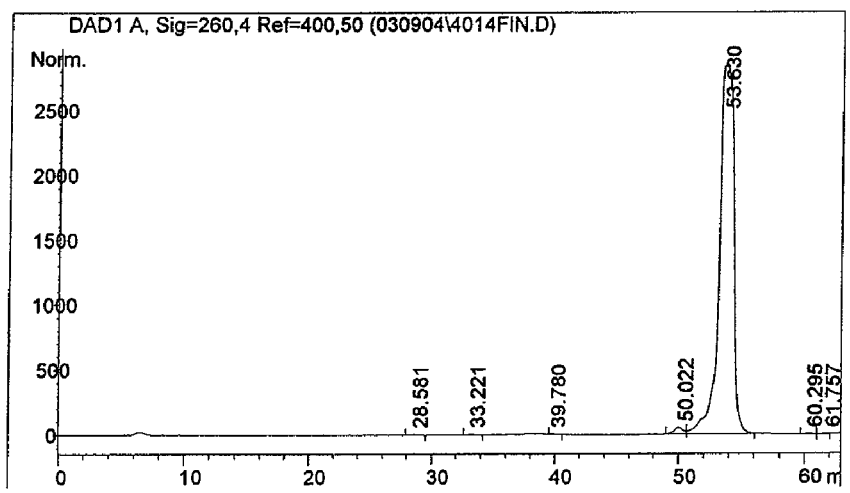
FIG. 17 depicts a reverse phase HPLC chromatogram of AL-DP-4014.
Figure 18:
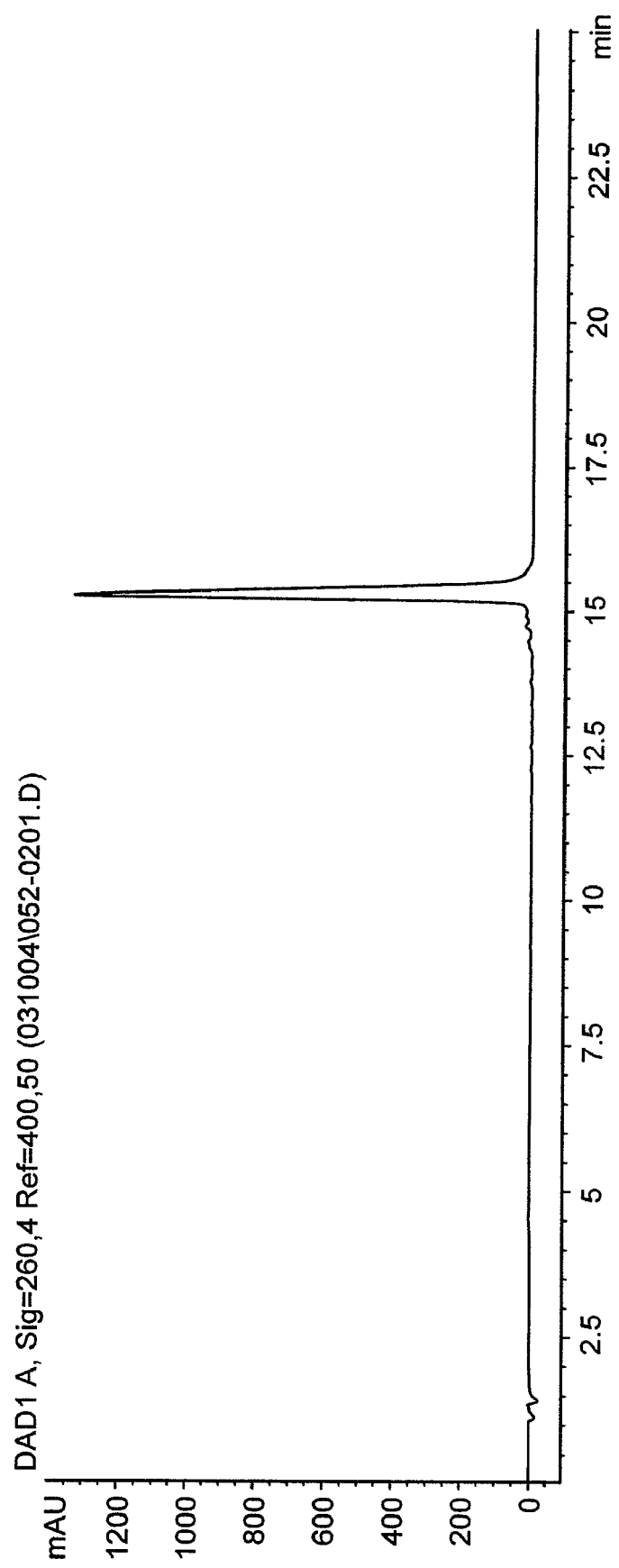
FIG. 18 depicts an ion exchange chromatogram of AL-DP-4014.
Figure 19:
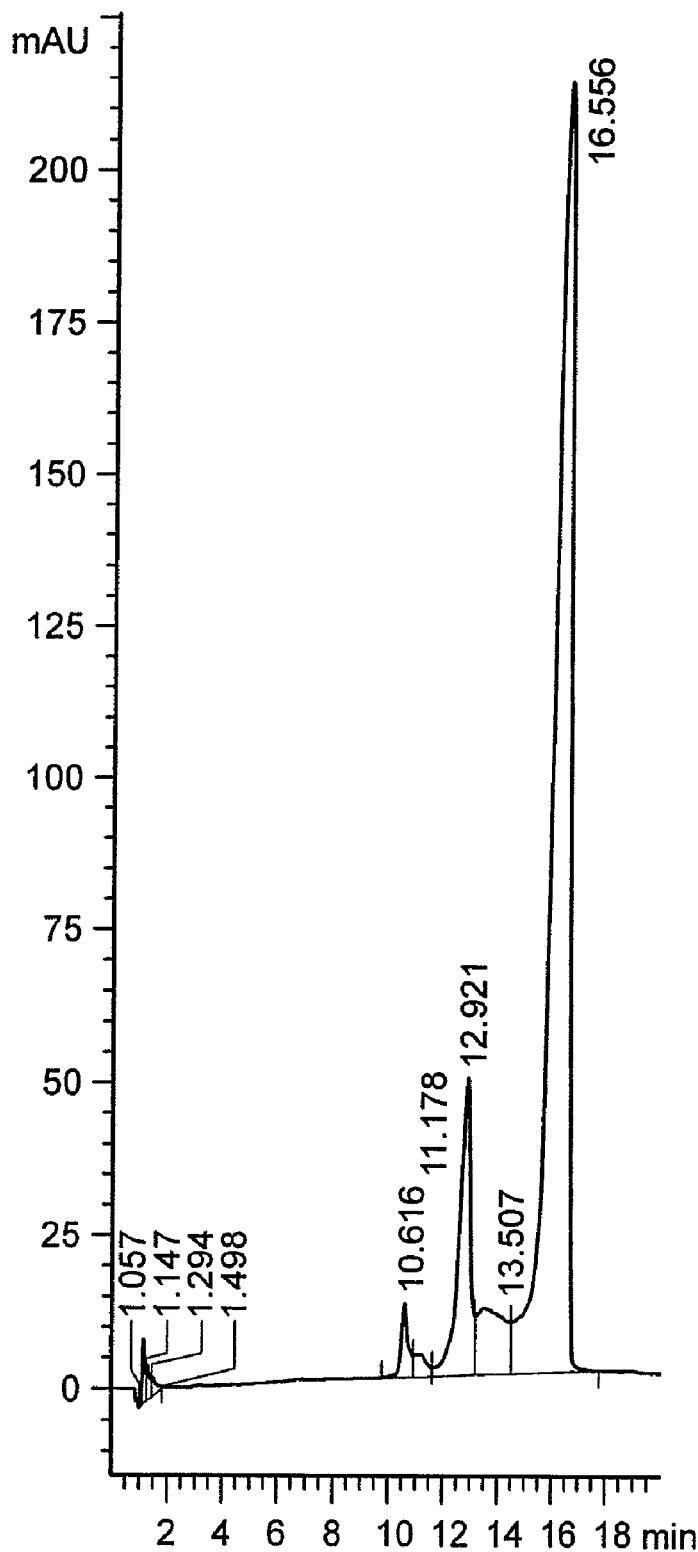
FIG. 19 depicts a LC-MS chromatogram of AL-DP-4127.
Figure 20:
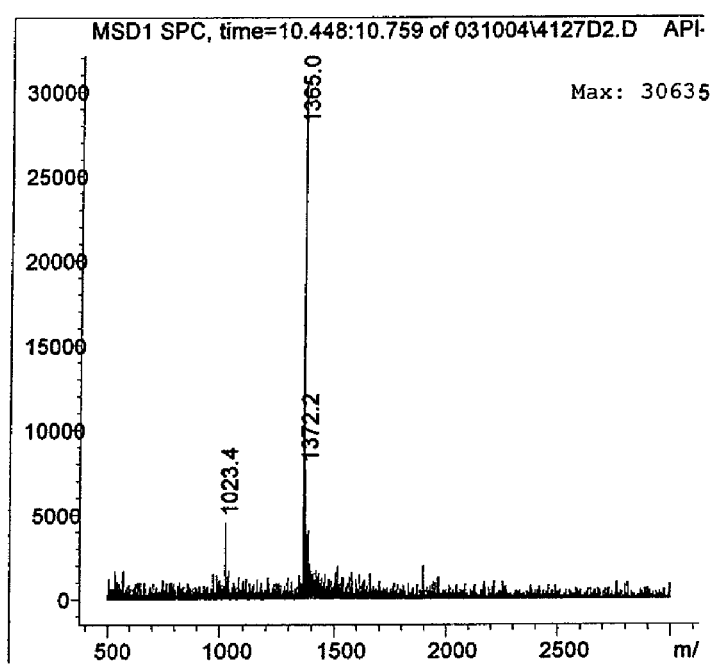
FIG. 20 depicts a mass spectrum of the peak at 10.616 minutes in the LC chromatogram of AL-DP-4127 shown in FIG. 19.
Figure 21:
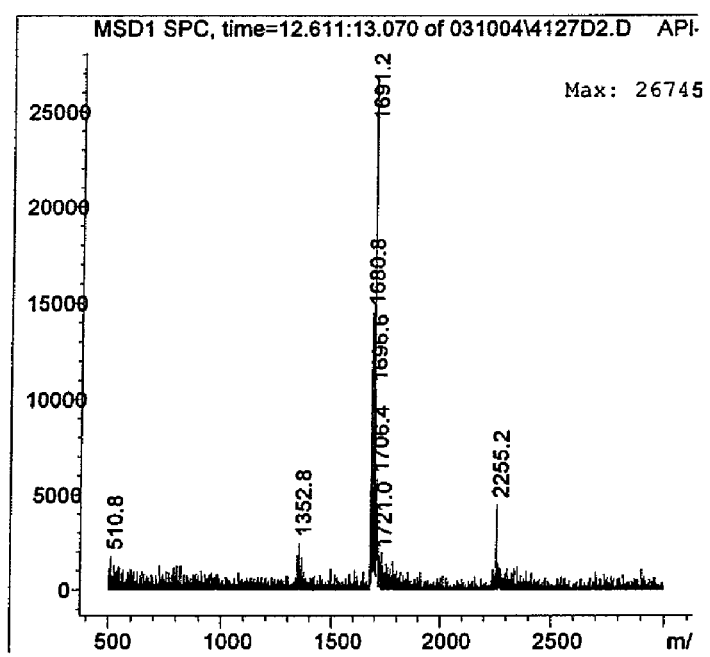
FIG. 21 depicts a mass spectrum of the peak at 12.921 minutes in the LC chromatogram of AL-DP-4127 shown in FIG. 19.
Figure 22:
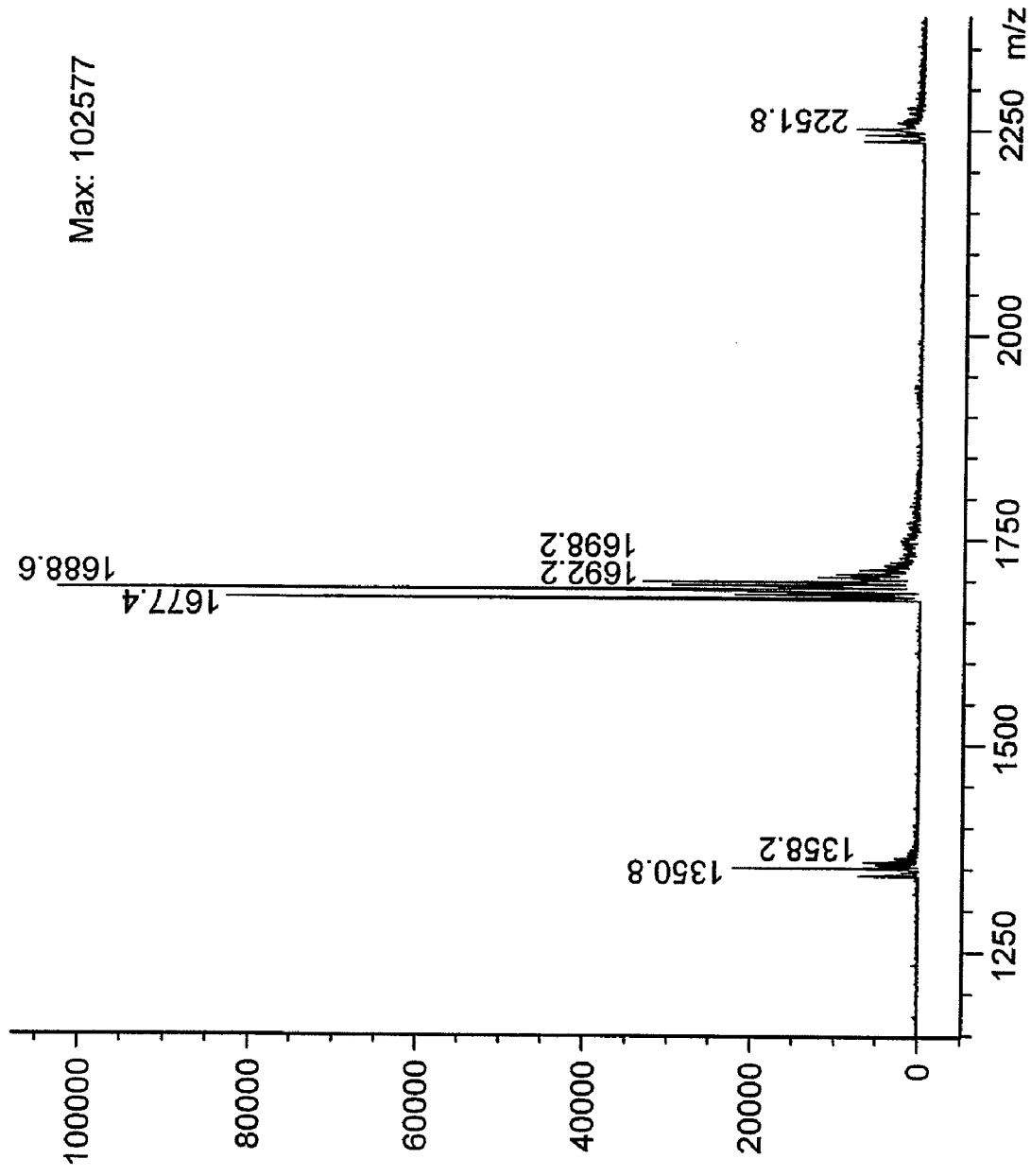
FIG. 22 depicts a mass spectrum of the peak at 16.556 minutes in the LC chromatogram of AL-DP-4127 shown in FIG. 19.
Figure 23:
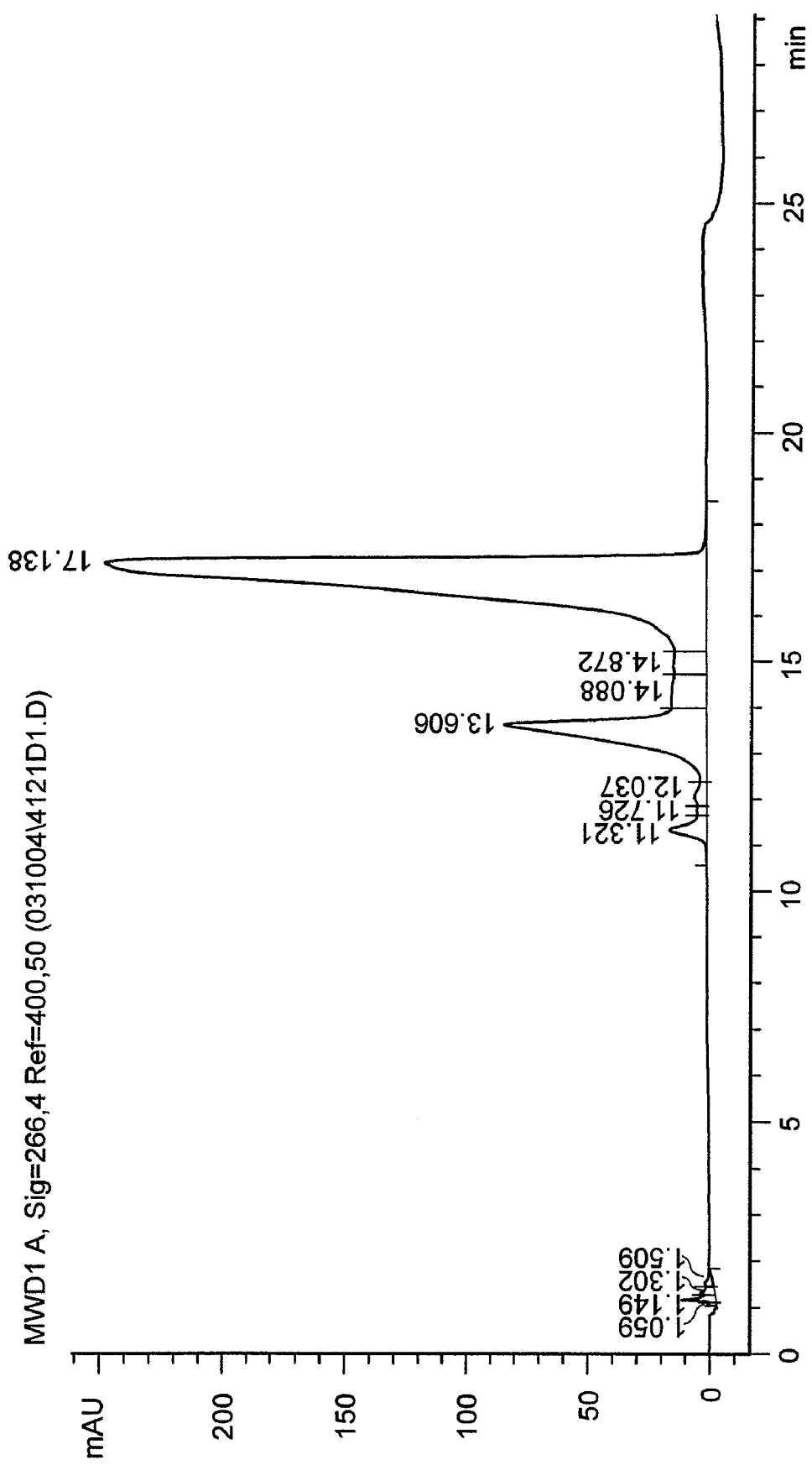
FIG. 23 depicts a LC-MS chromatogram of AL-DP-4127.
Figure 24:
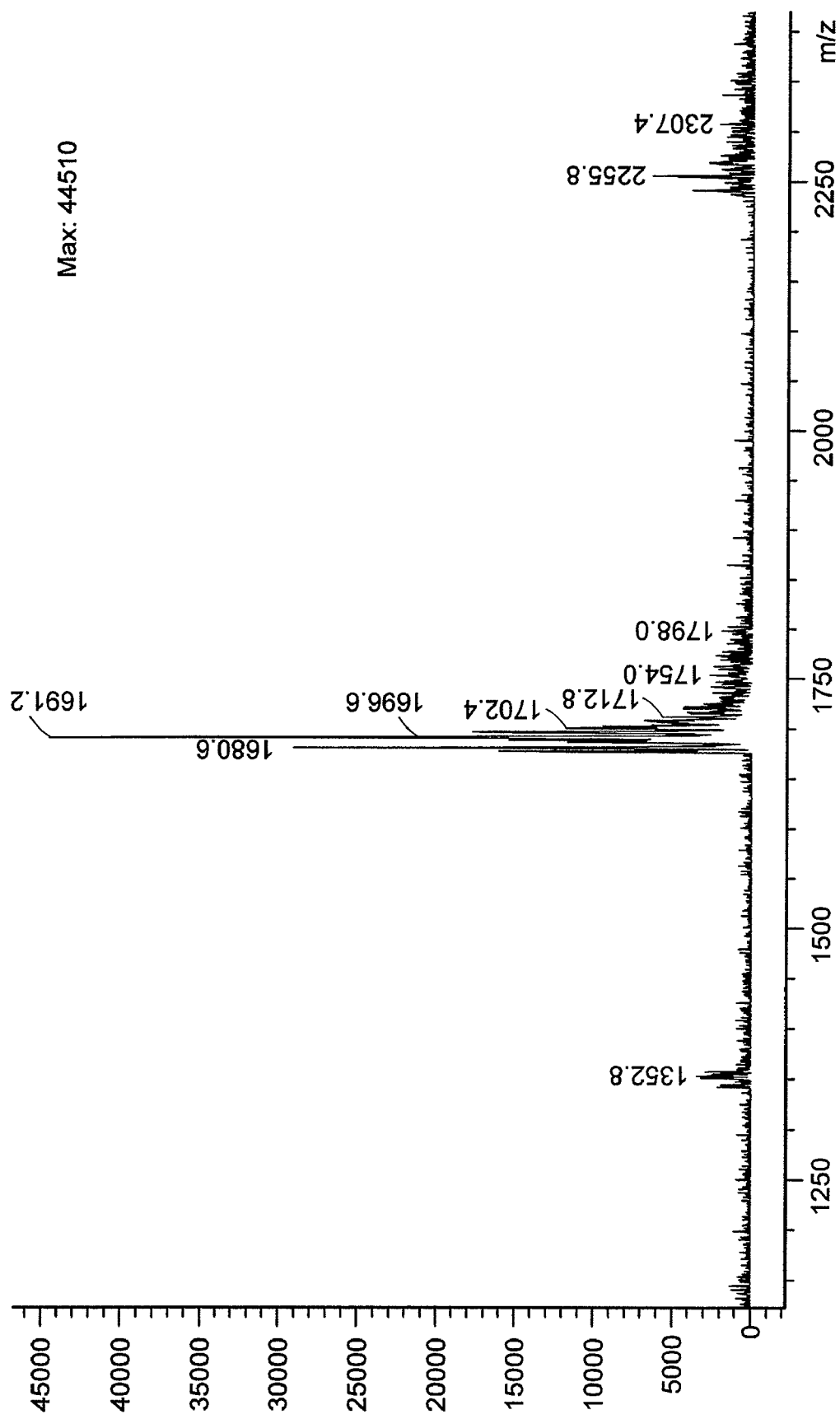
FIG. 24 depicts a mass spectrum of a minor contaminant which appears as a peak at 13.397 minutes in the LC chromatogram of AL-DP-4127 shown in FIG. 23.
Figure 25:
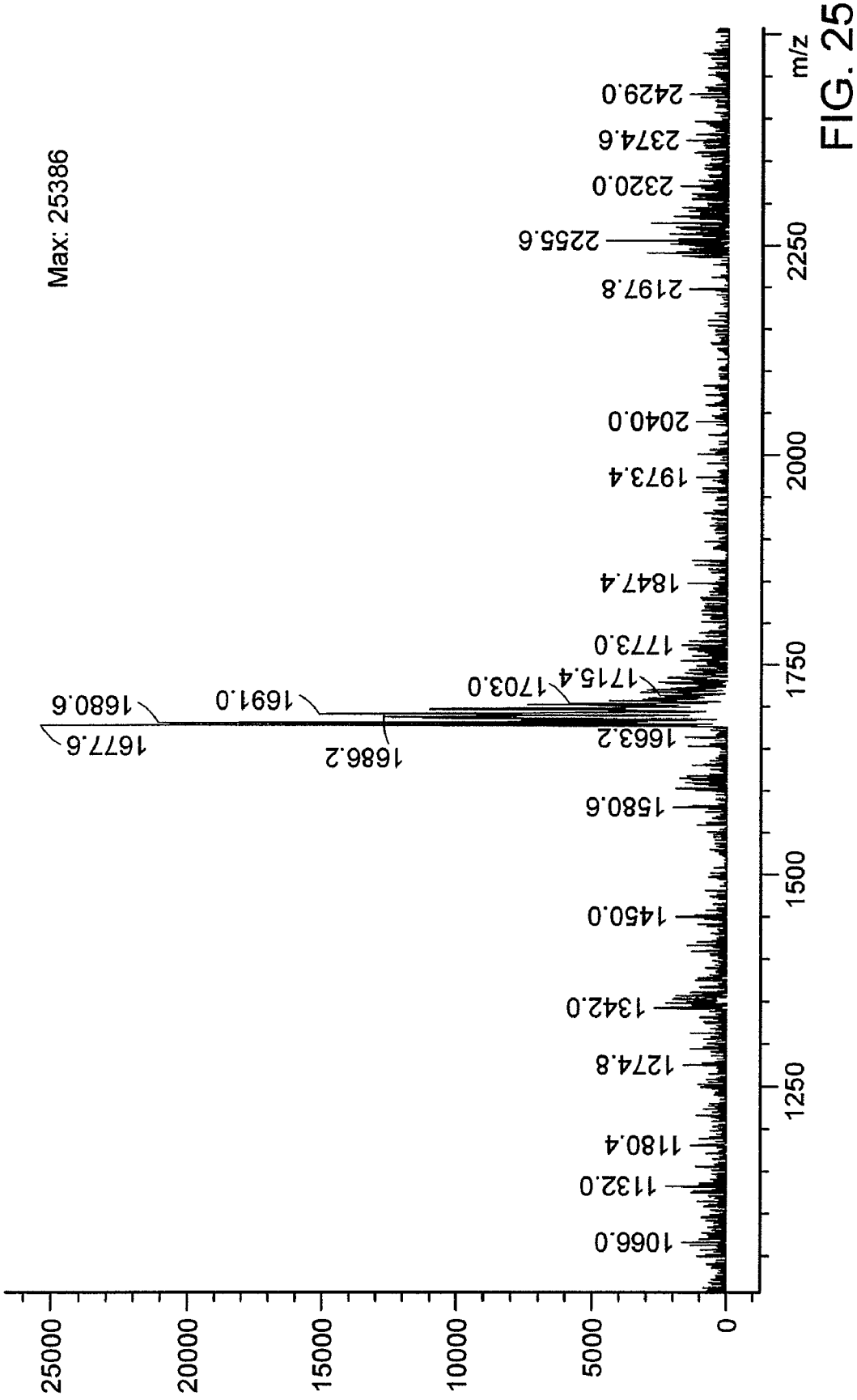
FIG. 25 depicts a mass spectrum of a minor contaminant which appears as a peak at 13.201 minutes in the LC chromatogram of AL-DP-4127 shown in FIG. 23.
Figure 26:
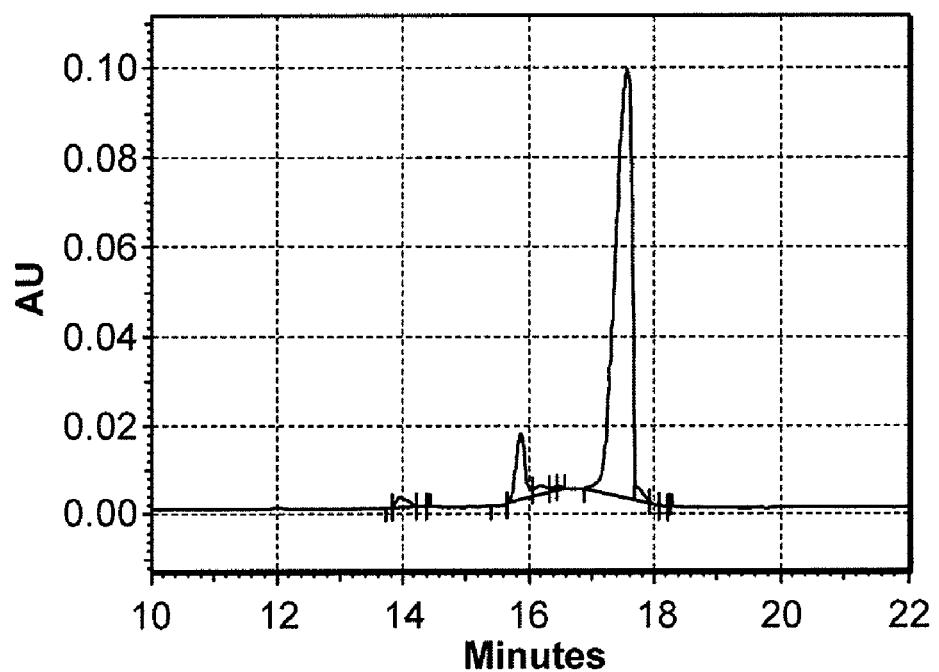
FIG. 26 depicts a capillary gel electrophoresis chromatogram of AL-DP-4127.
Figure 27:
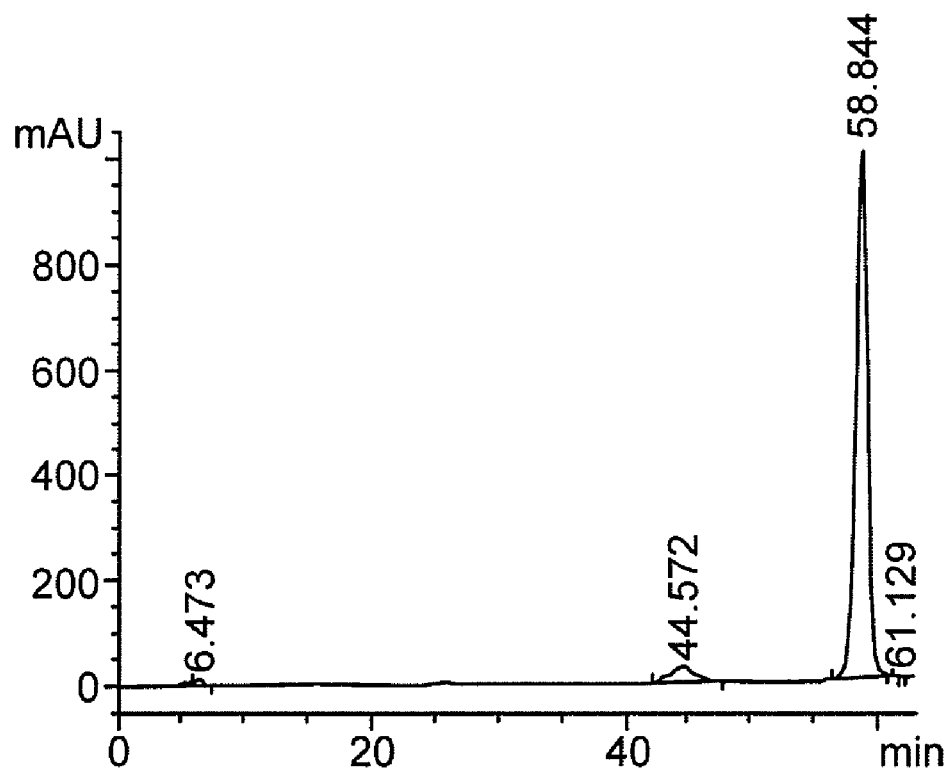
FIG. 27 depicts a reverse phase HPLC chromatogram of AL-DP-4127.
Figure 28:
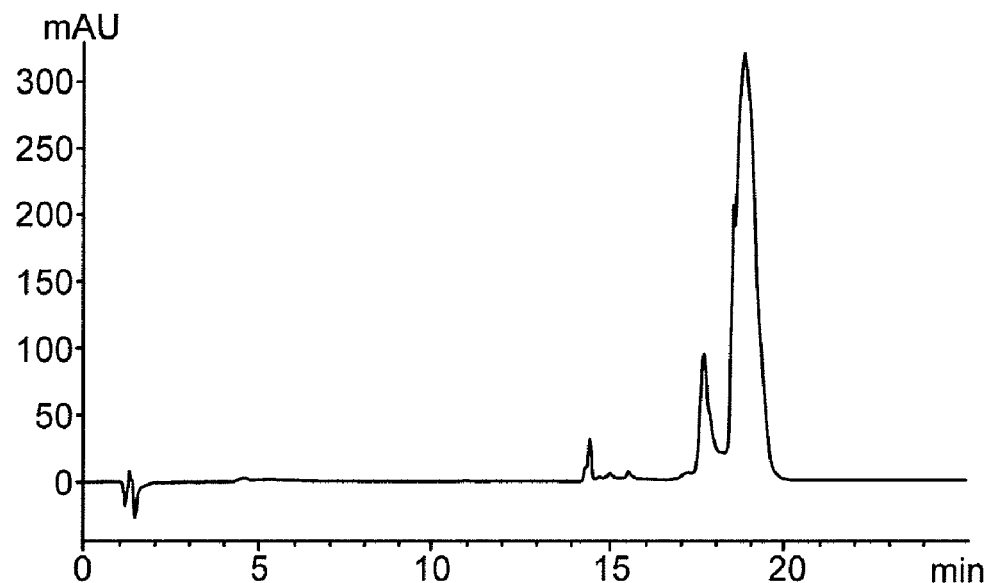
FIG. 28 depicts an ion exchange chromatogram of AL-DP-4127.
Figure 29:
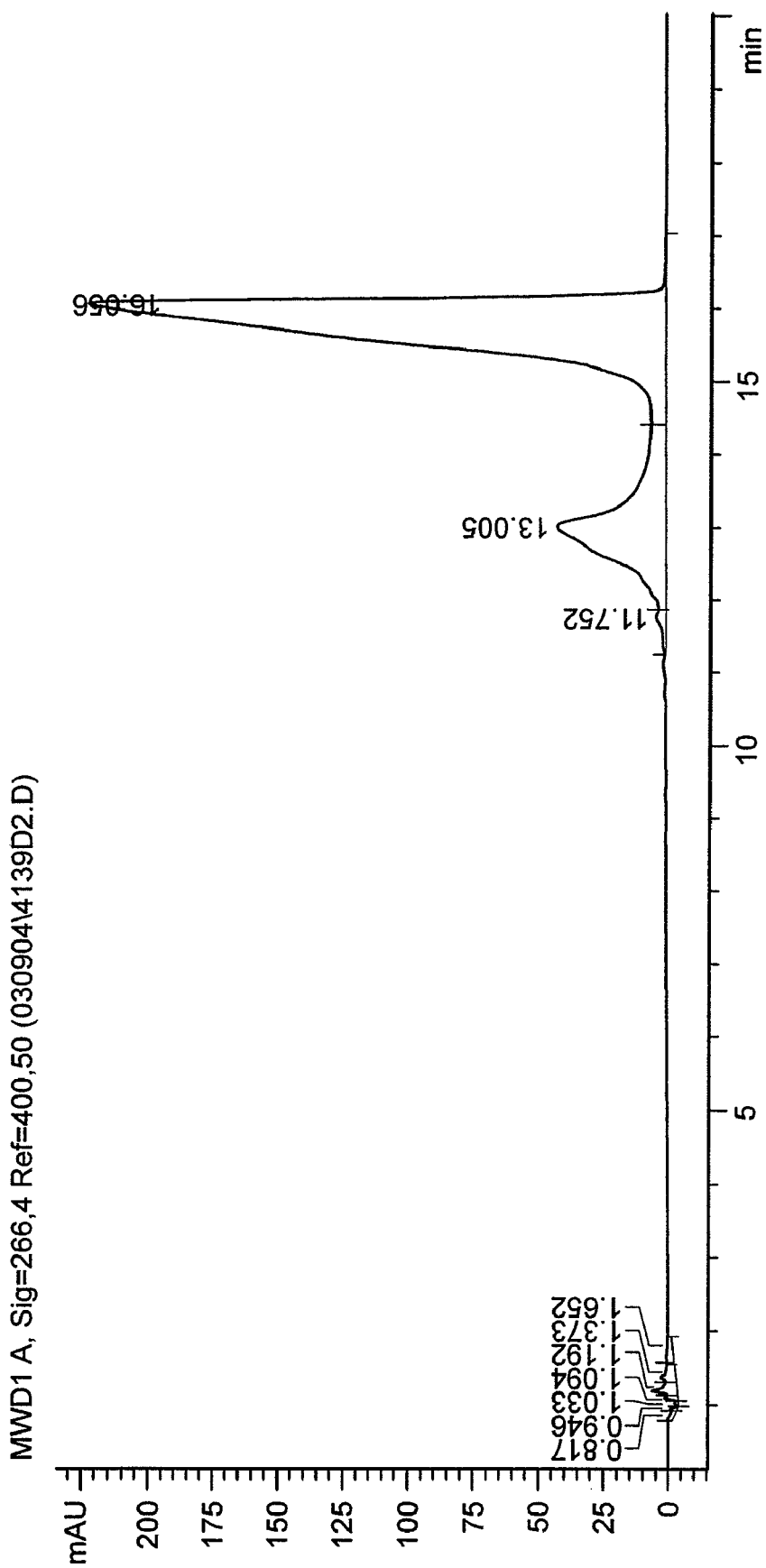
FIG. 29 depicts a LC-MS chromatogram of AL-DP-4139.
Figure 30:
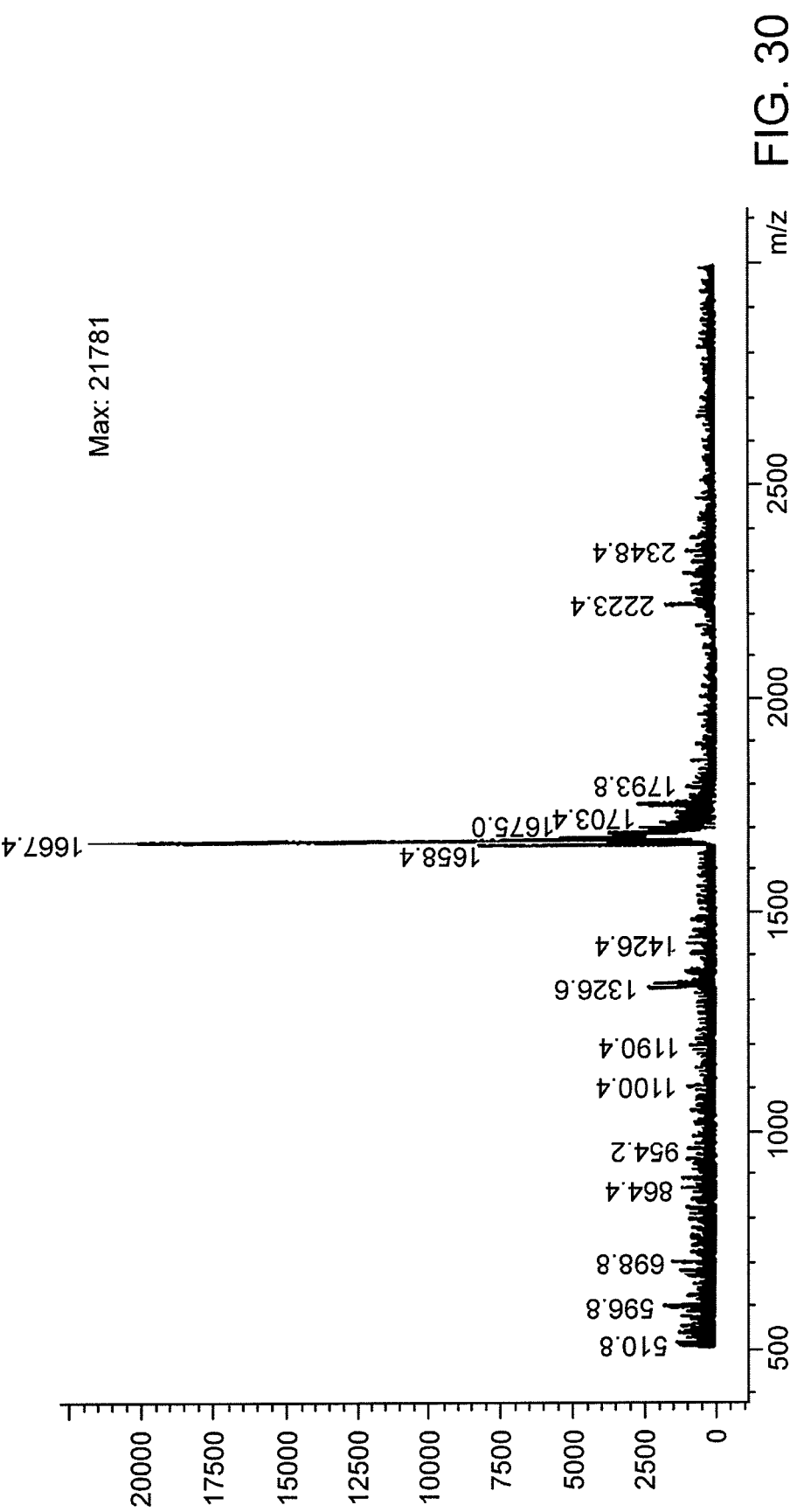
FIG. 30 depicts a mass spectrum of the peak at 13.005 minutes in the LC chromatogram of AL-DP-4139 shown in FIG. 29.
Figure 31:
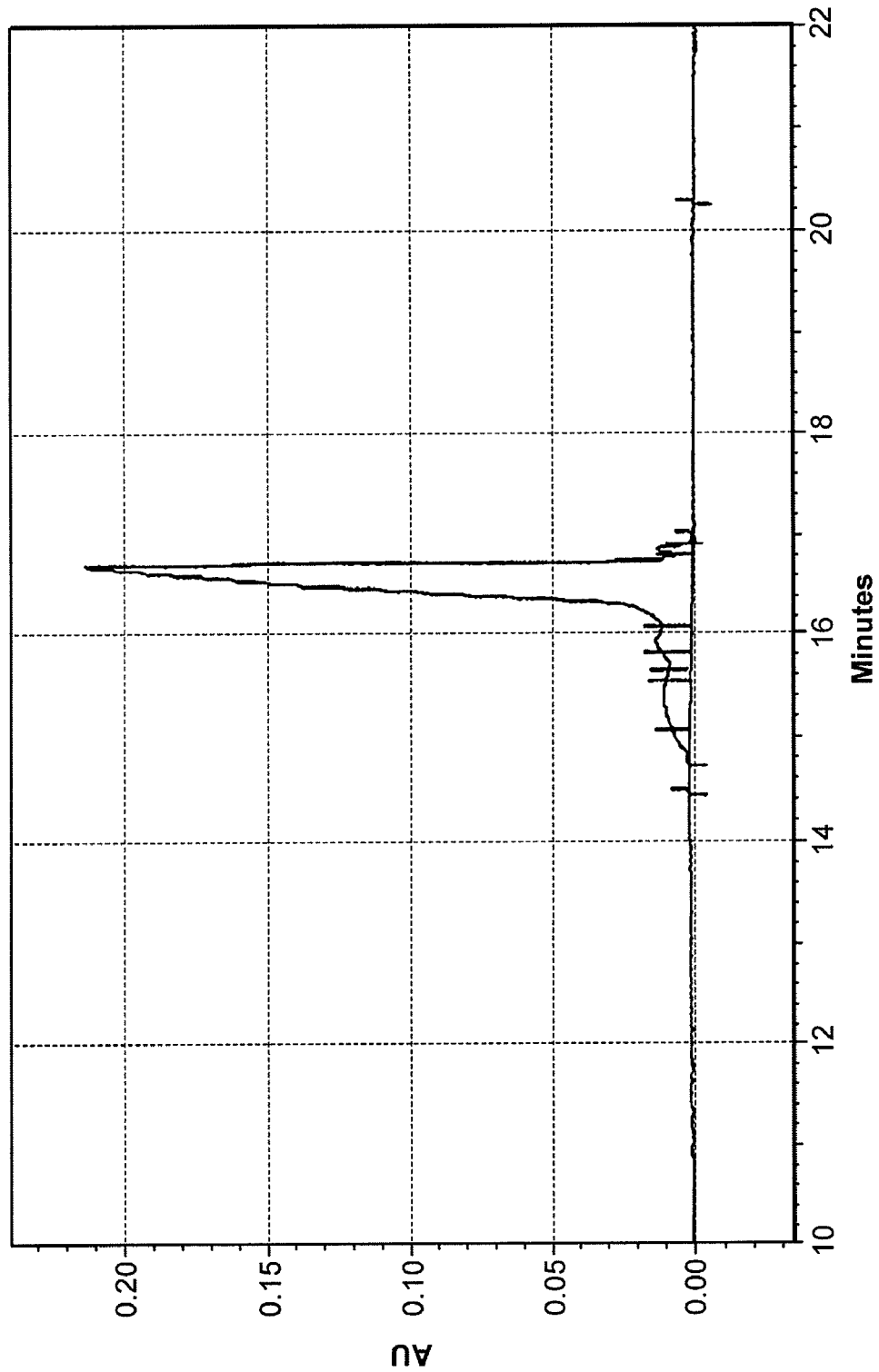
FIG. 31 depicts a capillary gel electrophoresis chromatogram of AL-DP-4139.
Figure 32:
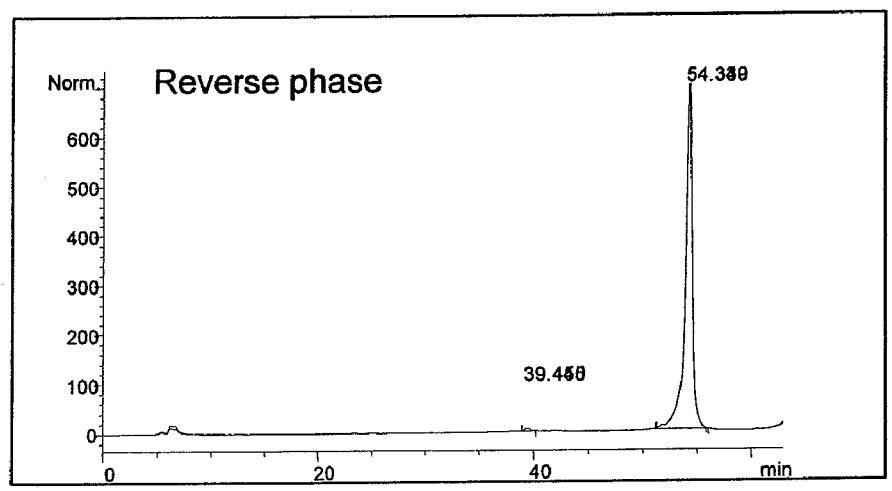
FIG. 32 depicts a reverse phase HPLC chromatogram of AL-DP-4139.
Figure 33:
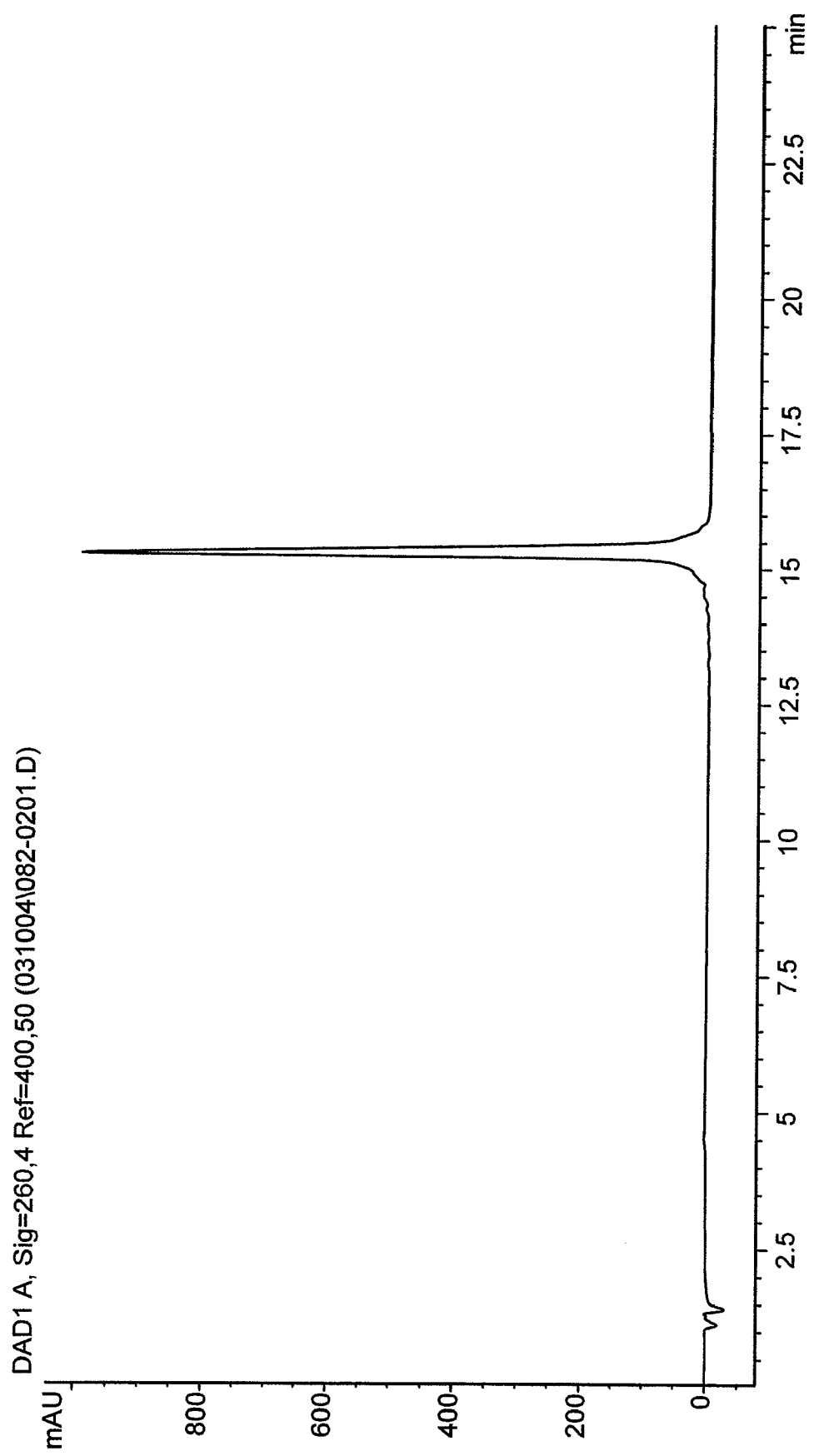
FIG. 33 depicts an ion exchange chromatogram of AL-DP-4139.
Figure 34:
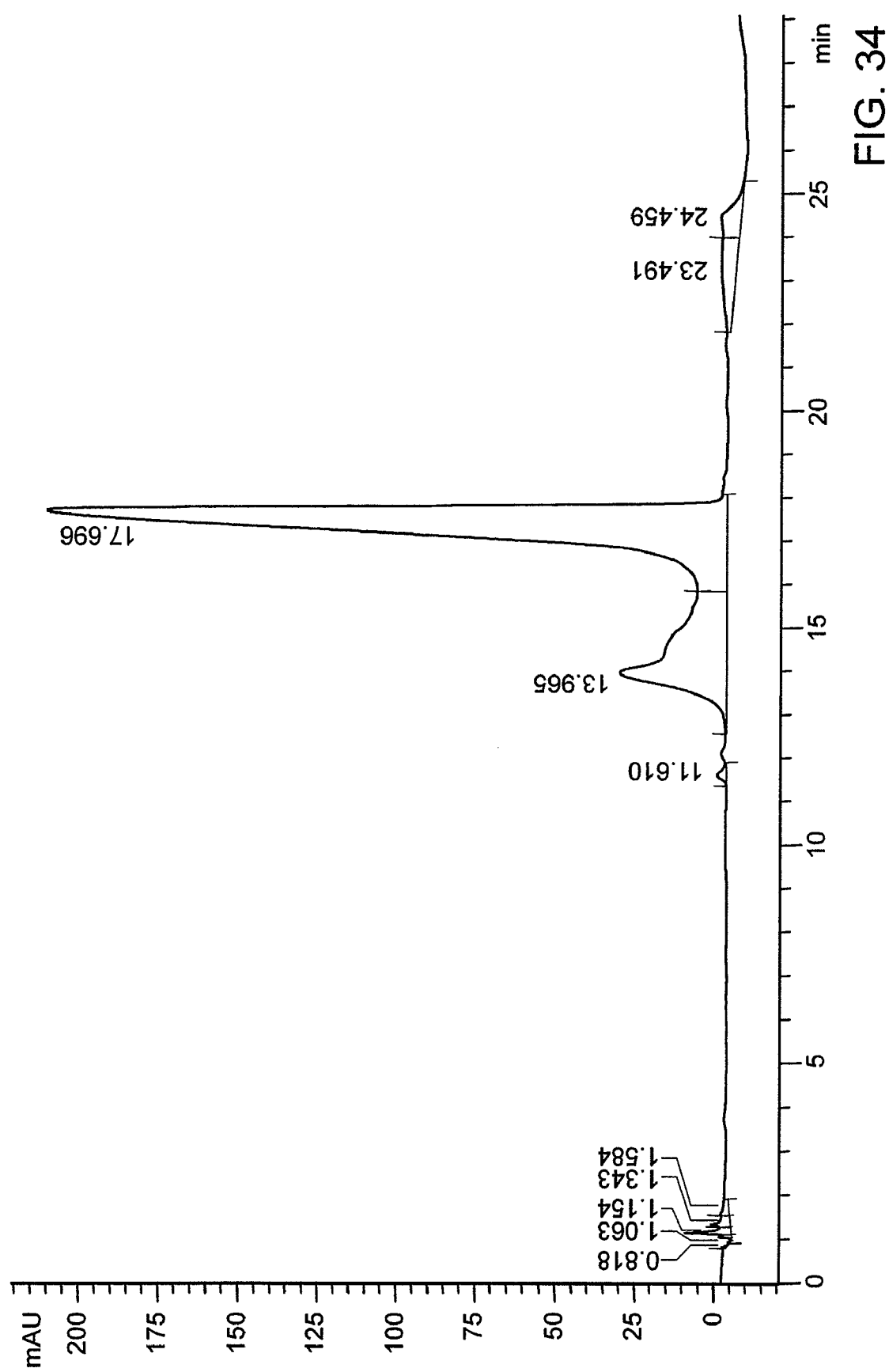
FIG. 34 depicts a LC-MS chromatogram of AL-DP-4140.
Figure 35:
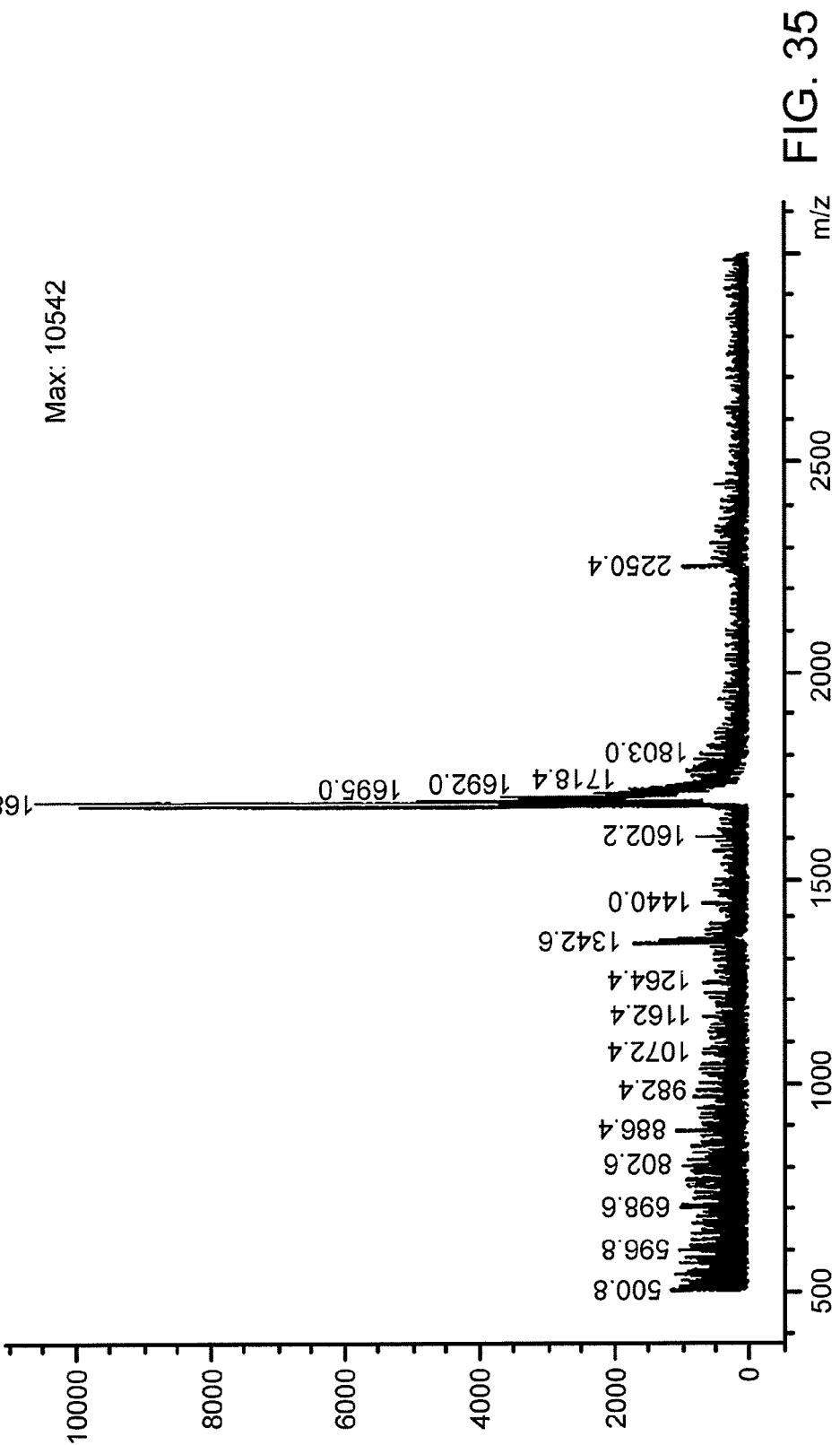
FIG. 35 depicts a mass spectrum of the peak at 13.965 minutes in the LC chromatogram of AL-DP-4140 shown in FIG. 34.
Figure 36:
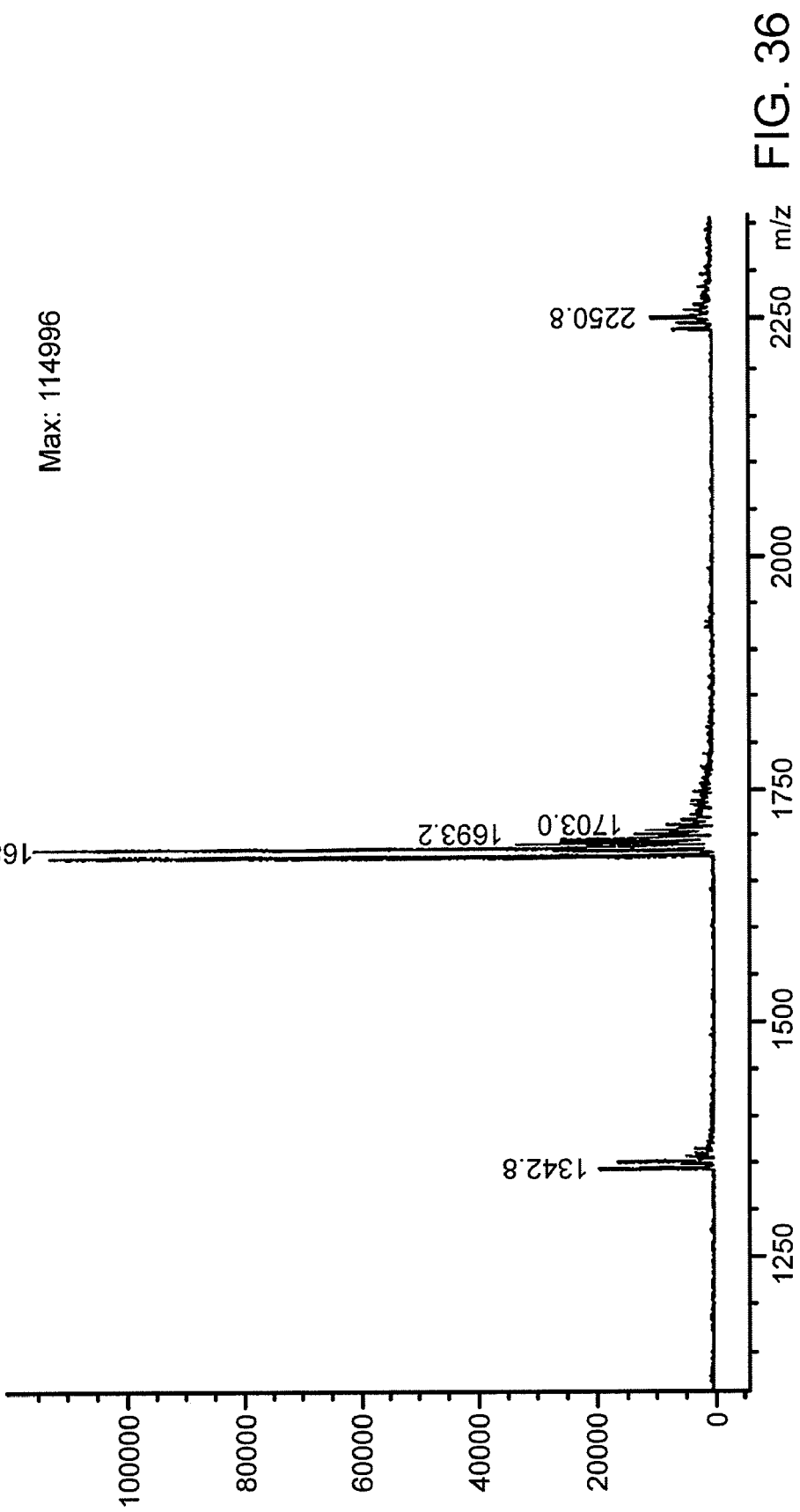
FIG. 36 depicts a mass spectrum of the peak at 17.696 minutes in the LC chromatogram of AL-DP-4140 shown in FIG. 34.
Figure 37:
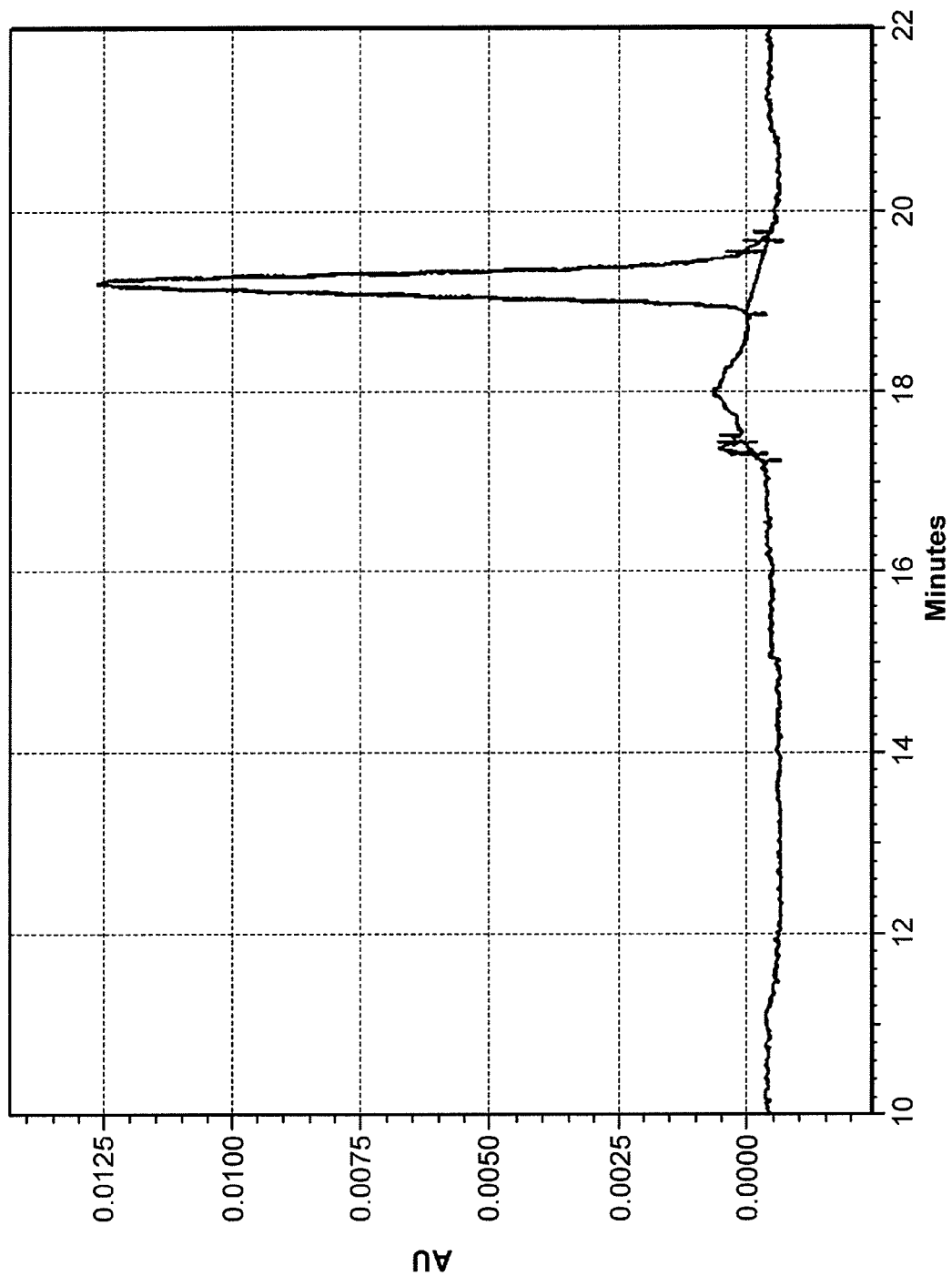
FIG. 37 depicts a capillary gel electrophoresis chromatogram of AL-DP-4140.
Figure 38:
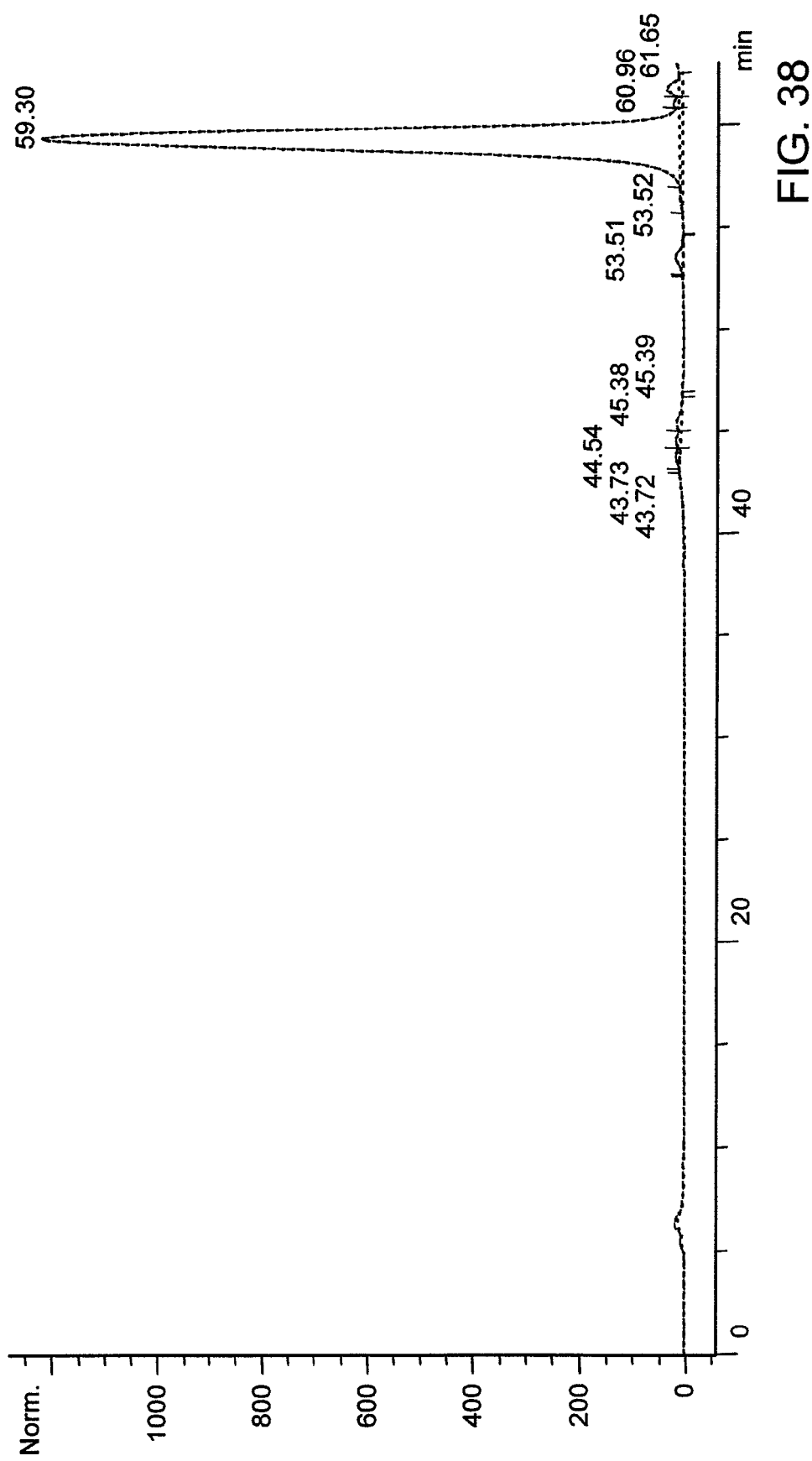
FIG. 38 depicts a reverse phase HPLC chromatogram of AL-DP-4140.
Figure 39:
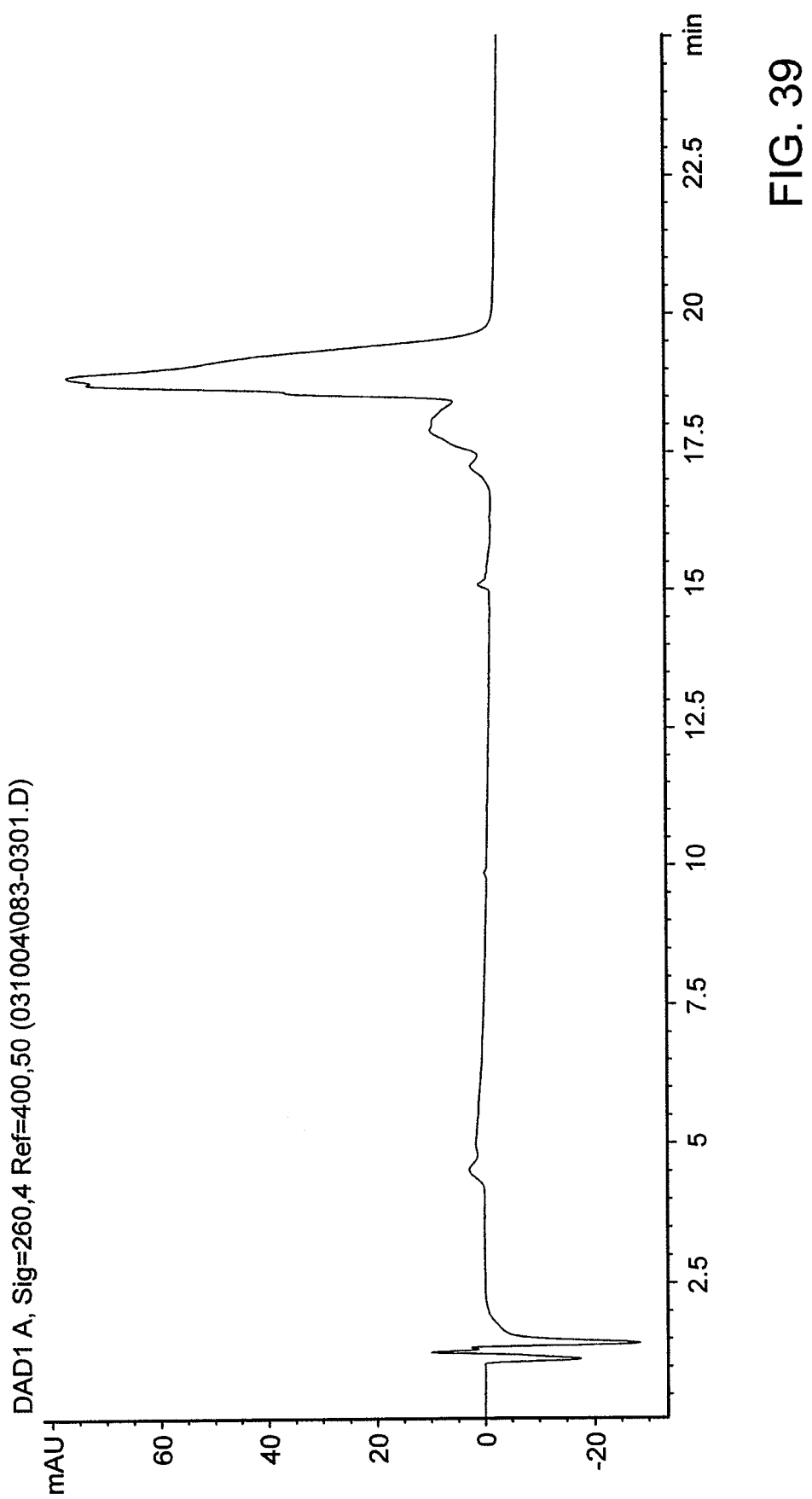
FIG. 39 depicts an ion exchange chromatogram of AL-DP-4140.
Figure 40:
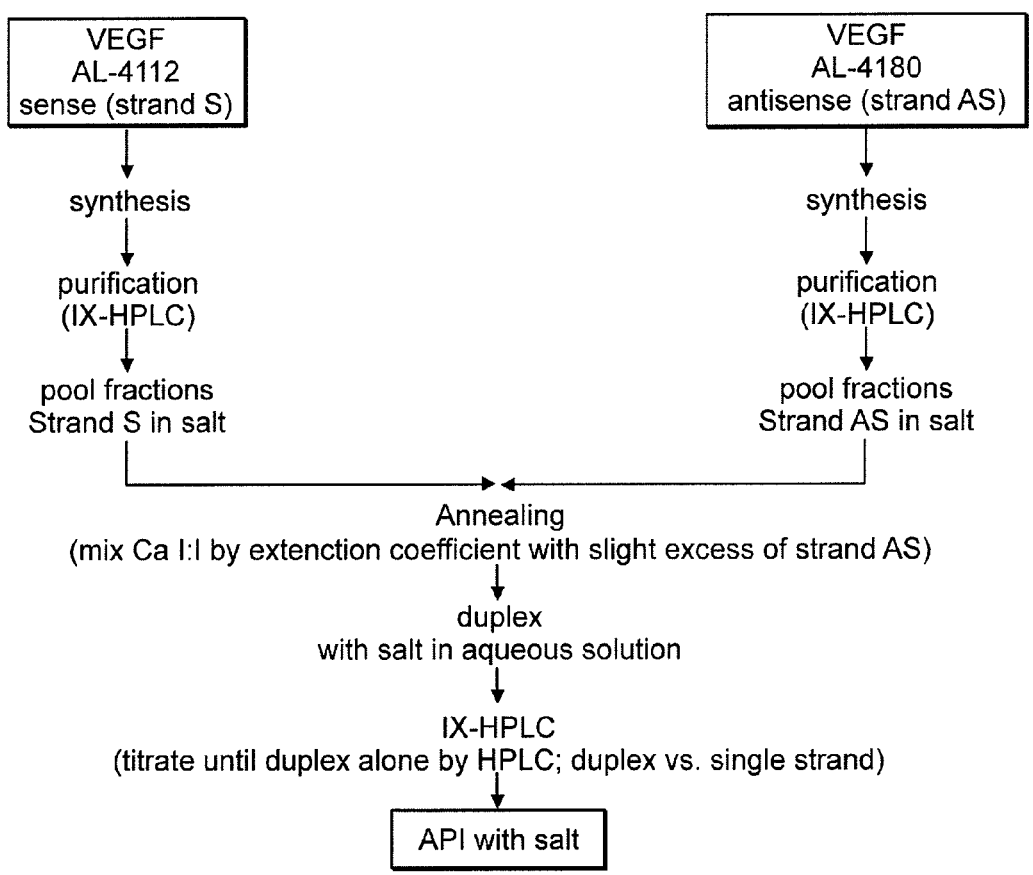
FIG. 40 depicts alternative steps for the two-strand RNA purification procedure.
Figure 41:
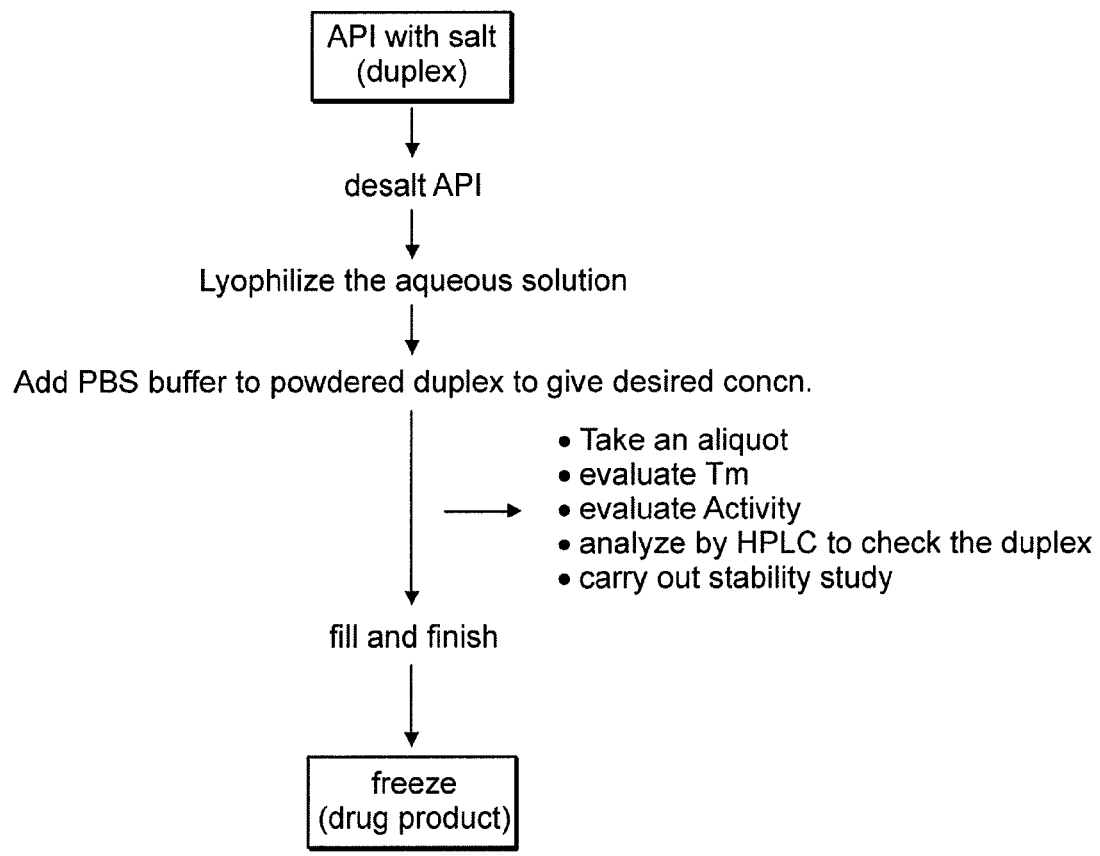
FIG. 41 depicts alternative steps for the two-strand RNA purification procedure.
Figure 42:
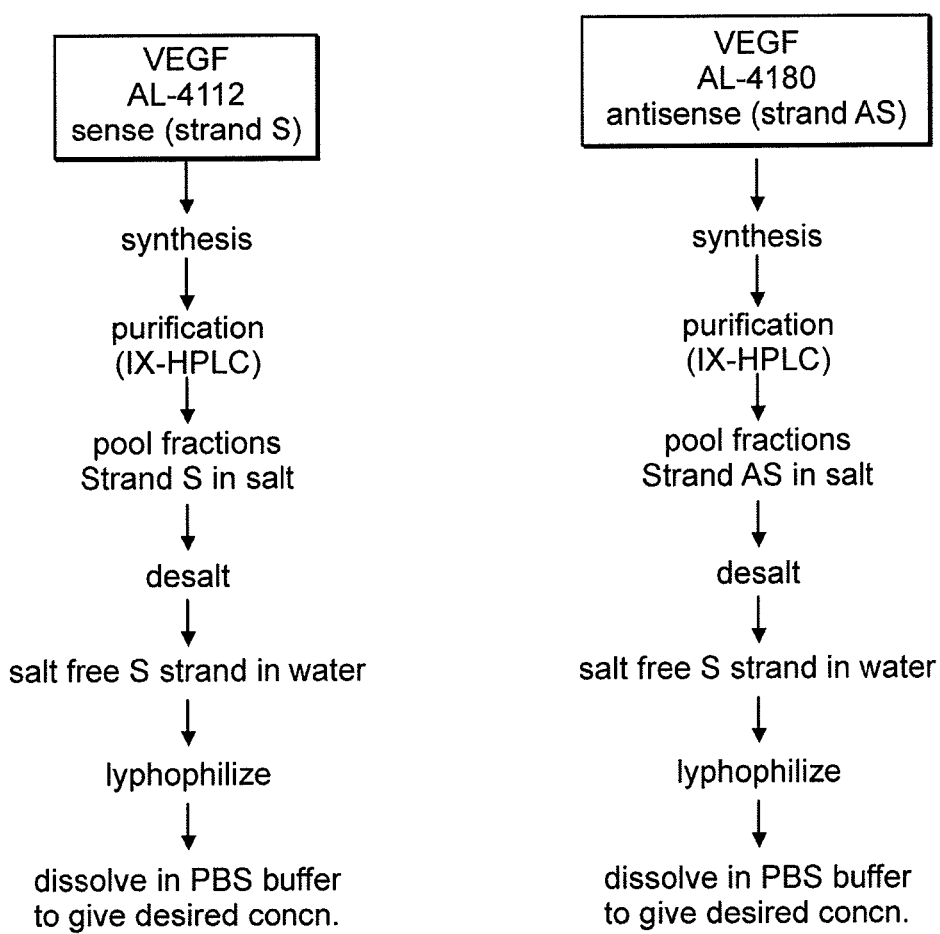
FIG. 42 depicts alternative steps for the two-strand RNA purification procedure.
Figure 43:
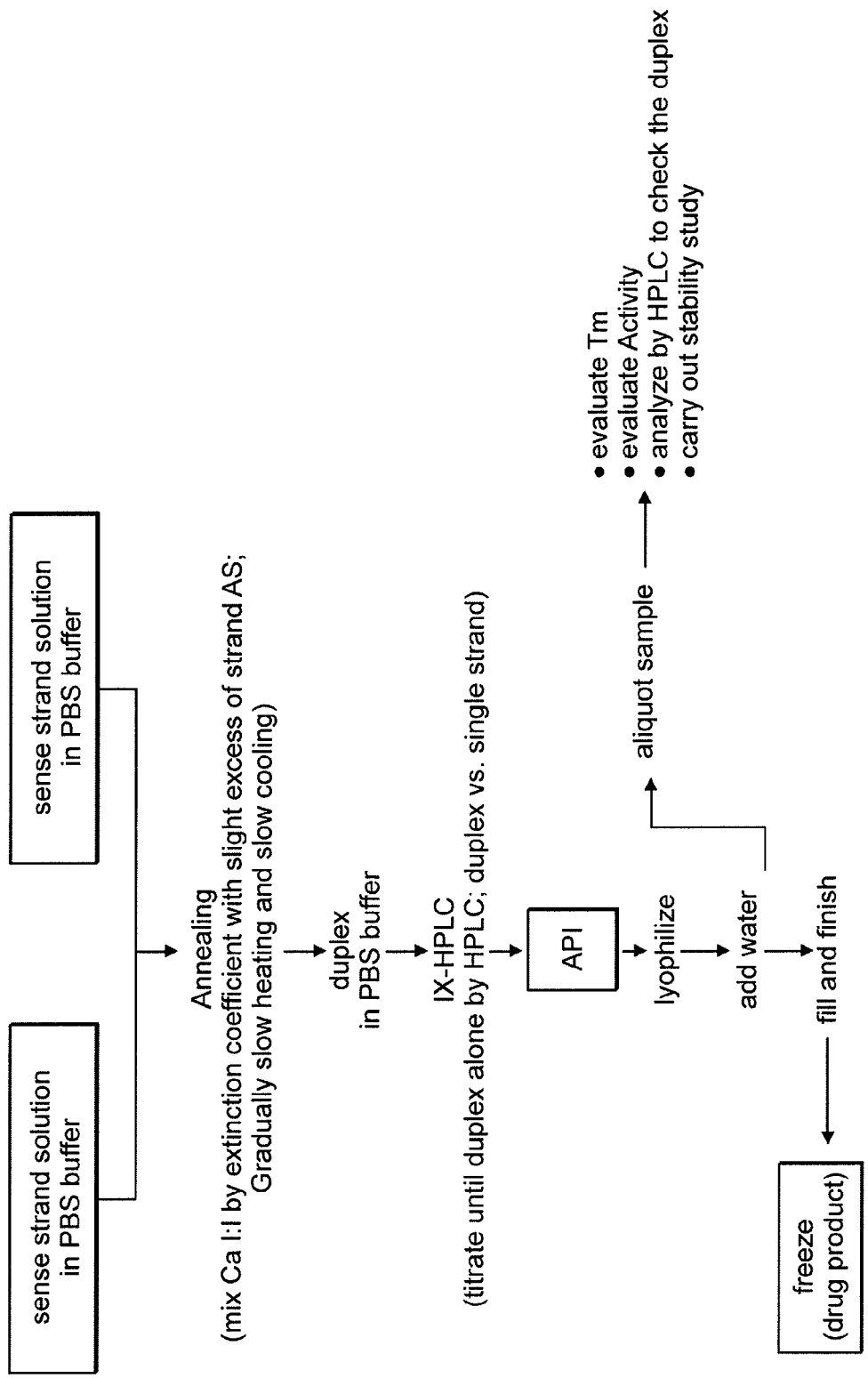
FIG. 43 depicts alternative steps for the two-strand RNA purification procedure.

The Applicants have surprising discovered that impurities in a composition of single-stranded RNA can be readily removed by HPLC purification of a mixture of single-stranded RNA that has been annealed to generate double-stranded RNA. A diagram illustrating the overall procedure is presented in FIG. 9. The structure of AL-4112, AL-4180, AL-DP-4014, AL-2200, AL-22-1, AL-DP-4127, AL-2299, AL-2300, AL-DP-4139, AL-2281, AL-2282, and AL-DP-4140 is presented in FIG. 10. The specific procedure for the purification of AL-DP-4014, the components of which are AL-4112 and AL-4180, is shown in FIGS. 11 and 12. AL-DP-4127, AL-DP-4139, and AL-DP-4140 were also purified using the procedures described in FIGS. 9, 11, and 12. The results from the analyses are presented in FIGS. 19-39.

Alternative procedures of RNA purification using the two-strand method are presented in FIGS. 40-43.

One aspect of the present invention relates to a method of purifying an oligonucleotide, comprising the steps of:

annealing a first oligonucleotide with a second oligonucleotide to form a double-stranded oligonucleotide, subjecting said double-stranded oligonucleotide to chromatographic purification.

In certain embodiments, the present invention relates to the aforementioned method, wherein said annealing a first oligonucleotide with a second oligonucleotide is done at a temperature between a first temperature and a second temperature, wherein said first temperature is about the $T_m$ of a double-stranded oligonucleotide consisting of said first oligonucleotide and a third oligonucleotide, wherein said third oligonucleotide is the antisense sequence corresponding to the first oligonucleotide, and said second temperature is about 5 degrees below said first temperature.

In certain embodiments, the present invention relates to the aforementioned method, wherein said chromatographic purification is liquid chromatography.

In certain embodiments, the present invention relates to the aforementioned method, wherein said chromatographic purification is high-performance liquid chromatography.

In certain embodiments, the present invention relates to the aforementioned method, wherein said first oligonucleotide is an oligomer of ribonucleotides.

In certain embodiments, the present invention relates to the aforementioned method, wherein said second oligonucleotide is an oligomer of ribonucleotides.

In certain embodiments, the present invention relates to the aforementioned method, wherein said first oligonucleotide is an oligomer of ribonucleotides, and said second oligonucleotide is an oligomer of ribonucleotides.

RNA HPLC Methods

As described above, high-performance liquid chromatography (HPLC) is an important method used in the purification of RNA compounds. A large variety of columns, solvents, additives, and conditions have been reported for purifying oligonucleotides. However, current procedures for purifying RNA compounds are not able to separate the RNA compound from significant amounts of impurities. The Applicants report herein improvements to existing HPLC procedures thereby providing the RNA compound with substantially fewer impurities:

1) Use tetrabutylammonium acetate as ion-pairing agent in analytical HPLC separations of oligonucleotides. See M. Gilar for use of tetrabutylammonium acetate in analytical HPLC separations. M. Gilar *Analytical Biochemistry* 2001, 298, 196-206.

2) HPLC purification in DMT-off mode with C-18 column or C-4 column for lipophilic conjugates of RNA compounds.

3) HPLC purification of RNA compounds using ethanol or acetonitrile as the solvent.

2'-Protecting Groups for RNA Synthesis

As described above, protecting groups play a critical role in RNA synthesis. The Applicants describe herein several new protecting groups that can be used in RNA synthesis. One class of 2'-protecting groups that can be used in RNA synthesis is carbonates. One preferred carbonate is propargyl carbonate shown below.

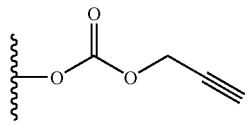

The propargyl carbonate can be removed using benzyltriethylammonium tetrathiomolybdate as described in *Org. Lett.* 2002, 4, 4731.

Another class of 2'-protecting groups that can be used in RNA synthesis is acetals. Acetal groups can be deprotected using aqueous acid. Several representative acetal protecting groups are shown below. See FIG. 44 for additional examples.

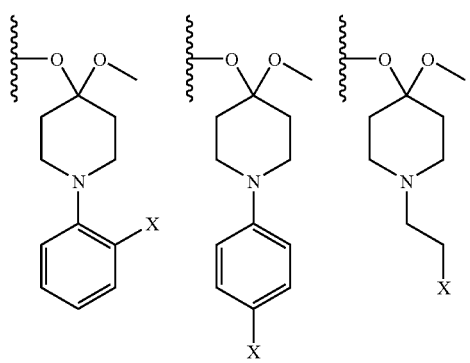

X = CN, $NO_2$, $CF_3$, $SO_2R$, or $CO_2R$

Other 2'-protecting groups that can be used in RNA synthesis are shown below.

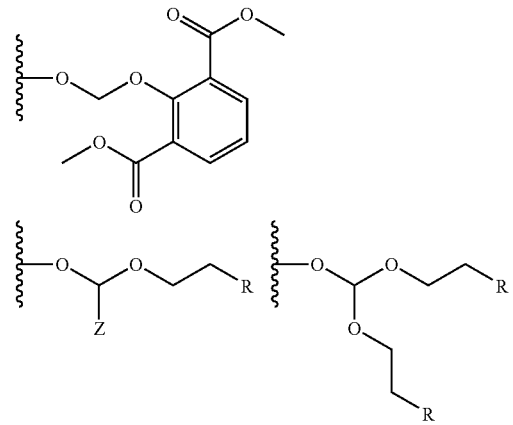

Z = H or alkyl
R = CN, $NO_2$, $CF_3$, F, or OMe

In addition, a bis-silyl strategy could be used in RNA synthesis. This strategy involves protecting both the 2'-hydroxyl group of the ribose and the phosphate attached to the 3'-position of the ribose with a silyl group. A representative example is presented below in FIG. 44.

Figure 44:
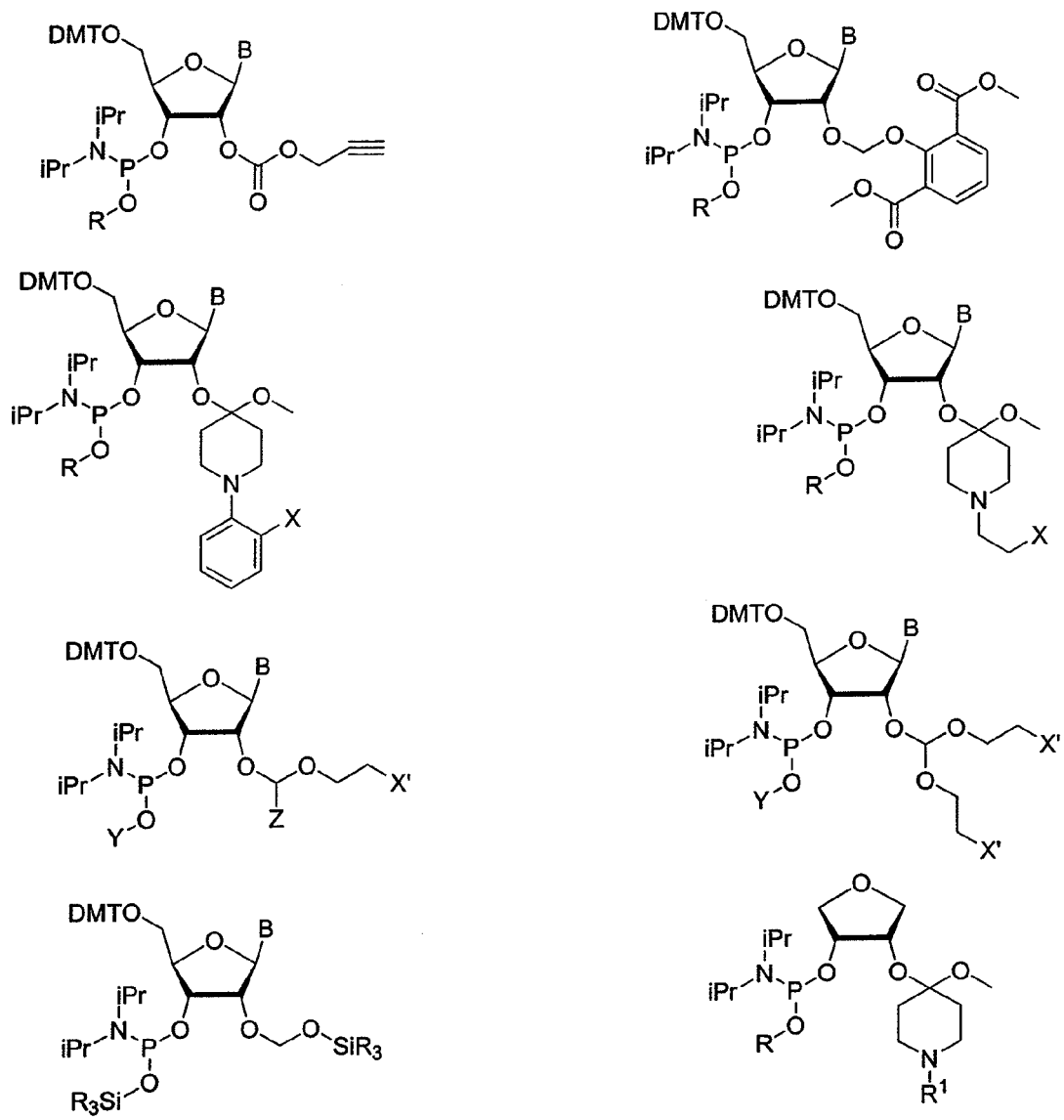
FIG. 44 depicts nucleosides bearing various 2'-protecting groups. Note: The term "B" indicates protected C, G, A, U, or 5-Me-U. The term "X" indicates CN, NO$_2$, CF$_3$, SO$_2$R, or CO$_2$R. The term "X'" indicates CN, NO$_2$, CF$_3$, F, or OMe. The term "Z" indicates H or alkyl. The term "R$^1$" indicates oxazole, thiazole, or azole.

Representative examples of the above-mentioned protecting groups on various nucleosides are presented in FIG. 44.

Alternate 5'-Protecting Groups

In place of dimethoxytrityl (DMT), monomethoxytrityl (MMT), 9-phenylxanthen-9-yl (Pixyl) and 9-(p-methoxyphenyl)xanthen-9-yl (Mox) and their analogs can be employed.

Alternate Base-Protecting Groups

1) Nps and DNPS groups (Fukuyama)
2) phenacetyl (removal by penicillin G acylase)

Enzymatic Methods for Removal of Protecting Groups

Figure 45:
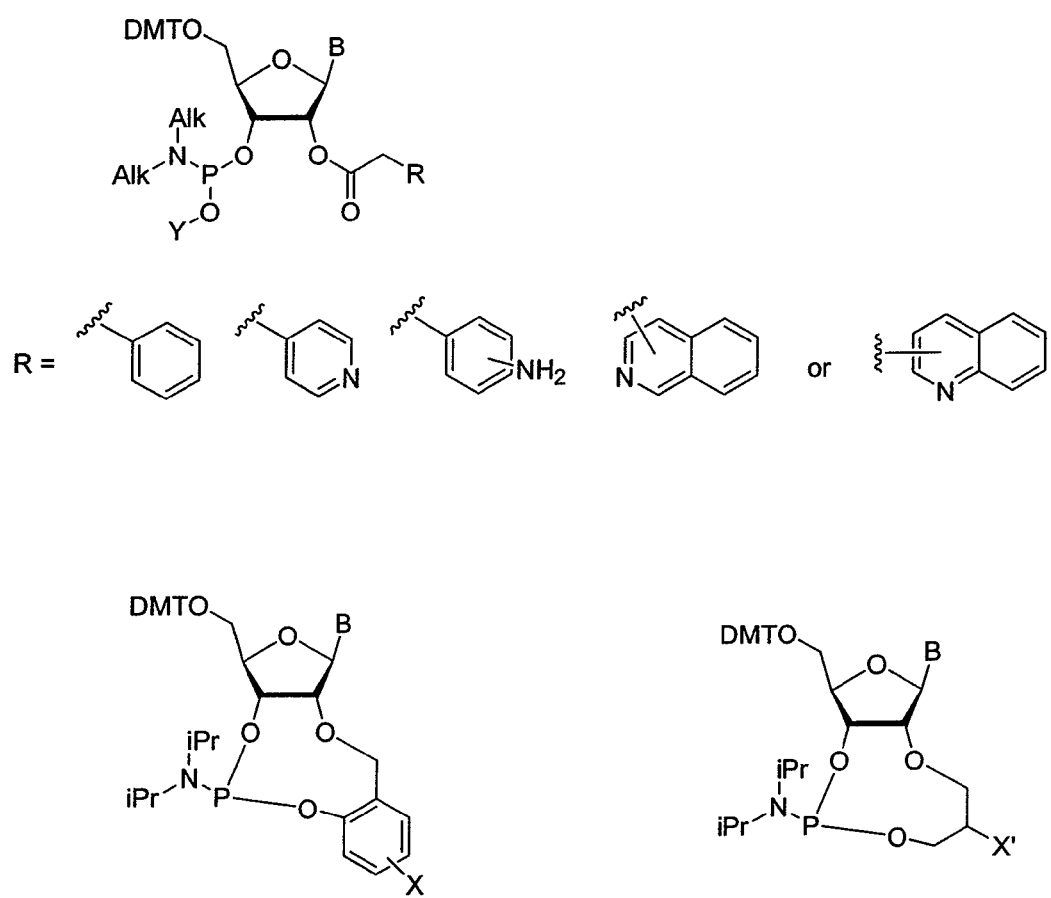
FIG. 45 depicts nucleosides bearing various 2'-protecting groups which can be removed by enzymatic cleavage. Note: The term "B" indicates U, 5-Me-U, 5-Me-C, G, or A. The term "X" indicates H, CN, NO$_2$, CF$_3$. The term "X'" indicates H, CN, NO$_2$, CF$_3$, SO$_2$R, or CO$_2$R.
Figure 46:
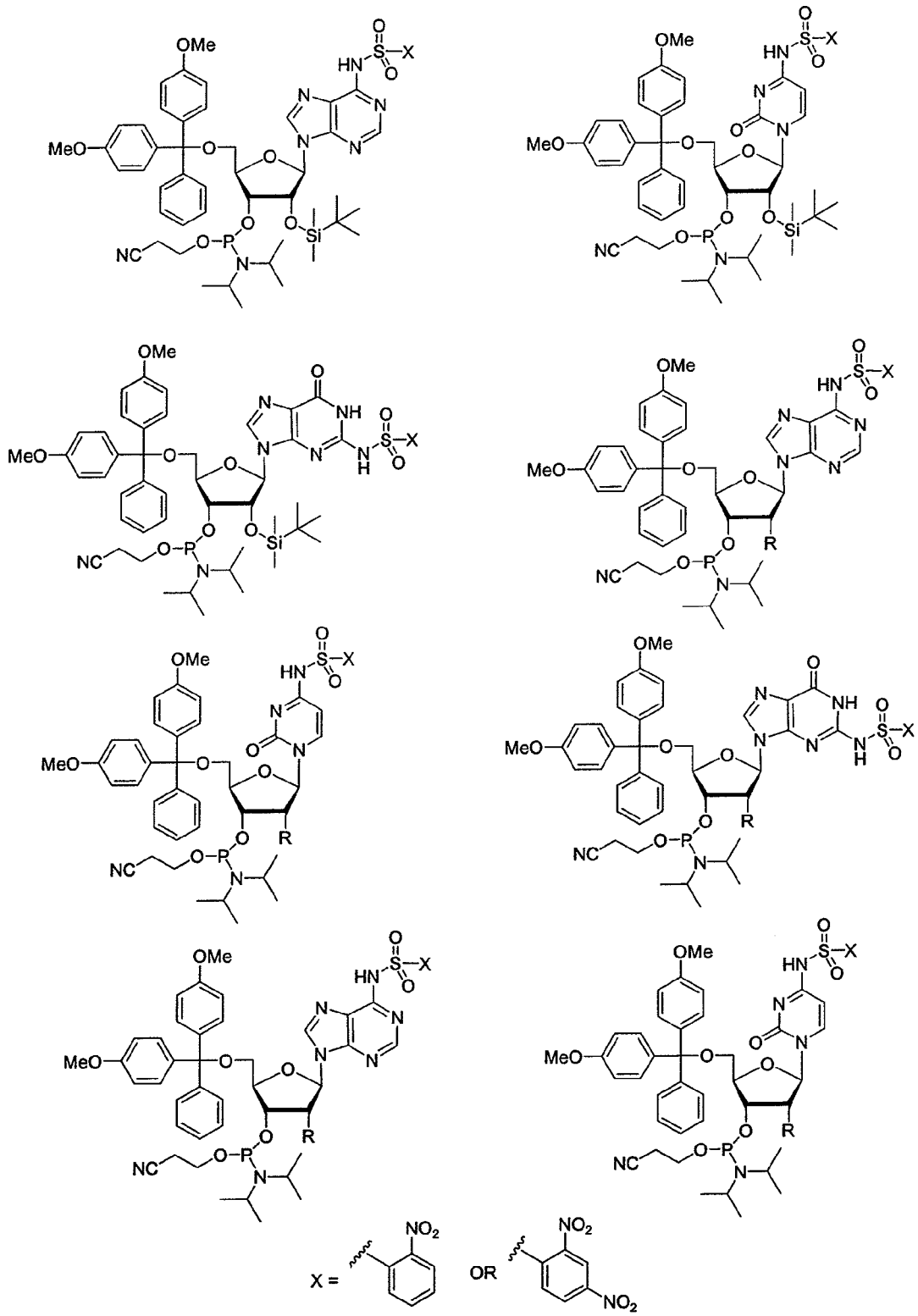
FIG. 46 depicts nucleosides bearing various base protecting groups amenable to the present invention. Note R is H, OMe, F, MOE, or TOM.
Figure 47:
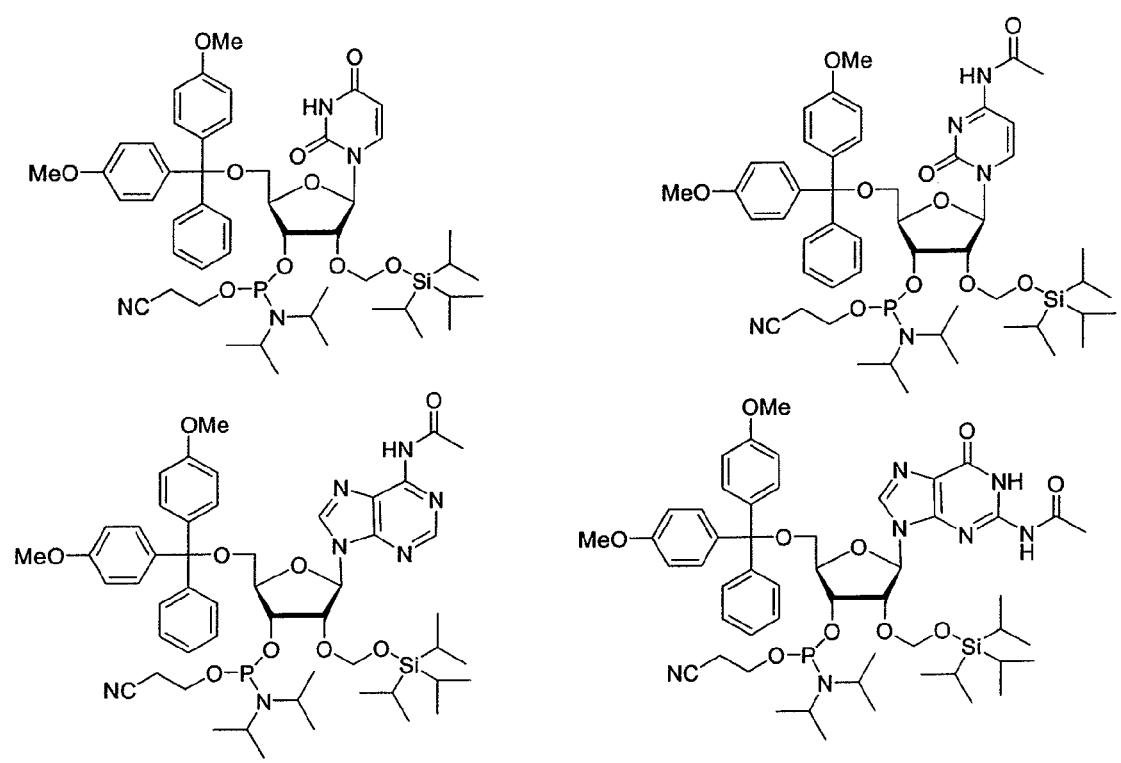
FIG. 47 depicts RNA building blocks amenable to the present invention, wherein the nucleoside has a TOM protecting group.
Figure 48:
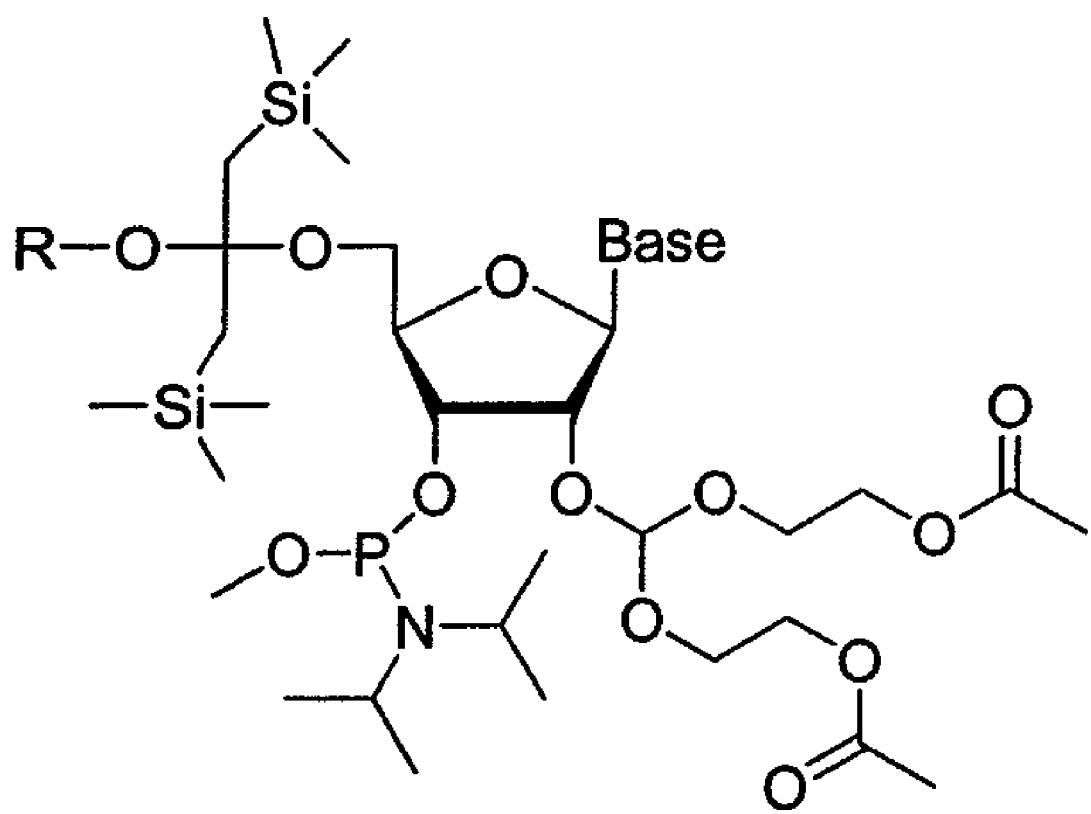
FIG. 48 depicts 5'-silyl protected RNA suitable for the silyl deprotection methods described herein. Note: Base is N-benzoyladenine, N-acetylcytosine, N-isoputyrylguanine, or uracil. R is cyclooctyl for guanosine and uridine. R is cyclododecyl for adenosine and cytidine. See Scaringe, S. A.; Wincott, F, E. and Caruthers, M. H. *J. Am. Chem. Soc.* 1998, 120, 11820-21.
Figure 49:
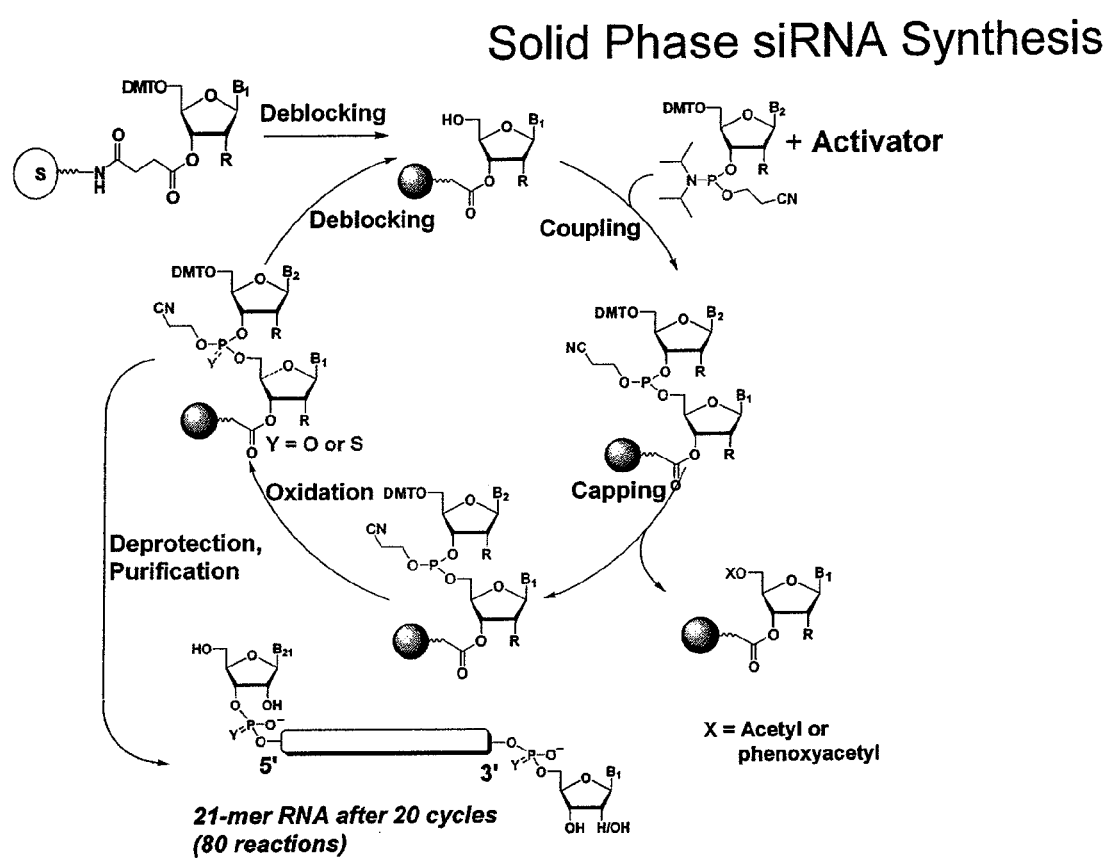
FIG. 49 depicts a general procedure for solid-phase RNA synthesis.

Another aspect of the present invention relates to protecting groups which can be removed enzymatically. Aralkyl esters represented by —$O_2CCH_2R$, wherein R is phenyl, pyridinyl, aniline, quinoline, or isoquinoline can be removed from the 2'-position of a nucleoside by enzymatic cleavage using penicillin G acylase. Representative examples of nucleosides bearing aralkyl ester protecting groups at the 2'-position of the ribose ring are presented in FIG. 45. In addition, certain internal amidites, including those shown in FIG. 45, can be removed by enzymatic cleavage.

One aspect of the present invention relates to a method of removing a protecting group, comprising the steps of:

admixing an optionally substituted ribose bearing a protecting group at the C2 position with an enzyme to produce an optionally substituted ribose bearing a hydroxyl group at the C2 position.

In certain embodiments, the present invention relates to the aforementioned method, wherein said protecting group is an aralkyl ester.

In certain embodiments, the present invention relates to the aforementioned method, wherein said protecting group is represented by the formula —$O_2CCH_2R$, wherein R is phenyl, pyridinyl, aniline, quinoline, or isoquinoline.

In certain embodiments, the present invention relates to the aforementioned method, wherein said enzyme is penicillin G acylase.

In certain embodiments, the present invention relates to the aforementioned method, wherein said ribose is a ribonucleotide oligomer.

Synthesis of Oligonucleotides Containing a TT Unit

In certain embodiments, it is preferable to prepare an oligonucleotide comprising two adjacent thymidine nucleotides. In a more preferred embodiment, the thymidine nucleotides are located at the 3' end of the oligonucleotide. The thymidine-thymidine (TT) nucleotide unit can be prepared using solution-phase chemistry, and then the TT unit is attached to a solid support. In certain embodiments, the TT unit is linked via a phosphorothioate group. In certain instances, the different stereoisomers of the phosphorothioate TT unit may be separated prior to attachment of the TT unit to the solid support. The remainder of the oligonucleotide strand can be synthesized via standard solid-phase synthesis techniques using the TT-support bound unit as a primer. In certain instances, the thymidine-thymidine nucleotide unit is made of deoxythymidine residues.

One aspect of the present invention relates to a method of preparing an oligonucleotide comprising a dinucleoside unit, comprising the steps of:

synthesizing a dinucleoside group via solution-phase chemistry, attaching said dinucleoside group to a solid support to form a primer, adding additional nucleotides to said primer using solid-phase synthesis techniques.

In certain embodiments, the present invention relates to the aforementioned method, wherein each nucleoside residue of said dinucleoside group is independently a natural or unnatural nucleoside.

In certain embodiments, the present invention relates to the aforementioned method, wherein said dinucleoside group comprises two nucleoside residues each independently comprising a sugar and a nucleobase, wherein said sugar is a D-ribose or D-deoxyribose, and said nucleobase is natural or unnatural.

In certain embodiments, the present invention relates to the aforementioned method, wherein said dinucleoside group comprises two nucleoside residues each independently comprising a sugar and a nucleobase, wherein said sugar is an L-ribose or L-deoxyribose, and said nucleobase is natural or unnatural.

In certain embodiments, the present invention relates to the aforementioned method, wherein said dinucleoside group comprises two thymidine residues.

In certain embodiments, the present invention relates to the aforementioned method, wherein said dinucleoside group comprises two deoxythymidine residues.

In certain embodiments, the present invention relates to the aforementioned method, wherein said dinucleoside group comprises two 2'-modified 5-methyl uridine or uridine residues, wherein the 2'-modifications are 2'-O-TBDMS, 2'-OMe, 2'-F, 2'-O—CH2-CH2-O-Me, or 2'-O-alkylamino derivatives.

In certain embodiments, the present invention relates to the aforementioned method, wherein said dinucleoside group comprises a phosphorothioate linkage, phosphorodithioate linkage, alkyl phosphonate linkage, or boranophosphate linkage.

In certain embodiments, the present invention relates to the aforementioned method, wherein said dinucleoside group comprises a phosphorothioate linkage, alkyl phosphonate linkage, or boranophosphate linkage; and said dinucleoside group is a single stereoisomer at the phosphorus atom.

In certain embodiments, the present invention relates to the aforementioned method, wherein the linkage between the nucleoside residues of said dinucleoside group is a 3'-5' linkage.

In certain embodiments, the present invention relates to the aforementioned method, wherein the linkage between the nucleoside residues of said dinucleoside group is a 2'-5' linkage.

In certain embodiments, the present invention relates to the aforementioned method, wherein said dinucleoside group comprises two nucleoside residues each independently comprising a sugar and a nucleobase, wherein said sugar is a D-ribose or D-deoxyribose, and said nucleobase is natural or unnatural; and the linkage between the nucleoside residues of said dinucleotide group is unnatural and non-phosphate.

In certain embodiments, the present invention relates to the aforementioned method, wherein said dinucleoside group comprises two nucleoside residues each independently comprising a sugar and a nucleobase, wherein said sugar is an L-ribose or L-deoxyribose, and said nucleobase is natural or unnatural; and the linkage between the nucleoside residues of said dinucleotide group is MMI, amide linkage, or guanidinium linkage.

Improved Procedures for the Synthesis of Nucleosides, Nucleotides, and Oligonucleotides Importantly, any one of the above-mentioned improvements can be used alone with standard methods of preparing nucleosides, nucleotides, and oligonucleotides, or more than one of the above-mentioned improvements can be used together with standard methods of preparing nucleosides, nucleotides, and oligonucleotides. Furthermore, one of ordinary skill in the art can readily determine the optimal conditions for each of the improvements described above.

General Description of Oligonucleotides

As described above, the present invention relates to processes and reagents for oligonucleotide synthesis and purification. The following description is meant to briefly describe some of the major types and structural features of oligonucleotides. Importantly, the following section is only representative and not meant to limit the scope of the present invention.

Oligonucleotides can be made of ribonucleotides, deoxyribonucleotides, or mixtures of ribonucleotides and deoxyribonucleotides. The nucleotides can be natural or unnatural. Oligonucleotides can be single stranded or double stranded. Various modifications to the sugar, base, and phosphate components of oligonucleotides are described below. As defined here, oligonucleotides having modified backbones or internucleoside linkages include those that retain a phosphorus atom in the backbone and those that do not have a phosphorus atom in the backbone. For the purposes the invention, modified oligonucleotides that do not have a phosphorus atom in their intersugar backbone can also be considered to be oligonucleosides.

Specific oligonucleotide chemical modifications are described below. It is not necessary for all positions in a given compound to be uniformly modified, and in fact more than one of the following modifications may be incorporated in a single siRNA compound or even in a single nucleotide thereof.

Preferred modified internucleoside linkages or backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalklyphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free-acid forms are also included.

Representative United States patents that teach the preparation of the above phosphorus atom-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,625,050; and 5,697,248, each of which is herein incorporated by reference.

Preferred modified internucleoside linkages or backbones that do not include a phosphorus atom therein (i.e., oligonucleosides) have backbones that are formed by short chain alkyl or cycloalkyl intersugar linkages, mixed heteroatom and alkyl or cycloalkyl intersugar linkages, or one or more short chain heteroatomic or heterocyclic intersugar linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In other preferred oligonucleotide mimetics, both the sugar and the internucleoside linkage, i.e., the backbone, of the nucleoside units are replaced with novel groups. The nucleobase units are maintained for hybridization with an appropriate nucleic acid target compound. One such oligonucleotide, an oligonucleotide mimetic, that has been shown to have excellent hybridization properties, is referred to as a peptide nucleic acid (PNA). In PNA compounds, the sugar-backbone of an oligonucleotide is replaced with an amide-containing backbone, in particular an aminoethylglycine backbone. The nucleobases are retained and are bound directly or indirectly to atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science*, 1991, 254, 1497.

Some preferred embodiments of the present invention employ oligonucleotides with phosphorothioate linkages and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$—, and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Oligonucleotides may additionally or alternatively comprise nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C), and uracil (U). Modified nucleobases include other synthetic and natural nucleobases, such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine.

Further nucleobases include those disclosed in U.S. Pat. No. 3,687,808, those disclosed in the *Concise Encyclopedia Of Polymer Science And Engineering*, pages 858-859, Kroschwitz, J. I., ed. John Wiley & Sons, 1990, those disclosed by Englisch et al. *Angewandte Chemie, International Edition* 1991, 30, 613, and those disclosed by Sanghvi, Y. S., Chapter 15, *Antisense Research and Applications*, pages 289-302, Crooke, S. T. and Lebleu, B., ed., CRC Press, 1993. Certain of these nucleobases are particularly useful for increasing the binding affinity of the oligonucleotides of the invention. These include 5-substituted pyrimidines, 6-azapyrimidines and N-2, N-6 and O-6 substituted purines, including 2-aminopropyladenine, 5-propynyluracil and 5-propynylcytosine. 5-Methylcytosine substitutions have been shown to increase nucleic acid duplex stability by 0.6-1.2° C. (Id., pages 276-278) and are presently preferred base substitutions, even more particularly when combined with 2'-O-methoxyethyl sugar modifications.

Representative United States patents that teach the preparation of certain of the above-noted modified nucleobases as well as other modified nucleobases include, but are not limited to, the above noted U.S. Pat. No. 687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,681,941; and 5,808,027; all of which are hereby incorporated by reference.

The oligonucleotides may additionally or alternatively comprise one or more substituted sugar moieties. Preferred oligonucleotides comprise one of the following at the 2' position: OH; F; O—, S—, or N-alkyl, O—, S—, or N-alkenyl, or O, S—or N-alkynyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3]_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. a preferred modification includes 2'-methoxyethoxy [2'-O—CH$_2$CH$_2$OCH$_3$, also known as 2'-O-(2-methoxyethyl) or 2'-MOE] (Martin et al. *Helv. Chim. Acta* 1995, 78, 486), i.e., an alkoxyalkoxy group. a further preferred modification includes 2'-dimethylaminooxyethoxy, i.e., a O(CH$_2$)$_2$ON(CH$_3$)$_2$ group, also known as 2'-DMAOE, as described in U.S. Pat. No. 6,127,533, filed on Jan. 30, 1998, the contents of which are incorporated by reference.

Other preferred modifications include 2'-methoxy (2'-O—CH$_3$), 2'-O-methoxyethyl, 2'-aminopropoxy (2'-OCH$_2$CH$_2$CH$_2$NH$_2$) and 2'-fluoro (2'-F). Similar modifications may also be made at other positions on the oligonucleotide, particularly the 3' position of the sugar on the 3' terminal nucleotide or in 2'-5' linked oligonucleotides.

As used herein, the term "sugar substituent group" or "2'-substituent group" includes groups attached to the 2'-position of the ribofuranosyl moiety with or without an oxygen atom. Sugar substituent groups include, but are not limited to, fluoro, O-alkyl, O-alkylamino, O-alkylalkoxy, protected O-alkylamino, O-alkylaminoalkyl, O-alkyl imidazole and polyethers of the formula (O-alkyl)$_m$, wherein m is 1 to about 10. Preferred among these polyethers are linear and cyclic polyethylene glycols (PEGs), and (PEG)-containing groups, such as crown ethers and those which are disclosed by Ouchi et al. (Drug Design and Discovery 1992, 9:93); Ravasio et al. (*J. Org. Chem.* 1991, 56:4329); and Delgardo et. al. (*Critical Reviews in Therapeutic Drug Carrier Systems* 1992, 9:249), each of which is hereby incorporated by reference in its entirety. Further sugar modifications are disclosed by Cook (*Anti-Cancer Drug Design,* 1991, 6, 585-607). Fluoro, O-alkyl, O-alkylamino, O-alkyl imidazole, O-alkylaminoalkyl, and alkyl amino substitution is described in U.S. Pat. No. 6,166,197, entitled "Oligomeric Compounds having Pyrimidine Nucleotide(s) with 2' and 5' Substitutions," hereby incorporated by reference in its entirety.

Additional sugar substituent groups amenable to the present invention include 2'-SR and 2'-NR$_2$ groups, wherein each R is, independently, hydrogen, a protecting group or substituted or unsubstituted alkyl, alkenyl, or alkynyl. 2'-SR Nucleosides are disclosed in U.S. Pat. No. 5,670,633, issued Sep. 23, 1997, hereby incorporated by reference in its entirety. The incorporation of 2'-SR monomer synthons is disclosed by Hamm et al. (*J. Org. Chem.* 1997, 62, 3415-3420). 2'-NR nucleosides are disclosed by Goettingen, M. *J. Org. Chem.,* 1996, 61, 6273-6281; and Polushin et al. *Tetrahedron Lett.* 1996, 37, 3227-3230. Further representative 2'-substituent groups amenable to the present invention include those having one of formula I or II:

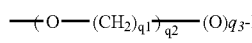

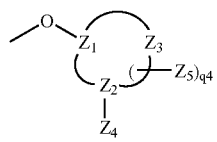

wherein,

E is C$_1$-C$_{10}$ alkyl, N(Q$_3$)(Q$_4$) or N═C(Q$_3$)(Q$_4$); each Q$_3$ and Q$_4$ is, independently, H, C$_1$-C$_{10}$ alkyl, dialkylaminoalkyl, a nitrogen protecting group, a tethered or untethered conjugate group, a linker to a solid support; or Q$_3$ and Q$_4$, together, form a nitrogen protecting group or a ring structure optionally including at least one additional heteroatom selected from N and O;

q$_1$ is an integer from 1 to 10;
q$_2$ is an integer from 1 to 10;
q$_3$ is 0 or 1;
q$_4$ is 0, 1 or 2;

each Z$_1$, Z$_2$ and Z$_3$ is, independently, C$_4$-C$_7$ cycloalkyl, C$_5$-C$_{14}$ aryl or C$_3$-C$_{15}$ heterocyclyl, wherein the heteroatom in said heterocyclyl group is selected from oxygen, nitrogen and sulfur;

Z$_4$ is OM$_1$, SM$_1$, or N(M$_1$)$_2$; each M$_1$ is, independently, H, C$_1$-C$_8$ alkyl, C$_1$-C$_8$ haloalkyl, C(═NH)N(H)M$_2$, C(═O)N(H)M$_2$ or OC(═O)N(H)M$_2$; M$_2$ is H or C$_1$-C$_8$ alkyl; and Z$_5$ is C$_1$-C$_{10}$ alkyl, C$_1$-C$_{10}$ haloalkyl, C$_2$-C$_{10}$ alkenyl, C$_2$-C$_{10}$ alkynyl, C$_6$-C$_{14}$ aryl, N(Q$_3$)(Q$_4$), OQ$_3$, halo, SQ$_3$ or CN.

Representative 2'-O-sugar substituent groups of formula I are disclosed in U.S. Pat. No. 6,172,209, entitled "Capped 2'-Oxyethoxy Oligonucleotides," hereby incorporated by reference in its entirety. Representative cyclic 2'-O-sugar substituent groups of formula II are disclosed in U.S. Pat. No. 6,271,358, filed Jul. 27, 1998, entitled "RNA Targeted 2'-Modified Oligonucleotides that are Conformationally Preorganized," hereby incorporated by reference in its entirety.

Sugars having O-substitutions on the ribosyl ring are also amenable to the present invention. Representative substitutions for ring O include, but are not limited to, NH, NR, S, CH$_2$, CHF, and CF$_2$. See, e.g., Secrist et al., Abstract 21, *Program & Abstracts, Tenth International Roundtable, Nucleosides, Nucleotides and their Biological Applications*, Park City, Utah, Sep. 16-20, 1992.

Oligonucleotides may also have sugar mimetics, such as cyclobutyl moieties, hexoses, cyclohexenyl in place of the pentofuranosyl sugar. Representative United States patents that teach the preparation of such modified sugars structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,0531 5,639,873; 5,646,265; 5,658,873; 5,670,633; 5,700,920; and 5,859,221, all of which are hereby incorporated by reference.

Additional modifications may also be made at other positions on the oligonucleotide, particularly the 3' position of the sugar on the 3' terminal nucleotide. For example, one modification of oligonucleotides involves chemically linking to the oligonucleotide one or more additional moieties or conjugates which enhance the activity, cellular distribution or cellular uptake of the oligonucleotide. Such moieties include but are not limited to lipid moieties, such as a cholesterol moiety (Letsinger et al., *Proc. Natl. Acad. Sci. USA,* 1989, 86, 6553), cholic acid (Manoharan et al., *Bioorg. Med. Chem. Lett.,* 1994, 4, 1053), a thioether, e.g., hexyl-5-tritylthiol (Manoharan et al., *Ann. N.Y. Acad. Sci.,* 1992, 660, 306; Manoharan et al., *Bioorg. Med. Chem. Let.,* 1993, 3, 2765), a thiocholesterol (Oberhauser et al., *Nucl. Acids Res.,* 1992, 20, 533), an aliphatic chain, e.g., dodecandiol or undecyl residues (Saison-Behmoaras et al., *EMBO J.,* 1991, 10, 111; Kabanov et al., *FEBS Lett.,* 1990, 259, 327; Svinarchuk et al., *Biochimie,* 1993, 75, 49), a phospholipid, e.g., di-hexadecyl-rac-glycerol or triethylammonium 1,2-di-O-hexadecyl-rac-glycero-3-H-phosphonate (Manoharan et al., *Tetrahedron Lett.,* 1995, 36, 3651; Shea et al., *Nucl. Acids Res.,* 1990, 18, 3777), a polyamine or a polyethylene glycol chain (Manoharan et al., *Nucleosides & Nucleotides,* 1995, 14, 969), or adamantane acetic acid (Manoharan et al., *Tetrahedron Lett.,* 1995, 36, 3651), a palmityl moiety (Mishra et al., *Biochim. Biophys.*

*Acta*, 1995, 1264, 229), or an octadecylamine or hexylaminocarbonyl-oxycholesterol moiety (Crooke et al., *J. Pharmacol. Exp. Ther.*, 1996, 277, 923).

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928; and 5,688,941, each of which is herein incorporated by reference.

Oligonucleotides can be substantially chirally pure with regard to particular positions within the oligonucleotides. Examples of substantially chirally pure oligonucleotides include, but are not limited to, those having phosphorothioate linkages that are at least 75% Sp or Rp (Cook et al., U.S. Pat. No. 5,587,361) and those having substantially chirally pure (Sp or Rp) alkylphosphonate, phosphoramidate or phosphotriester linkages (Cook, U.S. Pat. Nos. 5,212,295 and 5,521, 302).

Synthetic RNA molecules and derivatives thereof that catalyze highly specific endoribonuclease activities are known as ribozymes. (See, generally, U.S. Pat. No. 5,543,508 to Haseloff et al., issued Aug. 6, 1996, and U.S. Pat. No. 5,545, 729 to Goodchild et al., issued Aug. 13, 1996.) The cleavage reactions are catalyzed by the RNA molecules themselves. In naturally occurring RNA molecules, the sites of self-catalyzed cleavage are located within highly conserved regions of RNA secondary structure (Buzayan et al., *Proc. Natl. Acad. Sci. U.S.A.*, 1986, 83, 8859; Forster et al., *Cell*, 1987, 50, 9). Naturally occurring autocatalytic RNA molecules have been modified to generate ribozymes which can be targeted to a particular cellular or pathogenic RNA molecule with a high degree of specificity. Thus, ribozymes serve the same general purpose as antisense oligonucleotides (i.e., modulation of expression of a specific gene) and, like oligonucleotides, are nucleic acids possessing significant portions of single-strandedness. That is, ribozymes have substantial chemical and functional identity with oligonucleotides and are thus considered to be equivalents for purposes of the present invention.

In certain instances, the oligonucleotide may be modified by a moiety. A number of moieties have been conjugated to oligonucleotides in order to enhance the activity, cellular distribution or cellular uptake of the oligonucleotide, and procedures for performing such conjugations are available in the scientific literature. Such moieties have included lipid moieties, such as cholesterol (Letsinger et al., *Proc. Natl. Acad. Sci. USA*, 1989, 86:6553), cholic acid (Manoharan et al., *Bioorg. Med. Chem. Lett.*, 1994, 4:1053), a thioether, e.g., hexyl-S-tritylthiol (Manoharan et al., *Ann. N.Y. Acad. Sci.*, 1992, 660:306; Manoharan et al., *Bioorg. Med. Chem. Let.*, 1993, 3:2765), a thiocholesterol (Oberhauser et al., *Nucl. Acids Res.*, 1992, 20:533), an aliphatic chain, e.g., dodecandiol or undecyl residues (Saison-Behmoaras et al., *EMBO J.*, 1991, 10:111; Kabanov et al., *FEBS Lett.*, 1990, 259:327; Svinarchuk et al., *Biochimie*, 1993, 75:49), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36:3651; Shea et al., *Nucl. Acids Res.*, 1990, 18:3777), a polyamine or a polyethylene glycol chain (Manoharan et al., *Nucleosides & Nucleotides*, 1995, 14:969), or adamantane acetic acid (Manoharan et al., *Tetrahedron Lett.*, 1995, 36:3651), a palmityl moiety (Mishra et al., *Biochim. Biophys. Acta*, 1995, 1264:229), or an octadecylamine or hexylamino-carbonyl-oxycholesterol moiety (Crooke et al., *J. Pharmacol. Exp. Ther.*, 1996, 277:923). Representative United States patents that teach the preparation of such oligonucleotide conjugates have been listed above. Typical conjugation protocols involve the synthesis of oligonucleotides bearing an aminolinker at one or more positions of the sequence. The amino group is then reacted with the molecule being conjugated using appropriate coupling or activating reagents. The conjugation reaction may be performed either with the oligonucleotide still bound to the solid support or following cleavage of the oligonucleotide in solution phase. Purification of the oligonucleotide conjugate by HPLC typically affords the pure conjugate.

One type of double-stranded RNA is short interfering RNA (siRNA). In certain embodiments, the backbone of the oligonucleotide can be modified to improve the therapeutic or diagnostic properties of the siRNA compound. The two strands of the siRNA compound can be complementary, partially complementary, or chimeric oligonucleotides. In certain embodiments, at least one of the bases or at least one of the sugars of the oligonucleotide has been modified to improve the therapeutic or diagnostic properties of the siRNA compound.

The siRNA agent can include a region of sufficient homology to the target gene, and be of sufficient length in terms of nucleotides, such that the siRNA agent, or a fragment thereof, can mediate down regulation of the target gene. It will be understood that the term "ribonucleotide" or "nucleotide" can, in the case of a modified RNA or nucleotide surrogate, also refer to a modified nucleotide, or surrogate replacement moiety at one or more positions. Thus, the siRNA agent is or includes a region which is at least partially complementary to the target RNA. In certain embodiments, the siRNA agent is fully complementary to the target RNA. It is not necessary that there be perfect complementarity between the siRNA agent and the target, but the correspondence must be sufficient to enable the siRNA agent, or a cleavage product thereof, to direct sequence specific silencing, such as by RNAi cleavage of the target RNA. Complementarity, or degree of homology with the target strand, is most critical in the antisense strand. While perfect complementarity, particularly in the antisense strand, is often desired some embodiments can include one or more but preferably 6, 5, 4, 3, 2, or fewer mismatches with respect to the target RNA. The mismatches are most tolerated in the terminal regions, and if present are preferably in a terminal region or regions, e.g., within 6, 5, 4, or 3 nucleotides of the 5' and/or 3' terminus. The sense strand need only be sufficiently complementary with the antisense strand to maintain the over all double-strand character of the molecule.

In addition, an siRNA agent will often be modified or include nucleoside surrogates. Single stranded regions of an siRNA agent will often be modified or include nucleoside surrogates, e.g., the unpaired region or regions of a hairpin structure, e.g., a region which links two complementary regions, can have modifications or nucleoside surrogates. Modification to stabilize one or more 3'- or 5'-terminus of an iRNA agent, e.g., against exonucleases, or to favor the antisense sRNA agent to enter into RISC are also favored. Modifications can include C3 (or C6, C7, C12) amino linkers, thiol linkers, carboxyl linkers, non-nucleotidic spacers (C3, C6, C9, C12, abasic, triethylene glycol, hexaethylene glycol), special biotin or fluorescein reagents that come as phosphoramidites and that have another DMT-protected hydroxyl group, allowing multiple couplings during RNA synthesis.

siRNA agents include: molecules that are long enough to trigger the interferon response (which can be cleaved by Dicer (Bernstein et al. 2001. Nature, 409:363-366) and enter a RISC (RNAi-induced silencing complex)); and, molecules which are sufficiently short that they do not trigger the interferon response (which molecules can also be cleaved by Dicer and/or enter a RISC), e.g., molecules which are of a size which allows entry into a RISC, e.g., molecules which resemble Dicer-cleavage products. Molecules that are short enough that they do not trigger an interferon response are termed sRNA agents or shorter iRNA agents herein. "sRNA agent or shorter iRNA agent" as used refers to an iRNA agent that is sufficiently short that it does not induce a deleterious interferon response in a human cell, e.g., it has a duplexed region of less than 60 but preferably less than 50, 40, or 30 nucleotide pairs. The sRNA agent, or a cleavage product thereof, can down regulate a target gene, e.g., by inducing RNAi with respect to a target RNA, preferably an endogenous or pathogen target RNA.

Each strand of a sRNA agent can be equal to or less than 30, 25, 24, 23, 22, 21, 20, 19, 18, 17, 16, or 15 nucleotides in length. The strand is preferably at least 19 nucleotides in length. For example, each strand can be between 21 and 25 nucleotides in length. Preferred sRNA agents have a duplex region of 17, 18, 19, 29, 21, 22, 23, 24, or 25 nucleotide pairs, and one or more overhangs, preferably one or two 3' overhangs, of 2-3 nucleotides.

In addition to homology to target RNA and the ability to down regulate a target gene, an siRNA agent will preferably have one or more of the following properties:

(1) it will, despite modifications, even to a very large number, or all of the nucleosides, have an antisense strand that can present bases (or modified bases) in the proper three dimensional framework so as to be able to form correct base pairing and form a duplex structure with a homologous target RNA which is sufficient to allow down regulation of the target, e.g., by cleavage of the target RNA;

(2) it will, despite modifications, even to a very large number, or all of the nucleosides, still have "RNA-like" properties, i.e., it will possess the overall structural, chemical and physical properties of an RNA molecule, even though not exclusively, or even partly, of ribonucleotide-based content. For example, an siRNA agent can contain, e.g., a sense and/or an antisense strand in which all of the nucleotide sugars contain e.g., 2' fluoro in place of 2' hydroxyl. This deoxyribonucleotide-containing agent can still be expected to exhibit RNA-like properties. While not wishing to be bound by theory, the electronegative fluorine prefers an axial orientation when attached to the C2' position of ribose. This spatial preference of fluorine can, in turn, force the sugars to adopt a $C_{3'}$-endo pucker. This is the same puckering mode as observed in RNA molecules and gives rise to the RNA-characteristic A-family-type helix. Further, since fluorine is a good hydrogen bond acceptor, it can participate in the same hydrogen bonding interactions with water molecules that are known to stabilize RNA structures. Generally, it is preferred that a modified moiety at the 2' sugar position will be able to enter into H-bonding which is more characteristic of the OH moiety of a ribonucleotide than the H moiety of a deoxyribonucleotide. A preferred siRNA agent will: exhibit a $C_{3'}$-endo pucker in all, or at least 50, 75, 80, 85, 90, or 95% of its sugars; exhibit a $C_{3'}$-endo pucker in a sufficient amount of its sugars that it can give rise to a the RNA-characteristic A-family-type helix; will have no more than 20, 10, 5, 4, 3, 2, or 1 sugar which is not a $C_{3'}$-endo pucker structure.

A "single strand iRNA agent" as used herein, is an iRNA agent which is made up of a single molecule. It may include a duplexed region, formed by intra-strand pairing, e.g., it may be, or include, a hairpin or pan-handle structure. Single strand iRNA agents are preferably antisense with regard to the target molecule. A single strand iRNA agent should be sufficiently long that it can enter the RISC and participate in RISC mediated cleavage of a target mRNA. A single strand iRNA agent is at least 14, and more preferably at least 15, 20, 25, 29, 35, 40, or 50 nucleotides in length. It is preferably less than 200, 100, or 60 nucleotides in length.

Hairpin iRNA agents will have a duplex region equal to or at least 17, 18, 19, 29, 21, 22, 23, 24, or 25 nucleotide pairs. The duplex region will preferably be equal to or less than 200, 100, or 50, in length. Preferred ranges for the duplex region are 15-30, 17 to 23, 19 to 23, and 19 to 21 nucleotides pairs in length. The hairpin will preferably have a single strand overhang or terminal unpaired region, preferably the 3', and preferably of the antisense side of the hairpin. Preferred overhangs are 2-3 nucleotides in length.

Chimeric oligonucleotides, or "chimeras," are oligonucleotides which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. Consequently, comparable results can often be obtained with shorter oligonucleotides when chimeric oligonucleotides are used, compared to phosphorothioate oligodeoxynucleotides. Chimeric oligonucleotides of the invention may be formed as composite structures of two or more oligonucleotides, modified oligonucleotides, oligonucleosides and/or oligonucleotide mimetics as described above. Such oligonucleotides have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; 5,700,922; and 5,955,589, each of which is herein incorporated by reference. In certain embodiments, the chimeric oligonucleotide is RNA-DNA, DNA-RNA, RNA-DNA-RNA, DNA-RNA-DNA, or RNA-DNA-RNA-DNA, wherein the oligonucleotide is between 5 and 60 nucleotides in length.

Definitions

For convenience, certain terms employed in the specification, examples, and appended claims are collected here.

The term "heteroatom" as used herein means an atom of any element other than carbon or hydrogen. Preferred heteroatoms are boron, nitrogen, oxygen, phosphorus, sulfur and selenium.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$-$C_{30}$ for straight chain, $C_3$-$C_{30}$ for branched chain), and more preferably 20 or fewer. Likewise, preferred cycloalkyls have from 3-10 carbon atoms in their ring structure, and more preferably have 5, 6 or 7 carbons in the ring structure.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aralkyl", as used herein, refers to an alkyl group substituted with an aryl group (e.g., an aromatic or heteroaromatic group). For example, a benzyl group ($PhCH_2$—) is an aralkyl group.

The terms "alkenyl" and "alkynyl" refer to unsaturated aliphatic groups analogous in length and possible substitution to the alkyls described above, but that contain at least one double or triple bond respectively.

The term "aryl" as used herein includes 5-, 6- and 7-membered single-ring aromatic groups that may include from zero to four heteroatoms, for example, benzene, anthracene, naphthalene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The terms "amine" and "amino" are art-recognized and refer to both unsubstituted and substituted amines, e.g., a moiety that can be represented by the general formula:

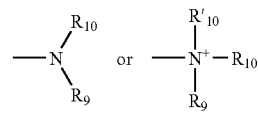

wherein $R_9$, $R_{10}$ and $R'_{10}$ each independently represent a group permitted by the rules of valence.

The term "acylamino" is art-recognized and refers to a moiety that can be represented by the general formula:

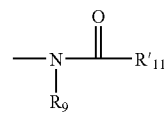

wherein $R_9$ is as defined above, and $R'_{11}$ represents a hydrogen, an alkyl, an alkenyl or —$(CH_2)_m$—$R_8$, where m and $R_8$ are as defined above.

The term "amido" is art recognized as an amino-substituted carbonyl and includes a moiety that can be represented by the general formula:

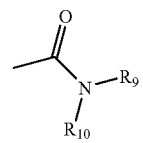

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein m and $R_8$ are defined above. Representative alkylthio groups include methylthio, ethyl thio, and the like.

The term "carbonyl" is art recognized and includes such moieties as can be represented by the general formula:

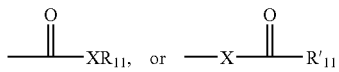

wherein X is a bond or represents an oxygen or a sulfur, and $R_{11}$ represents a hydrogen, an alkyl, an alkenyl, —$(CH_2)_m$—$R_8$ or a pharmaceutically acceptable salt, $R'_{11}$ represents a hydrogen, an alkyl, an alkenyl or —$(CH_2)_m$—$R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

The term "sulfonate" is art recognized and includes a moiety that can be represented by the general formula:

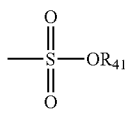

in which $R_{41}$ is an electron pair, hydrogen, alkyl, cycloalkyl, or aryl.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled Standard List of Abbreviations. The abbreviations contained in said list, and all abbreviations utilized by organic chemists of ordinary skill in the art are hereby incorporated by reference.

The term "sulfate" is art recognized and includes a moiety that can be represented by the general formula:

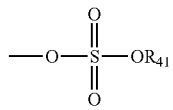

in which $R_{41}$ is as defined above.

The term "sulfonylamino" is art recognized and includes a moiety that can be represented by the general formula:

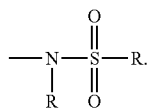

The term "sulfamoyl" is art-recognized and includes a moiety that can be represented by the general formula:

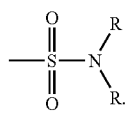

The term "sulfonyl", as used herein, refers to a moiety that can be represented by the general formula:

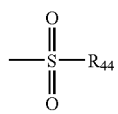

in which $R_{44}$ is selected from the group consisting of hydrogen, alkyl, alkenyl, alkynyl, cycloalkyl, heterocyclyl, aryl, or heteroaryl.

The term "sulfoxido" as used herein, refers to a moiety that can be represented by the general formula:

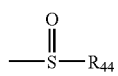

in which $R_{44}$ is selected from the group consisting of hydrogen, alkyl, alkenyl, alkynyl, cycloalkyl, heterocyclyl, aralkyl, or aryl.

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—$R_7$, m and $R_7$ being defined above.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g. alkyl, m, n, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. In addition, the substituent can be halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, and the like. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991).

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g., functioning as analgesics), wherein one or more simple variations of substituents are made which do not adversely affect the efficacy of the compound in binding to sigma receptors. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986-87, inside cover.

EXEMPLIFICATION

The invention now being generally described, it will be more readily understood by reference to the following examples, which are included merely for purposes of illustration of certain aspects and embodiments of the present invention, and are not intended to limit the invention.

Example 1

Oligonucleotide Synthesis Using Phosphoramidite Activators 35-48 (see FIGS. 1-3)

In certain instances the strength of the activator is increased by forming the activated salt resulting in decreased coupling time for RNA Synthesis.

A decamer RNA molecules (49, 5'-CAUCGCTGAdT-3' SEQ ID NO: 7) was synthesized on a 394 ABI machine (ALN 0208) using the standard 98 step cycle written by the manufacturer with modifications to a few wait steps as described below. The solid support was controlled pore glass (CPG, prepacked, 1 μmole, 500Å, Proligo Biochemie GmbH) and the monomers were RNA phosphoramidites with fast deprotecting groups obtained from Pierce Nucleic Acid Technologies used at concentrations of 0.15 M in acetonitrile ($CH_3CN$) unless otherwise stated. Specifically the RNA phosphoramidites were 5'-O-Dimethoxytrityl- $N_6$-phenoxyacetyl-2'-O-tbutyldimethylsilyl-adenosine-3'-O-(β-cyanoethyl-N,N'-diisopropyl) phosphoramidite, 5'-O-Dimethoxytrityl- $N^2$-p-isopropylphenoxyacetyl-2'-O-tbutyldimethylsilyl-guanosine-3'-O-(β-cyanoethyl-N,N'-diisopropyl) phosphoramidite, 5'-O-Dimethoxytrityl- $N^4$-acetyl-2'O-tbutyldimethylsilyl-cytidine-3'-O-(β-cyanoethyl-N,N'-diisopropyl)phosphoramidite, and 5'-O-Dimethoxytrityl-2'-O-tbutyldimethylsilyl-uridine-3'-O-(β-cyanoethyl-N,N'-diisopropyl)-phosphoramidite;

The coupling times were either 1, 3 or 5 minutes for the different salt concentrations which themselves were 10, 20 and 40 mol % relative to the 5-(ethylthio)-1H-tetrazole (ETT, 0.25 M, Glen Research). Diisopropylammonium salt of ETT with required mol % was obtained by adding calculated amount of anhydrous diisopropylamine to 0.25 M ETT solution and stored over molecular sieves for 4-6 h. Details of the other reagents are as follows: Cap A: 5% Phenoxyacetic anhydride/THF/pyridine, (Glen Research, & Cap B:10% N-methylimidazole/THF, (Glen Research); Oxidant 0.02 M Iodine in THF/Water/Pyridine (Glen Research] Detritylation was achieved with 3% TCA/dichloromethane (Proligo).

After completion of synthesis the CPG was transferred to a screw cap RNase free microfuge tube. The oligonucleotide was cleaved from the CPG with simultaneous deprotection of base and phosphate groups with 1.0 mL of a mixture of 40% methylamine:ammonia (1:1)] for 30 minutes at 65° C. The solution was then lyophilized to dryness.

Example 2

Synthesis of Compound 1 (R'=H and R"=C(S)OEt or R',R"=H)

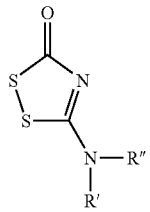

A solution of chlorocarbonyl sulfenyl chloride (8.4 mL, 0.1 mol) in dry ether (50 mL) was added dropwise to a cold solution of thiourea (7.62 g, 0.1 mol) in dry ether (500 mL) and triethylamine (14 mL, 0.1 mol) cooled with ice-bath in 3 h under an argon atmosphere. The reaction mixture was stirred at the same temperature for total of 6 h. The solids were filtered off and the filtration was concentrated into a crude residue which was further crystallized with dichloromethane-hexanes to give a pure compound (2.5 g). The mother liquid was then concentrated into a crude residue which was applied to a column of silica gel eluted with dichloromethane-methanol (40:1) to give a pure compound (180 mg). The total yield is about 30%. $^1$H-NMR (CDCl$_3$, 400 MHz): δ 10.46 (br, 1 H), 4.38 (q, 2 H, J=6.8, 14.4 Hz, CH$_2$), 1.39 (t, 3 H, J=7.2 Hz, CH$_3$). $^{13}$C-NMR (CDCl$_3$, 100 MHz): 181.01, 177.00, 153.75, 64.68, 14.32.

Example 3

Phosphorothioation of Di- and Poly-Oligothymidine Using Sulfur Transfer Reagent 1 (R'=H and R"=C(S)OEt or R',R"=H)

Dinucleotide 2 and hexamer 3 were synthesized on a 394 ABI machine using the standard 93 step cycle written by the manufacturer with modifications to a few wait steps as described below. Activator used was 5-(ethylthio)-1H-tetrazole (0.25 M), and for PS-oxidation, 0.05 M 1 in anhydrous acetonitrile was used. The sulfurization time was about 4 min. After completion of the synthesis, 2 and 3 were deprotected from support by aqueous ammonia treatment at 55° C. for 1 h. After HPLC purification, the compound were analysed by LC-MS.

The results of phosphorothioation of oligothymdine using 1 as the sulfur-transfer agent are shown below.

| Compound | Sequence, all P = S | Mass Calc. | Mass Found |
|---|---|---|---|
| 2 | 5' TT 3' | 562.46 | 562.22 |
| 3 | 5' TTTTTT 3' | 1843.52 | 1842.05 |

Example 4

Medium/Large Scale Oligonucleotides Synthesis with P=O, P=S and P=O/P=S Mixed Backbone A. Solid Phase Synthesis of Sequences 23 with P=O Backbone and 24 with P=S Backbone 200 μmole syntheses were performed on the ÅKTA Oligo-Pilot 100 in 6.3 mL columns using 500 Å dT-CPG loaded at 97 μmole/g (Prime Synthesis; Aston, Pa.) Detritylation was performed with 3% dichloroacetic acid (DCA) in dichloromethane (CH$_2$Cl$_2$.) Coupling was accomplished with 2 eq. of DNA 3'-β-cyanoethylphosphoramidites (CEP) or 2.5 eq. RNA 3'-β-cyanoethylphosphoramidites (Pierce Nucleic Acids; Milwaukee, Wis.) used at 0.2 M in acetonitrile (MeCN). Activator was 0.6 M 5-Ethylthiotetrazole (American International Chemical; Natick, Mass.) in MeCN and was used at three-fold excess relative to RNA CEPs and at 4.5-fold excess to DNA CEPs. Oxidation was via 50 mM I2 in 90% pyridine 10% H$_2$O or with 0.05 M 3-ethoxy-1,2,4-dithiazolidine-5-one (EDITH) in MeCN (Q. Xu, et al. *Nucleic Acids Research*, Vol. 24, No. 18, pp. 3643-3644). Capping was with 10% acetic anhydride (Ac$_2$O) 10% 1-methylimidazole (1-MeIm) 15% 2,6-lutidine in MeCN.

After synthesis, support was deblocked in 25 mL 40% methylamine (MeNH$_2$) in H$_2$O for 20 minutes at 60° C. and 200 rpm, then chilled in dry ice [CO$_2$(s)] and the support filtered off in a sintered glass funnel and rinsed with 75 mL dimethylsulfoxide (DMSO) added to the filtrate. To this solution was added 25 mL triethylammonium trihydrofluoride (TEA.3HF, TREAT) followed by heating to 60° C. for 20 minutes at 200 rpm. After chilling in CO$_2$(s) this solution was diluted with 125 mL 20 mM sodium acetate (NaOAc) and pH 6 confirmed. If necessary, pH was adjusted with HCl.

Analysis was performed on an Agilent 1100 series HPLC using a Dionex 4×250 mm DNAPak column. Buffer A was 1 mM EDTA, 25 mM Tris pH 8, 20 mM NaClO$_4$. Buffer B was 1 mM EDTA, 25 mM Tris pH 8, 0.4 M NaClO$_4$. Separation was performed on a 0-40% B gradient with buffers and column heated to 65° C.

Materials were purified on an ÅKTA Explorer equipped with a XK26/10 column (Amersham Biosciences; Piscataway, N.J.) packed to a bed height of 10 cm with Hi Load Q Sepharose. Buffer A was 1 mM EDTA, 25 mM Tris pH 8. Buffer B was 1 mM EDTA, 25 mM Tris pH8, 0.4 M NaClO$_4$. Crude materials were diluted 4-6 fold with H$_2$O and loaded. Pooled purified material=8.1 kAU at 96% by ion exchange (IEX).

The solutions containing the crude material were diluted 4-6 fold, loaded onto the column in 1-3kAU amounts at 10 mL/min and eluted with a segmented gradient from 0-60% B. Appropriate fractions were pooled and this pooled material desalted in 30 mL amounts over Sephadex G-25 on a BioPilot column (6 cm dia.×7.5 cm) against H$_2$O. The eluate was vacuum evaporated to less than 25 mL, shell frozen and lyophilized.

The results from the synthesis of 23 and 24 are presented below. Note that purification was performed on an ÅKTA Explorer and that "nd" indicates that the value was not determined.

| Sequence | Thiolation Agent | Quantity | crude % Y | %fl | IEX Purification |
|---|---|---|---|---|---|
| 23 | — | — | 43 | nd | 8.6 kAU @ 94% fl |
| 24 | 0.05 M EDITH | 1CV in 1 min. | 42 | 71 | 8.1 kAU (=48% of crude) @ 96% fl |

23 = 5'-GCGGAUCAAACCUCACCAAdTdT-3' (SEQ ID NO: 3)
24 = 5'-UUGGUGAGGUUUGAUCCGCdTdT-3' (SEQ ID NO: 4)

B. Solid Phase Synthesis of Mixed Phosphorothioate-phosphodiester Oligoribonucleotides Using Phenyl Acetyl Disulfide or 3-ethoxy-1,2,4-dithiazoline-5-one 200 μmole syntheses were performed on the ÅKTA Oligo-Pilot 100 in 6.3 mL columns using 500 Å dT-CPG loaded at 97 μmole/g (Prime Synthesis; Aston, Pa.) Detritylation was performed with 3% dichloroacetic acid (DCA) in dichloromethane ($CH_2Cl_2$.) Coupling was accomplished with 2 eq. of DNA CEPs or 2.5 eq. of RNA CEPs (Pierce Nucleic Acids; Milwaukee, Wis.) used at 0.2 M in acetonitrile (MeCN.) Activator was 0.6 M 5-Ethylthiotetrazole (American International Chemical; Natick, Mass.) in MeCN and was used at threefold excess relative to RNA CEPs and at 4.5-fold excess to DNA CEPs. Oxidation was via 50 mM $I_2$ in 90% pyridine 10% $H_2O$. Thiolation was with 0.2 M phenyl acetyl disulfide (PADS) in 1:1 3-picoline:MeCN or with 0.05 M 3-ethoxy-1,2,4-dithiazolidine-5-one (EDITH) in MeCN (Q. Xu, et al. *Nucleic Acids Research*, Vol. 24, No. 18, pp. 3643-3644.) Capping was with 10% acetic anhydride ($Ac_2O$) 10% 1-methylimidazole (1-MeIm) 15% 2,6-lutidine in MeCN. When EDITH was used, capping was performed both before and after the thiolation reaction (M. Ma, et al. *Nucleic Acids Research*, 1997, Vol. 25, No. 18, pp. 3590-3593).

After synthesis, support was deblocked in 25 mL 40% methylamine ($MeNH_2$) in $H_2O$ for 20 minutes at 60° C. and 200 rpm, then chilled in dry ice [$CO_2$(s)] and the support filtered off in a sintered glass funnel and rinsed with 75 mL dimethylsulfoxide (DMSO) added to the filtrate. To this solution was added 25 mL triethylammonium trihydrofluoride (TEA.3HF, TREAT) followed by heating to 60° C. for 20 minutes at 200 rpm. After chilling in $CO_2$(s) this solution was diluted with 125 mL 20 mM sodium acetate (NaAc) and pH 6 confirmed. If necessary, pH was adjusted with HCl.

Analysis was performed on an Agilent 1100 series HPLC using a Dionex 4×250 mm DNAPak column. Buffer A was 1 mM EDTA, 25 mM Tris pH 9, 50 mM $NaClO_4$, 20% MeCN. Buffer B was 1 mM EDTA, 25 mM Tris pH 9, 0.4 M $NaClO_4$, 20% MeCN. Separation was performed on a 0-65% B segmented gradient with buffers and column heated to 65° C.

Materials were purified on an ÅKTA Pilot equipped with a FineLine-70 column packed with TSKgel Q 5PW (Tosoh Biosciences) to a bed height of 28 cm (=1.08 L) Buffer A was 1 mM EDTA, 25 mM Tris pH 9. Buffer B was 1 mM EDTA, 25 mM Tris pH 9, 0.4 M $NaClO_4$. Buffers were heated by a 4 kW buffer heater set at 65° C., giving a column outlet temperature of 45° C. The solution containing the crude material was diluted 4-6 fold and loaded onto the column at 200 mL/min and eluted with a segmented gradient from 0-60% B. Appropriate fractions were pooled and this pooled material desalted in 30 mL amounts over Sephadex G-25 on a BioPilot column (6 cm dia.×7.5 cm) against $H_2O$. The eluate was vacuum evaporated to less than 25 mL, shell frozen and lyophilized.

The results of the synthesis of 25 and 26 with PADS or EDITH are shown in FIG. 6. It should be noted that the contact time used for EDITH is less than that suggested by Q. Xu et al. (one vs. two minutes.)

Example 5

Deprotection Conditions

General

The following oligonucleotide sequences used for various deprotection methods.

```
27: 5'CUUACGCUGAGUACUUCGAdTdT
    P = O RNA (SEQ ID NO: 8)

28: 5'UCGAAGUACUCAGCGUAAGdTdT.
    P = O/P = S RNA (SEQ ID NO: 9)

29: 5'GCGGAUCAAACCUCACCAAdTdT.
    P = O backbone (SEQ ID NO: 10)

30: 5'GCGGAUCAAACCUCACCAAdTdT.
    P = O/P = S mixed backbone (SEQ ID NO: 11)

31: 5'GCGGAUCAAACCUCACCAAdTdT.
    P = S backbone (SEQ ID NO: 12)

32: 5'UUGGUGAGGUUUGAUCCGCdTdT.
    P = O backbone (SEQ ID NO: 13)

33: 5'UUGGUGAGGUUUGAUCCGCdTdT.
    P = O/P = S mixed backbone (SEQ ID NO: 14)

34: 5'UUGGUGAGGUUUGAUCCGCdTdT.
    P = S backbone (SEQ ID NO: 15)
```

Method 1

A volumetric mixture (~1:4) of Py.HF and DBU with DMSO (4~5 volume of PyHF) as solvent at 65° C. for 15 mins. This is a two step reaction condition.

Control: A ~1 umole sample of 27 was deprotected by $MeNH_2$ at 65° C. for 20 mins and dried. Then it was treated with a mixture of 0.1 mL TEA.3HF, 0.075 mL TEA and 0.15 mL DMSO at 65° C. for 1.5 hours. The yield on HPLC was 47/54% (260 nm and 280 nm) on anion exchange HPLC. A 0.5 μmole OD sample of dried 27, deprotected by $MeNH_2$ at 65° C. for 20 mins, was dissolved in premixed 10 μL Py.HF, 50 μL DBU and 50 μL DMSO and heated at 65° C. The yield was 55/53% after 10 mins, 57/57% after 20 mins, 57/58% after 30 mins and 57/57% after 1 hour. The pH of this 1:5 mixture was found out to be about 10 by adding in water. Therefore, ~0.5 μmole of the $MeNH_2$ deprotected and dried 27 was deprotected by premixed 6.5 μL Py.HF, 27.4 μL DBU and 26 μL DMSO at 65° C. for 15 mins and 70 mins. The yield was 57/57% after 15 mins and 70 mins. A ~4 μmole sample of 27 was deprotected by concentrated ammonia at 65° C. for 1 hour and dried. The residue was then dissolved in premixed 0.06 mL Py.HF, 0.24 mL DBU, and 0.3 mL DMSO at 65° C. for 15 mins. The yield was 58/60%. A ~4 μmole sample of 27 was deprotected by ethanolic ammonia at 65° C. for 1 hour and dried. Premixed 0.06 mL Py.HF, 0.24 mL DBU, and 0.3 mL DMSO were used to treat the RNA at 65° C. for 15 min. The yield was 59/60%.

Compound 29 was synthesized at 1 μmole scale. It was deprotected by ethanolic ammonia at 65° C. for 1 hour, then divided to half (71 OD and 77 OD) and dried. 27 μL Py.HF, 108 μL DBU and 135 μL DMSO were mixed. Half of this mixture was used to treat the 77 OD sample for 20 mins at 65° C., the other half was used to treat the 71 OD sample for 30 mins. The yield was 64/63% after 20 mins and 62/63% after 30 mins. The fully thioated 31 was deprotected by ethanolic ammonia at 65° C. for 45 mins. The crude mixture was divided into half and dried, 76 OD in each sample. 20 μL Py.HF, 80 μL DBU and 100 μL DMSO were premixed, half of it were used to dissolve one sample and the other half for the other sample. At 65° C., the yield was 64/81% after 20 mins and 63/81% after 30 mins. No PS/PO conversion was detected on LC-MS.

Part of 28 was deprotected with MeNH$_2$ at 65° C. for 20 mins. The crude mixture was divided into ~40 OD samples and dried. The other part was deprotected with ethanolic ammonia at 65° C. for 40 mins, and also divided into ~40 OD samples and dried. One portion of MeNH$_2$ deprotected sample was desilylated with standard procedures (16 µL TEA.3HF, 12 µL TEA and 24 µL DMSO at 65° C.), the yield was 37/36% after 30 mins, 41/49% after 1 hour, 38/43% after 1.5 hours and 42/42% after 2.5 hours. Second portion of MeNH$_2$ deprotected sample was desilylated with premixed 9 µL Py.HF, 36 µL DBU and 36 µL DMSO at 65° C., and the yield was 44/45% after 15 mins, 46/45% after 30 mins, 45/44% after 1 hour, 45/44% after 1.5 hr and 44/48% after 2.5 hrs. Another portion of MeNH$_2$ deprotected sample was desilylated with premixed 9 µL Py.HF, 31.5 µL DBU and 31.5 µL DMSO at 65° C., and the yield was 42/45% after 15 mins, 45/47% after 30 mins, 45/44% after 1 hour, 45/48% after 1.5 hr and 39/47% after 2.5 hrs. One portion of ethanolic ammonia deprotected sample was desilylated with standard procedures (16 µL TEA.3HF, 12 µL TEA and 24 µL DMSO at 65° C.), the yield was 40/39% after 30 mins, 49/51% after 1 hour, 49/51% after 1.5 hour and 47/49% after 2.5 hour. Second portion of ethanolic ammonia deprotected sample was desilylated with premixed 9 µL Py.HF, 36 µL DBU and 36 µL DMSO at 65° C., and the yield was 50/50% after 15 mins, 49/49% after 30 mins, 53/54% after 1 hour, 55/58% after 1.5 hour and 54/54% after 2.5 hrs. Another portion of ethanolic ammonia deprotected sample was desilylated with premixed 9 µL Py.HF, 31.5 µL DBU and 31.5 µL DMSO at 65° C., and the yield was 52/52% after 15 mins, 52/51% after 30 mins, 52/52% after 1 hour, 53/55% after 1.5 hour and 52/55% after 2.5 hour.

Standard deprotection of 29 gave 47/48% yield. Ethanolic ammonia deprotection of 29 at 65° C. for 1 hour followed by 15 mins treatment with premixed 105 µL Py.HF, 367.5 µL DBU and 300 µL DMSO at 65° C. gave 47/49% yield. Part of the support was treated with ethanolic ammonia for 1.5 hr at 65° C. and then dissolved in premixed 105 µL Py.HF, 367.5 µL DBU and 300 µL DMSO at 65° C. for 15 mins, which gave 47/47% yield.

Deprotection for 1 hr in ethanolic ammonia at 65° C. followed by 65° C. and 20 mins/15 mins 1:3.5 mixture desilylation was applied on 32/34 gave 60/61% and 61/61% yields respectively. For 33 synthesized on 1 µmole scale, both standard and Pyridine-HF/DBU deprotections were done, and yields were 41/40% for standard and 45/43% for Pyridine-HF/DBU method.

Method 2: One Step Process
Silyl deprotection reagent: 4 volume desilylation mixture (1 mL Py.RHF, 3.5 mL DBU, 4 mL DMSO) per 1 volume of ethanolic ammonia at 60° C. for 20 mins.

This method was tested with a ~40 OD sample of 28 after MeNH$_2$ deprotection. 20 µL of ethanolic ammonia was used to dissolve the oligo, and then 80 µL of premixed Py.HF reagent (1 mL Py.HF+3.5 m DBU+4 mL DMSO) were added in to the sample. The yield was 49/45% when heated at 60° C. for 20 mins, 1 hour and 2 hours. Under this condition the deprotection was complete in 20 minute without any degradation of the RNA.

Method 3: A Two Step Process.
Silyl deprotection reagent: 5 µL DMSO and 2.5 µL DBU per 1 mg of poly{4-vinylpyridinium poly(hydrogen fluoride)] (PVPHF) at 65° C. for 20 min.

About 40OD of dried sample of ethanolic ammonia deprotected 27 was dissolved in 50 µL DMSO. 25 µL DBU and 10 mg PVPHF were added in and heated at 65° C. The yield was 52/51% after 20 mins, 54/57% after 40 mins and 55/62% after 90 mins. When the sample was treated with 50 µL DMSO, 30 µL DBU and 10 mg PVPHF at 65° C., the yield was 48/51% after 20 mins, 50/50% after 40 mins and 48/48% after 1.5 hours.

Method 4: One Step Deprotection
One-step deprotection with PVPHF: for every 10 µL ethanotic ammonia, add ~30-40 µL DMSO and 3 mg PVPHF. The deprotection takes up to 1.5 hours.

About 40O D dried sample of ethanolic ammonia deprotected 28 was redissolved in 30 ethanolic ammonia, and 90 µL DMSO and 9 mg PVPHF were added into it. The deprotection was not complete after 20 mins. Yield was 49/51% after 40 mins and 51/51% after 1.5 hours. A second portion of 28 was redissolved in 25 µL ethanolic ammonia and 100 µL DMSO with 9 mg PVPHF. The reaction was not complete after 20 min. The yield was 41/50% after 40 min and 50/57% after 1.5 hour. When a portion of 28 deprotected by MeNH$_2$ was redissolved in 20 µL ethanolic ammonia and 80 µL DMSO with 10 mg PVPHF gave 42/42% yield after 50 mins.

Method 5
One-step deprotection with PVPHF: for every 10 µL ethanolic ammonia, add ~30-40 µL DMSO, 5 µL DBU and ~4.5 mg PVPHF. The deprotection takes up to 40 min.

A ~40OD dried sample of MeNH$_2$ deprotected 28 was redissolved in 20 µL ethanolic ammonia, and then 80 µL DMSO, 10 µL DBU and 9 mg PVPHF were added into solution. This method gave 45/45% after 40 min and 46/49% yield after 1.5 hour.

Method 6: Tris(Dimethylamino)Sulfur Difluorotrimethylsilane (TAS-F) as Silyl Deprotecting Agent for RNA Synthesis About 1 µmole methylamine deprotected and dried 27 was treated with a solution of 0.16 g TAS-F in 0.2 mL of DMF at 55° C. for 2 hours. The reaction was not complete and the reaction mixture was not homogenous with some gel sitting out of the solution. 20 µL water was added into the reaction mixture. The reaction mixture became clear after overnight storing at 55° C. HPLC purification gave 51/55% for this reaction. The reproducibility of this reaction was not very consistent. ~0.6 µmole of 27 was treated with 80 mg TAS-F and 0.2 mL pyridine at 65° C. Only 22/21% yield was observed after 2 hours. ~0.6 µmole was treated with 80 mg TAS-F and 0.2 mL N-methylpyrrolidinone at 65° C. A precipitate was formed during the course of the reaction and the yield was 34/37% after 2 hrs. ~0.4 µmole of 27 was treated with 27 mg TAS-F, 0.15 mL N-methylpyrrolidinone and 0.5 mL DMSO at 65° C. for 2 hours. The yield was 35/24%. ~0.4 µmole was treated with 27 mg TAS-F, 0.15 mL1 N-methylpyrrolidinone and 0.05 mL DMSO at 65° C. for 2 hours. The yield was 25/25%. ~0.4 µmole of 27 was treated with 27 mg TAS-F, 0.15 mL N-methylpyrrolidinone and 0.05 mL pyridine at 65° C. for 2 hours. The yield was 22/22%. ~1 µmole of ethanolic ammonia deprotected and dried 27 was treated with 75 mg TAS-F and 0.2 mL DMSO at 65° C. The yield was 39/41% after 2 hours. ~1 µmole of this sample was treated with 75 mg TAS-F and 0.2 mL DMF at 65° C. Precipitate formed during the course of the reaction and the yield was 21/21% after 2 hours. ~1 µmole of ammonia deprotected and dried 27 was treated with 75 mg TAS-F and 0.2 mL DMSO at 65° C. The yield was 31/30% after 2 hours. ~1 µmole of this sample was treated with 75 mg TAS-F and 0.2 mL DMF at 65° C. Precipitate formed and the yield was 21/24% after 2 hours.

A ~40 OD sample of MeNH$_2$ deprotected (65° C. 20 mins) and dried 28 sample was treated with 41 mg TASF and 90 µL DMF at 65° C. Injections were done after 30 mins, 1 hr, 2 hr, and then at RT overnight. The reaction did not yield noticeable amount of product. Another ~40OD sample was treated with 41 mg TASF, 90 µL DMF and 40 µL water at 65° C. Injections were done after 30 min, 1 hr, 2 hr, and then at RT overnight. No major peak was detected in the HPLC for the product. Same deprotection conditions were applied on ~40OD samples of 28 deprotected by ethanolic ammonia (65° C., 40 min.) and same results were observed: no major peak.

Example 6

Microwave-mediated Deprotection of a 2'-Silyl Group of RNA

A. Deprotection 1 (Standard)

The oligonucleotide was cleaved from the support with simultaneous deprotection of base and phosphate groups with 2.0 mL of a mixture of ammonia and 8 M ethanolic methylamine [1:1] for 30 min at 65° C. The vial was cooled briefly on ice and then the ethanolic ammonia mixture was transferred to a new microfuge tube. The CPG was washed with 2×0.1 mL portions of deionized water, put in dry ice for 10 min, and then dried in speed vac.

B. Microwave Deprotection of 2'-O-TBDMS Group of RNA

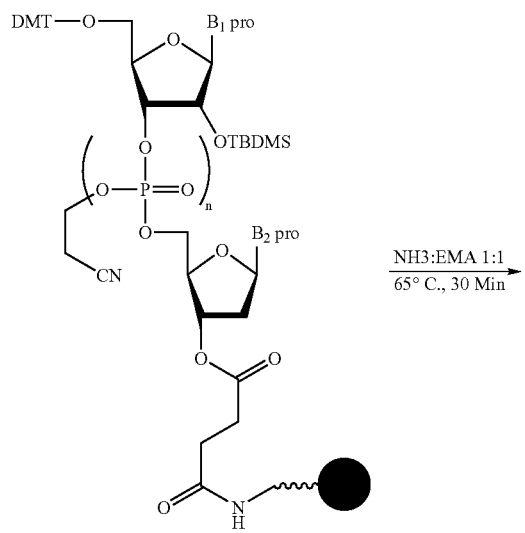

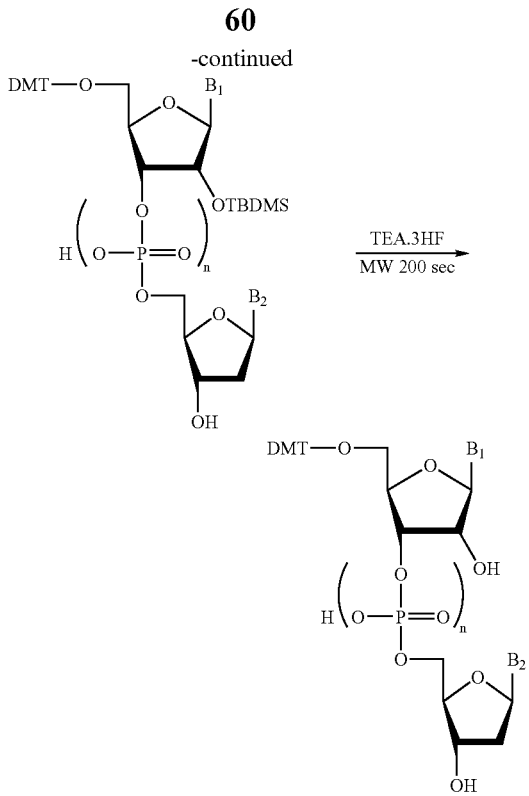

Instrument: CEM Discover Explorer, Magnetron Frequency 2450 MHz, Power output 300 Watts, Microwave Applicator: Circular Single mode, Self Tuning Reagents: A) 1 M TBAF in THF, B) TEA.3HF, C) Pyr.HF with DBU.

About 12 OD of Oligo 50 or 51 was resuspended in 600 µL of Reagent A to C. The vial containing the oligonucleotides was then placed in microwave unit. The solution was irradiated for 2 min. and 4 min. in CEM Discover Explorer.

Work Up

Condition A: In case of TBAF after Microwave irradiation quenched the reaction with water followed by desalting.

Condition B: The reaction was then quenched with 400 µL of isopropoxytrimethylsilane (iPrOSiMe$_3$, Aldrich) and further incubated on the heating block leaving the caps open for 10 min. (This causes the volatile isopropxytrimethylsilylfluoride adduct to vaporize). The residual quenching reagent was removed by drying in a speed vac. Added 1.5 mL of 3% triethylamine in diethyl ether and pelleted by centrifuging. The supernatant was pipetted out without disturbing the pellet. Dry the pellet in speed vac. The crude RNA was obtained as a white fluffy material in the microfuge tube.

Microwave Deprotection RNA and its MS Analysis

| Compound | Sequence | 2'-silyl deprotection condition | cal. mass | found mass |
|---|---|---|---|---|
| 50 | 5'ACGUCGAUAT 3' (SEQ ID NO: 16) | TBAF 2 min | 3142.95 | 3142.57 |

| Compound | Sequence | 2'-silyl deprotection condition | cal. mass | found mass |
|---|---|---|---|---|
| 50 | 5'ACGUCGAUAT 3' (SEQ ID NO: 16) | Py•HF 2 min | 3142.95 | nd |
| 50 | 5'ACGUCGAUAT 3' (SEQ ID NO: 16) | Py•HF 4 min | 3142.95 | nd |
| 51 | 5'CGUCAAGGCGAT 3' (SEQ ID NO: 17) | TBAF 2 min | 3832.37 | 3831.34 |
| 51 | 5'CGUCAAGGCGAT 3' (SEQ ID NO: 17) | TEA•3HF 2 min | 3832.37 | 3831.34 |
| 51 | 5'CGUCAAGGCGAT 3' (SEQ ID NO: 17) | TEA•3HF 4 min | 3832.37 | 3831.34 | nd: not determined

Example 7

The Applicants have surprisingly discovered that impurities in a composition of single stranded RNA can be readily removed by HPLC purification of a mixture of single-stranded RNA that has been annealed to generate double-stranded RNA.

General Procedure

Figure 9:
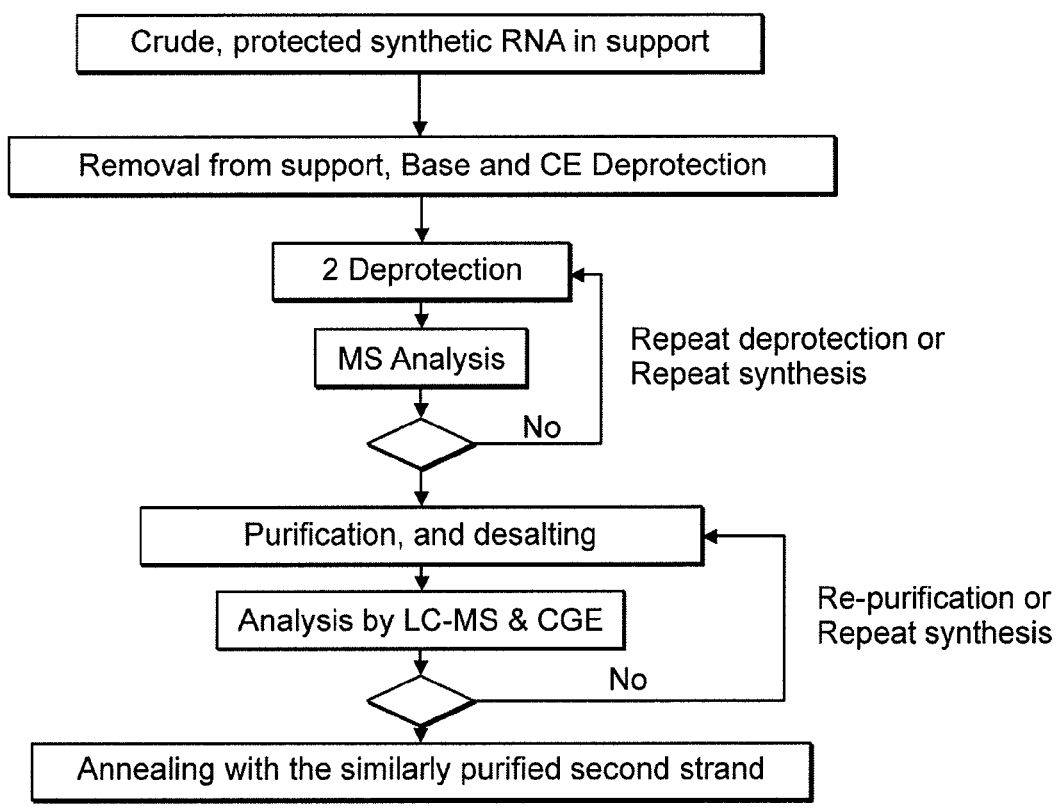
FIG. 9 depicts a flow chart for siRNA purification and QC. Note: LC-MS indicates liquid-chromatography mass spectrophotometric analysis; and CGE indicates capillary gel electrophoresis analysis.

A diagram illustrating the overall purification procedure is presented in FIG. 9. The specific procedure used for the purification of AL-DP-4014 is presented in FIGS. 11 and 12.

The analytical conditions used for reverse phase HPLC purification, ion exchange purification, capillary gel electrophoresis, and LC-MS are presented below.

Reverse Phase HPLC:
  Luna C-18 column, 150×2.0 mm, temp=25° C., flow-0.2 mL/min
  Buffer A: 35 mm TEAA PH=7, 100 mm HFIP
  Buffer B: MeOH
  Gradient: 25% B to 35% B in 50 minutes, ramp to 85% B at 55 minutes, re-equilibrate Ion Exchange Chromatography:
  Dnapac PA-100 ion exchange column, 250×4 mm, temp=65° C., flow=1 ml/min
  Buffer A: 50 mm NaClO$_4$, 25 mm tris pH=9.0, 1 mM EDTA, 20% CAN
  Buffer B: 400 mm NaClO$_4$, 25 mm tris pH=9.0, 1 mM EDTA, 20% CAN
  Gradient: hold at 0% B for 2.00 min, ramp to 40% B at 17 min, ramp to 65% B at 32 min, ramp to 100% B at 32.5 min. re-equilibrate Capillary Gel Electrophoresis:
  DNA 100R Gel, temp=40° C.
  Separate at 12 KV, reverse polarity LC-MS Analysis:
  Chromolith speedrod 50×4 mm temp=25° C., flow=0.8 mL/min
  Buffer A: 20% MeOH, 10 mm TBAA pH=7.0
  Buffer B: 80% MeOH, 10 mm TBAA pH=7.0
  Gradient: 40% B to 80% B in 19.5 min., ramp to 100% B at 23 minutes re-equilibrate Scan MS in negative ion mode from 500 to 3000

Results

The specific procedure used for the purification of AL-DP-4014 is presented in FIGS. 11 and 12. The chromatographic data presented in FIGS. 14-18 indicate that the purification procedure produced AL-DP-4014 in substantially pure form.

The purification procedure was performed as described above for AL-DP-4127, AL-DP-4139, AND AL-DP-414. The results from analytical analyses are presented in FIGS. 19-39.

Example 8

Procedure for Quenching Acrylonitrile

The solid support bound oligonucleotide is treated with excess of a mixture of triethylamine (or an amine with pKa=9-12), an organic solvent (e.g. acetonitrile, THF) and a thiol or a odorless thiol. The alkylamine would generate the acrylonitlile which would be scavenged by the thiol. This is an improvement over the process described by Capaldi et al. *Org. Process Res. Dev.* 2003, 7, 832-838.

Example 9

2'-O-Methyl-modified, 2'-Fluoro-modified, Conjugated, Thioate Oligonucleotides

Step 1. Oligonucleotide Synthesis

All oligonucleotides were synthesized on an AKTAoligopilot synthesizer. Commercially available controlled pore glass solid supports (dT-CPG, rC-CPG, rU-CPG, from Prime Synthesis) or the in-house synthesized solid supports (phthalimido-hydroxy-prolinol-CPG, hydroxyprolinol-cholesterol-CPG described in patent applications: provisional 60/600,703 Filed Aug. 10, 2004 and PCT/US04/11829 Filed Apr. 16, 2004) were used for the synthesis. RNA phosphoramidites and 2'-O-methyl modified RNA phosphoramidites with standard protecting groups (5'-O-dimethoxytrityl-N6-benzoyl-2'-t-butyldimethylsilyl-adenosine-3'-O—N,N'-diisopropyl-2-cyanoethylphosphoramidite, 5'-O-dimethoxytrityl-N4-acetyl-2'-t-butyldimethylsilyl-cytidine-3'-O—N,N'-diisopropyl-2-cyanoethylphosphoramidite, 5'-O-dimethoxytrityl-N2-isobutyl-2'-t-butyldimethylsilyl-guanosine-3'-O—N,N'-diisopropyl-2-cyanoethylphosphoramidite, 5'-O-dimethoxytrityl-2'-t-butyldimethylsilyl-uridine-3'-O—N,N'-diisopropyl-2-cyanoethylphosphoramidite, 5'-O-dimethoxytrityl-N6-benzoyl-2'-O-methyl-adenosine-3'-O—N,N'-diisopropyl-2-cyanoethylphosphoramidite, 5'-O-dimethoxytrityl-N4-acetyl-2'-O-methyl-cytidine-3'-O—N,N'-diisopropyl-2-cyanoethylphosphoramidite, 5'-O-dimethoxytrityl-N2-isobutryl-2'-O-methyl-guanosine-3'-O—N,N'-diisopropyl-2-cyanoethylphosphoramidite, and 5'-O-dimethoxytrityl-2'-

O-methyl-uridine-3'-O—N,N'-diisopropyl-2-cyanoethylphosphoramidite) were obtained from Pierce Nucleic Acids Technologies and ChemGenes Research. The 2'-F phosphoramidites (5'-O-dimethoxytrityl-N4-acetyl-2'-fluoro-cytidine-3'-O—N,N'-diisopropyl-2-cyanoethyl-phosphoramidite and 5'-O-dimethoxytrityl-2'-fluoro-uridine-3'-O—N,N'-diisopropyl-2-cyanoethyl-phosphoramidite) were obtained from Promega. All phosphoramidites were used at a concentration of 0.2 M in $CH_3CN$ except for guanosine and 2'-O-methyl-uridine, which were used at 0.2 M concentration in 10% $THF/CH_3CN$ (v/v). Coupling/recycling time of 16 minutes was used for all phosphoramidite couplings. The activator was 5-ethyl-thio-tetrazole (0.75 M, American International Chemicals). For the PO-oxidation, 50 mM iodine in water/pyridine (10:90 v/v) was used and for the PS-oxidation 2% PADS (GL Synthesis) in 2,6-lutidine/$CH_3CN$ (1:1 v/v) was used. The cholesterol and amino-linker phosphoramidites were synthesized in house, and used at a concentration of 0.1 M in dichloromethane for cholesterol and 0.2 M in $CH_3CN$ for the amino-linker. Coupling/recycling time for both the cholesterol and the amino-linker phosphoramidites was 16 minutes.

Step 2. Deprotection of Oligonucleotides (a) Deprotection of RNAs without the 2'-fluoro modification: After completion of synthesis, the support was transferred to a 100 mL glass bottle (VWR). The oligonucleotide was cleaved from the support with simultaneous deprotection of base and phosphate groups with 40 mL of a 40% aq. methyl amine (Aldrich) 90 mins at 45° C. The bottle was cooled briefly on ice and then the methylamine was filtered into a new 500 mL bottle. The CPG was washed three times with 40 mL portions of DMSO. The mixture was then cooled on dry ice.

In order to remove the tert-butyldimethylsilyl (TBDMS) groups at the 2' position, 60 mL triethylamine trihydrofluoride ($Et_3N$—HF) was added to the above mixture. The mixture was heated at 40° C. for 60 minutes. The reaction was then quenched with 220 mL of 50 mM sodium acetate (pH 5.5) and stored in the freezer until purification.

(b) Deprotection of 2'-fluoro modified RNAs: After completion of synthesis, the support was transferred to a 100 mL glass bottle (VWR). The oligonucleotide was cleaved from the support with simultaneous deprotection of base and phosphate groups with 80 mL of a mixture of ethanolic ammonia (ammonia:ethanol, 3:1 v/v) for 6.5 h at 55° C. The bottle was cooled briefly on ice and then the ethanolic ammonia mixture was filtered into a new 250 mL bottle. The CPG was washed with twice with 40 mL portions of ethanol/water (1:1 v/v). The volume of the mixture was then reduced to ~30 mL by roto-vap. The mixture was then frozen on dry ice and dried under vacuum on a speed vac.

The dried residue was resuspended in 26 mL of triethylamine, triethylamine trihydrofluoride (Et3N.3HF), and DMSO (3:4:6) and heated at 60° C. for 90 minutes to remove the tert-butyldimethylsilyl (TBDMS) groups at the 2' position. The reaction was then quenched with 50 mL of 20 mM sodium acetate and the pH was adjusted to 6.5, and the solution was stored in freezer until purification.

Step 3. Quantitation of Crude Oligonucleotides

For all samples, a 10 µL aliquot was diluted with 990 µL of deionised nuclease free water (1.0 mL) and the absorbance reading at 260 nm was obtained.

Step 4. Purification of Oligonucleotides (a) Unconjugated oligonucleotides: The unconjugated crude oligonucleotides were first analyzed by HPLC (Dionex PA 100). The buffers were 20 mM phosphate, pH 11 (buffer A); and 20 mM phosphate, 1.8 M NaBr, pH 11 (buffer B). The flow rate 1.0 m L/min and monitored wavelength was 260-280 nm. Injections of 5-15 µL were done for each sample.

The unconjugated samples were purified by HPLC on an TSK-Gel SuperQ-5PW (20) column packed in house (17.3×5 cm). The buffers were 20 mM phosphate in 10% $CH_3CN$, pH 8.5 (buffer A) and 20 mM phosphate, 1.0 M NaBr in 10% $CH_3CN$, pH 8.5 (buffer B). The flow rate was 50.0 mL/min and wavelengths of 260 and 294 nm were monitored. The fractions containing the full-length oligonucleotides were pooled together, evaporated, and reconstituted to about 100 mL with deionised water.

(b) Cholesterol-conjugated oligonucleotides: The cholesterol-conjugated crude oligonucleotides were first analyzed by LC/MS to determine purity. The 5'-cholesterol conjugated sequences were HPLC purified on an RPC-Source 15 reverse-phase column packed in house. The buffers were 20 mM TEAA in 10% $CH_3CN$ (buffer A) and 20 mM TEAA in 70% $CH_3CN$ (buffer B). The fractions containing the full-length oligonucleotides were then pooled together, evaporated, and reconstituted to 100 mL with deionised water. The 3'-cholesterol conjugated sequences were HPLC purified on an RPC-Source 15 reverse-phase column packed in house. The buffers were 20 mM NaOAc in 10% $CH_3CN$ (buffer A) and 20 mM NaOAc in 70% $CH_3CN$ (buffer B). The fractions containing the full-length oligonucleotides were pooled, evaporated, and reconstituted to 100 mL with deionised water.

Step 5. Desalting of Purified Oligonucleotides

The purified oligonucleotides were desalted on an AKTA Explorer system (Amersham Biosciences) using a Sephadex G-25 column. First, the column was washed with water at a flow rate of 25 mL/min for 20-30 min. The sample was then applied in 25 µL fractions. The eluted salt-free fractions were combined, dried, and reconstituted in 50 mL of RNase free water.

Step 6. Purity Analysis by Capillary Gel Electrophoresis (CGE), Ion-exchange HPLC, and Electrospray LC/Ms Approximately 0.3 OD of each of the desalted oligonucleotides were diluted in water to 300 µL and were analyzed by CGE, ion exchange HPLC, and LC/MS.

| AL-SQ # | Sequence | Target | Calc Mass | Found Mass | Purity (%) |
|---|---|---|---|---|---|
| 2936 | HP-NH2-CUUACGCUGAGUAC UUCGAdTsdT (SEQ ID NO: 18) | Luc | 6915 | 6915.01 | 97.8* |
| 2937 | CsUUACGCUGAGUACUUGGAd TdTdT-HP-NH2 (SEQ ID NO: 19) | Luc | 6915 | 6915.06 | 95.9* |
| 5225 | GUCAUCACACUGAAUACCAAU s-Chol (SEQ ID NO: 20) | ApoB | 7344 | 7344.70 | 83 |

-continued

| AL-SQ # | Sequence | Target | Calc Mass | Found Mass | Purity (%) |
|---|---|---|---|---|---|
| 3169 | U$_F$sU$_F$GGAUC$_F$AAAU$_F$AU$_F$AA GAU$_F$UCG$_F$sG$_F$sU (SEQ ID NO: 21) | ApoB | 7325.39 | 7325.5 | 92 |
| 2920 | GGAC$_F$U$_F$AC$_F$U$_F$C$_F$U$_F$AAGU$_F$ U$_F$C$_F$U$_F$AC$_F$dTsdT (SEQ ID NO: 22) | Factor VII | 6628.93 | 6628.45 | 99.6 |
| 2921 | GU$_F$AGAAC$_F$U$_F$U$_F$AGAGU$_F$AG U$_F$C$_F$C$_F$dTsdT (SEQ ID NO: 23) | Factor VII | 6726.04 | 6725.78 | 96.0 |
| 4723 | GGAU$_F$C$_F$AU$_F$C$_F$U$_F$C$_F$AAGU$_F$ C$_F$U$_F$U$_F$AC$_F$dTsdT (SEQ ID NO: 24) | Factor VII | 6628.93 | 6628.47 | 98.9 |
| 4724 | GU$_F$AAGAC$_F$U$_F$U$_F$GAGAU$_F$GA U$_F$C$_F$CCdTsdT (SEQ ID NO: 25) | Factor VII | 6726.04 | 6725.56 | 96.3 |
| 3000 | CsGUCU$_F$GUCU$_F$GUCCCGGAU CdTsdT (SEQ ID NO: 26) | G6P | 6610.94 | 6611.34 | 92 |
| 3002 | GsAUCCGGGAC$_F$AGAC$_F$AGAC GdTsdT (SEQ ID NO: 27) | G6P | 6806.2 | 6806.06 | 93 |
| 2918 | Chol-GGAU$_F$C$_F$AU$_F$C$_F$U$_F$C$_F$ AAGU$_F$C$_F$U$_F$U$_F$AC$_F$dTsdT (SEQ ID NO: 28) | Factor VII | 7332.93 | 7333.61 | 99.9 |
| 2919 | Chol-GGAC$_F$U$_F$AC$_F$U$_F$C$_F$U$_F$ AAGU$_F$C$_F$U$_F$AC$_F$dTsdT (SEQ ID NO: 29) | Factor VII | 7332.93 | 7333.62 | 99.6 |
| 3168 | GsGAAUCU$_F$U$_F$AU$_F$AU$_F$U$_F$U$_F$ GAUCC$_F$AAs-Chol (SEQ ID NO: 30) | ApoB | 7393 | 7393.3 | 76.4 |
| 3001 | CsGUCU$_F$GUCU$_F$GUCCGGGAU CdTsdTs-Chol (SEQ ID NO: 31) | G6P | 7330.94 | 7331.3 | 79.4 |
| 4968 | CGUGCUU$_{OMe}$GAAGAAGAU$_{OMe}$ GGU$_{OMe}$GG$_{OMe}$sG$_{OMe}$sC (SEQ ID NO: 32) | GFP | 7504.7 | 7504.20 | 92 |
| 5226 | AUUGGUAUUCAGUGUGAUGA C$_{OMe}$sA$_{OMe}$sC (SEQ ID NO: 33) | ApoB | 7409.5 | 7409.80 | 91 |
| 5475 | U$_{OMe}$U$_{OMe}$GGAUC$_{OMe}$AAAU$_{OMe}$ AU$_{OMe}$AAGAU$_{OMe}$UCC$_{OMe}$sC$_{OMe}$sU (SEQ ID NO: 34) | ApoB | 7421.7 | 7421.4 | 89 |
| 3196 | CsU$_{OMe}$AUGAGCCUGAAGCC$_{OMe}$ U$_{OMe}$A$_{OMe}$AdTsdT (SEQ ID NO: 35) | a-synuclein | 6741.2 | 6741.01 | 92.6 |
| 3197 | U$_{OMe}$sU$_{OMe}$AGGCUUCAGGCU CAU$_{OMe}$AGdTsdT (SEQ ID NO: 36) | a-synuclein | 6721.12 | 6720.93 | 91.9 |
| 3199 | CsU$_{OMe}$ACGAACCUGAAGCC$_{OMe}$ U$_{OMe}$A$_{OMe}$AdTsdT (SEQ ID NO: 37) | a-synuclein | 6724.21 | 6723.94 | 92.2 |
| 3200 | U$_{OMe}$sU$_{OMe}$AGGCUUGAGGUU CGU$_{OMe}$AGdTsdT (SEQ ID NO: 38) | a-synuclein | 6738.11 | 6737.88 | 79.6 |
| 3201 | CsU$_{OMe}$ACGAACCUUGAAGCC$_{OMe}$ U$_{OMe}$A$_{OMe}$AdTsdTs-Chol (SEQ ID NO: 39) | a-synuclein | 7444.21 | 7445.08 | 91.4 |
| 3198 | CsU$_{OMe}$AUGAGCCUGAAGCC$_{OMe}$ U$_{OMe}$A$_{OMe}$AdTsdTs-Chol (SEQ ID NO: 40) | a-synuclein | 7461.2 | 7462.02 | 85.7 |
| 3131 | AsGAAGC$_{OMe}$AGGACCUU$_{OMe}$A UCGUoMCAdTsdTs-Chol (SEQ ID NO: 41) | ApoB | 7471.1 | 7472.17 | 97.6 |
| 5474 | GGAAUGU$_{OMe}$U$_{OMe}$AU$_{OMe}$AU$_{OMe}$ U$_{OMe}$U$_{OMe}$GAUCC$_{OMe}$AAs-Chol (SEQ ID NO: 42) | ApoB | 7461.1 | 7461.9 | 83 |
| 4967 | GC$_{OMe}$ACC$_{OMe}$AUCUUCUUC$_{OMe}$ AAGGACGs-Chol (SEQ ID NO: 43) | GFP | 7394 | 7394.80 | 91 |
| 3037 | A$_{OMe}$sC$_{OMe}$sA$_{OMe}$sA$_{OMe}$sA$_{OMe}$s C$_{OMe}$sA$_{OMe}$sC$_{OMe}$sC$_{OMe}$sA$_{OMe}$s U$_{OMe}$sU$_{OMe}$sG$_{OMe}$sU$_{OMe}$sG$_{OMe}$s A$_{OMe}$sC$_{OMe}$sA$_{OMe}$sG$_{OMe}$sU$_{OMe}$s C$_{OMe}$sC$_{OMe}$sA$_{OMe}$s-Chol (SEQ ID NO: 44) | miR-122A | 8613.43 | 8614.53 | 82.7 |

-continued

| AL-SQ # | Sequence | Target | Calc Mass | Found Mass | Purity (%) |
|---|---|---|---|---|---|
| 3038 | $A_{OMe}sC_{OMe}sA_{OMe}A_{OMe}A_{OMe}C_{OMe}$ $A_{OMe}A_{OMe}A_{OMe}C_{OMe}MMeC_{OMe}U_{OMe}$ $sC_{OMe}sC_{OMe}sA_{OMe}s$-Chol (SEQ ID NO: 45) | miR-122A | 8340.09 | 8341.23 | 99.2 |
| 3039 | $A_{OMe}sC_{OMe}sA_{OMe}sC_{OMe}sA_{OMe}s$ $C_{OMe}sA_{OMe}sA_{OMe}sC_{OMe}sA_{OMe}s$ $C_{OMe}sU_{OMe}sG_{OMe}sU_{OMe}sC_{OMe}s$ $A_{OMe}sC_{OMe}sA_{OMe}sU_{OMe}sU_{OMe}s$ $C_{OMe}sC_{OMe}sA_{OMe}s$-Chol (SEQ ID NO: 46) | miR-122A | 8613.43 | 8614.75 | 86.6 |
| 3040 | $A_{OMe}sC_{OMe}sA_{OMe}A_{OMe}C_{OMe}A_{OMe}$ $A_{OMe}C_{OMe}A_{OMe}C_{OMe}U_{OMe}G_{OMe}U_{OMe}$ $G_{OMe}A_{OMe}C_{OMe}A_{OMe}U_{OMe}U_{OMe}sC_{OMe}$ $sC_{OMe}sA_{OMe}s$-Chol (SEQ ID NO: 47) | miR-122A | 8340.09 | 8341.15 | 85.2 |

The strands are shown written 5' to 3'. Lower case "s" indicates a phosphorothioate linkage. The lower case "d" indicates a deoxy residue. "HP—NH2" or "NH2-HP" indicates a hydroxyprolinol amine conjugate. "Chol-" indicates a hydroxyprolinol cholesterol conjugate. Subscript "OMe" indicates a 2'-O-methyl sugar and subscript "F" indicates a 2'-fluoro modified sugar. Purity was determined by CGE except where indicated by an asterisk (in these two cases, purity was determined by ion-exchange chromatography).

Example 10

Deprotection Methods of RNA (with 2'-OMe, PS, or Cholesterol Modifications) Using Py.HF and Polyvinylpyridine polyHF (PVPHF)

Step 1. Oligonucleotide Synthesis

All oligonucleotides were synthesized on an AKTA oligo-pilot synthesizer. Commercially available controlled pore glass solid support (dT-CPG, U-CPG 500) or the hydroxy-prolinol-cholesterol solid support (described in patent applications: provisional 60/600,703 Filed Aug. 10, 2004 and PCT/US04/11829 Filed Apr. 16, 2004) was used. RNA phosphoramidites with standard protecting groups, 5'-O-dimethoxytrityl-N6-benzoyl-2'-t-butyldimethylsilyl-adenosine-3'-O—N,N'-diisopropyl-2-cyanoethylphosphoramidite, 5'-O-dimethoxytrityl-N4-acetyl-2'-t-butyldimethylsilyl-cytidine-3'-O—N,N'-diisopropyl-2-cyanoethylphosphoramidite, 5'-O-dimethoxytrityl-N2-isobutryl-2'-t-butyldimethylsilyl-guanosine-3'-O—N,N'-diisopropyl-2-cyanoethylphosphoramidite, 5'-O-dimethoxytrityl-2'-t-butyldimethylsilyl-uridine-3'-O—N,N'-diisopropyl-2-cyanoethylphosphoramidite and 5'-O-dimethoxytrityl-thymidine-3'-O—N,N'-diisopropyl-2-cyanoethylphosphoramidite were used for the oligonucleotide synthesis. All phosphoramidites were used at a concentration of 0.2 M in acetonitrile ($CH_3CN$) except for guanosine and 2'-OMe uridine which was used at 0.2 M concentration in 10% THF/acetonitrile (v/v). Coupling/recycling time was 14 minutes with linear flow of 500 cm/h on a 12 mL synthesis column. The activator was 5-ethyl thiotetrazole (0.75M). For the PO-oxidation 0.5 M iodine in pyridine with 10% water was used and for the PS-oxidation 0.2 M PADS in 1:1 mixture of $CH_3CN$ and 2,6-lutidine was used. Capping mixture A was 20% N-methyl imidazole and 80% $CH_3CN$ and capping mixture B was 25% acetic anhydride, 30% 2,6-lutidine and 45% $CH_3CN$.

The oligonucleotides synthesized, scale, support type, amount and loading are listed below:

| Alnylam SQ No. | Support, Mass (gram) | Mass of support (g) | Loading (µmol/g) | Scale (umol) | Synthesis column |
|---|---|---|---|---|---|
| 5718 | dT | 4.15 | 84 | 349 | 12 mL |
| 5719 | dT | 4.15 | 84 | 349 | 12 mL |
| 3216 | dT | 4.01 | 87 | 349 | 12 mL |
| 3218 | dT | 4.08 | 87 | 355 | 12 mL |
| 5474 | Hydroxy prolinol cholesterol | 4.1 | 68.6 | 281 | 12 mL |
| 5475 | rU | 3.9 | 83 | 324 | 12 mL |

Step 2. Deprotection

Four methods of deprotection were employed to achieve the following two steps of cleavage and deprotection: Step 1) cleavage of oligonucleotide from support with simultaneous removal of base and phosphate protecting groups from the oligonucleotide, Step 2) deprotection of 2'-O-TBDMS groups.

(a) Deprotection with Pyridine HF: The solid support from a 200 µmol synthesis was treated with 30 mL (1 vol) of $MeNH_2$ (40%, aqueous) at 45° C. for 1.5 hours. The support was filtered out and rinsed with 60 mL (2 vol) DMSO. Cool it for about 10 minutes in dry ice, a mixture of 7.5 mL pyridine HF (70%) and 30 mL (1 vol) DMSO was added to the filtrate and rinse solution and it was heated at 40° C. for 1 hour. The reaction was quenched with 50 mM sodium phosphate (pH 5.5) and diluted with water to an appropriate volume.

(b) Deprotection with Pyridine HF with DBU: The solid support from a 200 µmol synthesis was treated with 20 mL $MeNH_2$ (40%, aqueous) at 45° C. for 1.5 hours. The support was filtered out and rinsed with 60 mL DMSO. 10 mL DBU was added in the solution. Cool it for about 10 minutes in dry ice, a mixture of 6 mL pyridine HF (70%) and 20 mL DMSO were added to the filtrate and rinse solution and it was heated at 40° C. for 1 hour. The reaction was quenched with 50 mM sodium phosphate (pH 5.5) and diluted with water.

(c) Deprotection with Polyvinylpyridine polyHF (PVPHF): The solid support from a 200 µmol synthesis was treated with 30 mL $MeNH_2$ (40%, aqueous) at 45° C. for 1.5 hours. The support was filtered out and rinsed with 90 mL DMSO. Cool it for about 10 minutes in dry ice, PVPHF (12 g) was added to the filtrate and rinse solution and it was heated at 40° C. for 1 hour. The reaction was quenched with 50 mM sodium phosphate (pH 5.5). The reaction mixture was filtered and the solid was rinsed with water.

(d) Deprotection with Polyvinylpyridine polyHF (PVPHF) with DBU: The solid support from a 200 μmol synthesis was treated 20 mL MeNH$_2$ (40%, aqueous) at 45° C. for 1.5 hours. The support was filtered out and rinsed with 80 mL DMSO. 8 mL DBU was added in the solution. Cool it for about 10 minutes in dry ice, 12 g PVPHF were added into the filtrate and rinse solutions and the reaction was heated at 40° C. for 1 hour. The reaction was quenched with 50 mM sodium phosphate (pH 5.5). The reaction mixture was filtered and the solid was rinsed with water.

Step 3. Purification of Oligonucleotides (a) Ion Exchange HPLC Purification: The buffers used for the ion exchange purification were 20 mM sodium phosphate, 10% CH$_3$CN, pH 8.5 (solvent A) and 20 mM sodium phosphate, 1 M NaBr, 10% CH$_3$CN, pH 8.5 (solvent B). When the amount of crude oligonucleotide was less than 10,000 OD, a Waters 2 cm column with TSK Gel super Q-5PW resin was used. The flow rate was 10 mL/min and the gradient was 0 to 20% solvent B over 30 minutes, then 20 to 50% B over 200 minutes.

When the amount of crude oligonucleotide was more than 10,000 OD or higher resolution was needed due to contamination with short oligonucleotides, a Waters 5 cm column with TSK-GEL super Q-5PW resin was used. The flow rate was 50 mL/min and the gradient was 0 to 20% solvent B over 30 minutes and then 20 to 50% solvent B over 200 minutes.

(b) Reverse phase HPLC Purification: For reverse phase purification, the buffers were 20 mM sodium acetate, 10% CAN, pH 8.5 (solvent A) and 20 mM sodium acetate, 70% CH$_3$CN, pH 8.5 (solvent B). A 5 cm Waters column with source 15 RPC was used. The flow rate was 50 mL/min and the gradient was 0 to 15% solvent B over 30 minutes followed by 15 to 50% solvent B over 160 minutes.

Step 4. Desalting of Purified Oligomer

The purified oligonucleotides were desalted on a Waters 5 cm column with size exclusion resin Sephadex G-25. The flow rate was 25 mL/min. The eluted salt-free fractions were combined together, dried down and reconstituted in RNase-free water.

Step 5. Capillary Gel Electrophoresis (CGE) and Electrospray LC/Ms

Approximately 0.15 OD of oligonucleotide was diluted in water to 150 μL. Mass of the product and purity (as shown below) were determined by LC/MS analysis and anion exchange HPLC or CGE.

| AL-SQ # | TARGET | Sequence | Cal. Mass | Obs. Mass | Purity % | Deprotect. Method |
|---|---|---|---|---|---|---|
| 5718 | RSV | GGCUCUUAGCAAAGUCAA GdTdT (SEQ ID NO: 48) | 6693 | 6693 | 95 | Pyridine HF |
| 5718 | RSV | GGCUCUUAGCAAAGUCAA GdTdT (SEQ ID NO: 49) | 6693 | 6693 | 97 | Pyridine HF with DBU |
| 5719 | RSV | CUUGACUUUGCUAAGAGC CdTdT (SEQ ID NO: 50) | 6607 | 6606 | 95 | Pyridine HF |
| 5719 | RSV | CUUGACUUUGCUAAGAGC CdTdT (SEQ ID NO: 51) | 6607 | 6606 | 96 | Pyridine HF with DBU |
| 3216 | Apo B | GGAAUCU$_{OMe}$U$_{OMe}$AU$_{OMe}$AU$_{OMe}$U$_{OMe}$U$_{OMe}$GAUCC$_{OMe}$AdT (SEQ ID NO: 52) | 6716 | 6717 | 93 | PVPHF |
| 3216 | Apo B | GGAAUCU$_{OMe}$U$_{OMe}$AU$_{OMe}$AU$_{OMe}$U$_{OMe}$U$_{OMe}$GAUCC$_{OMe}$AdT (SEQ ID NO: 53) | 6716 | 6717 | 94 | PVPHF with DBU |
| 3218 | ApoB | GsGAAUCUUAUAUUUGAU CCAsdT (SEQ ID NO: 54) | 6650 | 6651 | | PVPHF |
| 3218 | Apo B | GsGAAUCUUAUAUUUGAU CCAsdT (SEQ ID NO: 55) | 6650 | 6651 | | PVPHF with DBU |
| 5474 | Apo B | GGAAUCU$_{OMe}$U$_{OMe}$AU$_{OMe}$AU$_{OMe}$U$_{OMe}$U$_{OMe}$GAUCC$_{OMe}$A$_{OMe}$As-Chol (SEQ ID NO: 56) | 7461 | 7462 | 90 | Pyridine HF with DBU |
| 5475 | Apo B | U$_{OMe}$U$_{OMe}$GGAUC$_{OMe}$AAAU$_{OMe}$AU$_{OMe}$AAGAU$_{OMe}$UCC$_{OMe}$sC$_{OMe}$sU (SEQ ID NO: 57) | 7421 | 7421 | 93 | Pyridine HF with DBU |

Oligonucleotides are shown written 5' to 3'. Lower case "s" indicates a phosphorothioate linkage. The lower case "d" indicates a deoxy residue. Subscript "OMe" indicates a 2'-O-methyl sugar. "Chol-" indicates a hydroxyprolinol cholesterol conjugate.

Example 11

Deprotection Methods of Chimeric RNA with 2'-Fluoro Modification Using Polyvinylpyridine polyHF (PVPHF)

Step 1. Oligonucleotide Synthesis

Synthesis, purification and desalting were same as described in Example 9, Step 1.

Step 2. Deprotection

After the synthesis was completed, ~30 mL of 0.5 M piperidine in CH$_3$CN were pumped through the column at a flow rate of between 5 and 10 mL/min to remove the cyanoethyl protecting groups from phosphate linkages while the RNA was still attached to the support. Then, two methods of deprotection were evaluated to achieve the following two steps of cleavage and deprotection: Step 1) cleavage of oligonucleotide from support with simultaneous removal of base protecting groups from the oligonucleotide and Step 2) deprotection of 2'-O-TBDMS groups (a) Deprotection with Polyvinylpyridine polyHF (PVPHF): The solid support from a 200 μmol synthesis was treated with 50 mL solution of NH$_3$:ethanol (3:1) at 55° C. for 6 hours. The support was separated from solution by filtering and was rinsed with 90 mL DMSO. The solid support was removed by filtering. The filtrate and rinse solution was cooled for about 10 minutes in dry ice, PVPHF (12 g) was added, and the solution was heated at 40° C. for 2 hours. Deprotection status was checked after 1 hour, 1.5 hours, and 2 hours. The reaction was quenched with 50 mM sodium phosphate (pH 5.5). The reaction mixture was filtered and the solid was rinsed with water.

(b) Deprotection with Polyvinylpyridine polyHF (PVPHF) with DBU: The solid support from a 200 μmol synthesis was treated 35 mL MeNH$_2$ (40%, aqueous) at 55° C. for 6 hours. The support was filtered out and rinsed with 140 mL DMSO. DBU (7 mL) was added to the filtrate and rinse solution. The solution was cooled for about 10 minutes in dry ice, 12 g PVPHF was added, and the reaction was heated at 40° C. for 2 hour. Deprotection status was checked after 1 hour, 1.5 hours, and 2 hours. The reaction was quenched with 50 mM sodium phosphate (pH 5.5). The reaction mixture was filtered and the solid was rinsed with water.

Example 12

Deprotection Method for RNA Oligonucleotides

Step 1. Oligonucleotide Synthesis

Synthesis, purification and desalting were same as described in Example X, Step 1. The synthesis of oligonucleotides AL-SQ-5548 (5'-AAA GUG CAC AAC AUU AUA C dTdT-3'SEQ ID NO: 58,where all residues were ribo except for the two 3' terminal nucleotides which were deoxy thymidine) and AL-SQ-5549 (5'-GUA UAA UGU UGU GCA CUU UdTdT-3'SEQ ID NO: 59) was done at 400 μmole scale. The calculated mass of AL-SQ-5548 was 6645.03; the observed mass was 6644.94. The calculated mass of AL-SQ-5549 was 6609.88; the observed mass was 6609.70.

Step 2. Deprotection Conditions

The deprotection was done at 94 μmole scale. Dried CPG (1.5 g) was placed in a 100 mL Schott bottle. Methyl amine (40% aqueous, 25 mL) was added to the bottle and the mixture was placed in a shaker oven at 45° C. for 1.5 h. The mixture was cooled and filtered into a 250 mL Schott bottle. The CPG was washed three times with 25 mL DMSO in a funnel. The combined filtrates were cooled for 10 min in dry ice. HF in pyridine (Aldrich, 20 mL) was added to the bottle. The mixture was shaken well and placed in a shaker oven at 40° C. for 1 h. The mixture was cooled to room temperature and the reaction was quenched by adding 150 mL of 50 mM sodium acetate. The final solution was stored at 4° C.

Step 3. Quantitation of Crude Oligonucleotides

In order estimate the crude yield the following procedure was used. Since the pyridine present in the crude oligonucleotide solution absorbs at 254 nm, the absorbance was measured at 280 nm. A small amount of the crude support was subjected to deprotection using TEA.3HF instead of HF in pyridine. Absorbance was measured for this sample at 254 nm and 280 nm. Based on the ratio of A$_{254}$ to A$_{280}$ of this sample, the absorbance at 254 nm for the sample containing pyridine was estimated.

The amount of full-length product was determined by anion exchange HPLC. For AL-SQ-5548, the full-length product was 73% of the total strand concentration and for AL-SQ-5549 full-length product was 67%. The crude yield was 1430D/μmole.

Example 13

Synthesis and Deprotection Conditions for RNAs at 1.6 mmol Scale

Step 1. Oligonucleotide Synthesis

The oligonucleotides were synthesized on an AKTA oligopilot synthesizer. Commercially available controlled pore glass solid supports (from Prime Synthesis) were used. RNA phosphoramidites and 2'-O-methyl modified RNA phosphoramidites with standard protecting groups (5'-O-dimethoxytrityl-N6-benzoyl-2'-t-butyldimethylsilyl-adenosine-3'-O—N,N'-diisopropyl-2-cyanoethylphosphoramidite, 5'-O-dimethoxytrityl-N4-acetyl-2'-t-butyldimethylsilyl-cytidine-3'-O—N,N'-diisopropyl-2-cyanoethylphosphoramidite, 5'-O-dimethoxytrityl-N2-isobutryl-2'-t-butyldimethylsilyl-guanosine-3'-O—N,N'-diisopropyl-2-cyanoethylphosphoramidite, 5'-O-dimethoxytrityl-2'-t-butyldimethylsilyl-uridine-3'-O—N,N'-diisopropyl-2-cyanoethylphosphoramidite, 5'-O-dimethoxytrityl-N6-benzoyl-2'-O-methyl-adenosine-3'-O—N,N'-diisopropyl-2-cyanoethylphosphoramidite, 5'-O-dimethoxytrityl-N4-acetyl-2'-O-methyl-cytidine-3'-O—N,N'-diisopropyl-2-cyanoethylphosphoramidite, 5'-O-dimethoxytrityl-N2-isobutryl-2'-O-methyl-guanosine-3'-O—N,N'-diisopropyl-2-cyanoethylphosphoramidite, and 5'-O-dimethoxytrityl-2'-O-methyl-uridine-3'-O—N,N'-diisopropyl-2-cyanoethylphosphoramidite) were obtained from Pierce Nucleic Acids Technologies and ChemGenes Research. The 2'-F phosphoramidites (5'-O-dimethoxytrityl-N4-acetyl-2'-fluoro-cytidine-3'-O—N,N'-diisopropyl-2-cyanoethyl-phosphoramidite and 5'-O-dimethoxytrityl-2'-fluoro-uridine-3'-O—N,N'-diisopropyl-2-cyanoethyl-phosphoramidite) were obtained from Promega.

All phosphoramidites were used at a concentration of 0.15 M in CH$_3$CN. The RNA amidite coupling/recycling time was 23 minutes and 2 equivalents of amidite were used. DNA coupling cycle used 60% activator, 7 min recycling, and 2.0 equivalents of phosphoramidite. A UV watch was introduced in the "push" step before the "recycle" step to assure consistency in each coupling step. The activator was 0.6 M ethylthiotetrazole. For the PO-oxidation, 50 mM iodine in water/pyridine (10:90 v/v) was used; 4.5 equivalents were added in 2.5 min. For PS-oxidation, 0.2 M PADS in acetonitrile:2,6-lutidine (1:1) was used with 2-5 column volumes of thiolation reagent used. The Cap A solution was 20% 1-methylimidazole in acetonitrile. Cap B was acetic anhydride:2,6-lutidine:acetonitrile (25:30:45). For capping, 1.5 column volumes were added in 1.5 min.

Step 2. Deprotection Conditions

The CPG was mixed with 180 mL of aqueous methylamine (Aldrich) in a 250 mL Schott bottle. The mixture was placed in a shaker oven at 45° C. for 75 min. The mixture was cooled, filtered into a 1 L Schott bottle and the CPG was washed three times with 160 mL of DMSO. The filtrates were combined and cooled for 10 min in dry ice. TEA.3HF (Alfa Aesar, 270 mL) was added to the mixture. The bottle was placed in a shaker oven at 40° C. for 65 min. The mixture was cooled to room temperature and the reaction was quenched with 1 L of 50 mM sodium acetate.

Step 3. Purification of Oligonucleotides

The oligonucleotides were purified by reverse phase HPLC using a matrix of TSK-GEL, SuperQ-5PW (20) in a 5 cm×17-18 cm column. The temperature was maintained at 55° C. to 65° C. The buffers were 20 mM sodium phosphate, 10% ACN v/v, pH 8.5 (buffer A) and 20 mM sodium phosphate, 1 M NaBr, 10% ACN, pH 8.5 (buffer B). The flow rates was 60 mL/min. The gradient was from 20% B to 40% B in 160 min.

The solution of crude oligonucleotide was diluted 5-fold with buffer A and loaded directly onto the purification column using a flow rate that loaded about 20 mg crude material (based on $A_{260}$ readings) per mL of column volume. Fractions of 50 mL were collected.

INCORPORATION BY REFERENCE

All of the patents and publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A method of removing a silyl protecting group from an oligonucleotide, comprising the step of admixing, under aqueous conditions, an oligonucleotide bearing a silyl protecting group with
    at least one solvent selected from the group consisting of DMSO, DMF, ethanol, isopropanol, methanol, acetonitrile, and combinations thereof, and
    a deprotecting reagent selected from the group consisting of pyridine-HF, DMAP-HF (dimethylaminopyridine-HF), urea-HF, TSAF (tris(dimethylamino)sulfonium difluorotrimethylsilane), DAST (diethylamino sulfur trifluoride), polyvinyl pyridine-HF and an amine-HF reagent of formula AA:

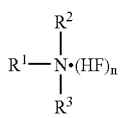

AA wherein $R^1$ is alkyl, aryl, heteroaryl, aralkyl or heteroaralkyl;
$R^2$ is alkyl, aryl, heteroaryl, aralkyl or heteroaralkyl;
$R^3$ is aryl or heteroaryl; and
n is 1 to 20.

2. The method of claim 1, wherein said oligonucleotide comprises at least one ribonucleotide.

3. The method of claim 1, wherein the reaction is carried out in the presence of microwave radiation.

4. The method of claim 1, wherein the reaction is carried out at an elevated temperature.

5. The method of claim 4, wherein reaction is carried out at about 40° C., 45° C., 55° C., 60° C. or 65° C.

6. The method of claim 1, wherein desilylation is carried out for about 1 hour at about 40° C.

7. The method of claim 1, wherein about 3-4.5 mg of polyvinyl pyridine-HF are added for each 10 µL of the solvent.

8. The method of claim 7, wherein, for each mg of polyvinyl pyridine-HF, about 5 µL of DMSO are added to the reaction mixture.

9. The method of claim 7, wherein DMSO and DBU are added to the reaction mixture.

10. The method of claim 9, wherein, for each mg of polyvinyl pyridine-HF, about 5 µL of DMSO and about 2.5 µL of DBU are added to the reaction mixture.

11. The method of claim 1, wherein about 0.07-0.12 g of polyvinyl pyridine-HF are added for each mL of solvent.

12. The method of claim 11, wherein DBU is added to the reaction mixture.

13. The method of claim 12, wherein about 0.08 mL of DBU for each mL of solvent is added to the reaction mixture.

14. The method of claim 1, wherein said oligonucleotide consists of ribonucleotides and deoxyribonucleotides.

15. The method of claim 1, wherein said oligonucleotide consists of ribonucleotides and 2'-O-Methyl-ribonucleotides.

16. The method of claim 1, wherein said oligonucleotide comprises at least one modified nucleobase.

17. The method of claim 1, wherein said oligonucleotide comprises at least one backbone modification selected from phosphorothioate, phosphorodithioate, alkylphosphonate, and phosphoamidate.

18. The method of claim 1, wherein said oligonucleotide comprises at least one 2'-fluoro nucleotide.

19. The method of claim 1, wherein the reaction is carried out for at least about 15 minutes.

20. A method of removing a silyl protecting group from an oligonucleotide, comprising the step of admixing, under aqueous conditions, an oligonucleotide bearing a silyl protecting group with pyridine-HF, wherein pyridine-HF is premixed with DMSO and a base selected from the group consisting of DBU, Hunig's base, pyridine, piperidine and N-methylimidazole.

21. The method of claim 20, wherein the ratio of pyridine-HF/base/DMSO is about 1/5/5, 1/4/5, 1/4/4, 1/3.5/4 or 1/3.5/3.5.

22. The method of claim 21, wherein the base is DBU.

23. A method of removing a silyl protecting group from an oligonucleotide, comprising the step of admixing, under aqueous conditions, an oligonucleotide bearing a silyl protecting group with
   a co-solvent mixture comprising (a) at least one water-miscible solvent, and (b) MeNH2 or ammonia, and
   a deprotecting reagent selected from the group consisting of pyridine-HF, DMAP-HF (dimethvlaminopyridine-HF), urea-HF, TSAF (tris(dimethylamino)sulfonium difluorotrimethylsilane), DAST (diethvlaminosulfur trifluoride), polyvinyl pyridine-HF and an amine-HF reagent of formula AA:

AA wherein
$R^1$ is alkyl, aryl, heteroaryl, aralkyl or heteroaralkyl;
$R^2$ is alkyl, aryl, heteroaryl, aralkyl or heteroaralkyl;
$R^3$ is aryl or heteroaryl; and
n is 1 to 20.

24. The method of claim 23, wherein four volumes of a pyridine-HF/base/DMSO mixture are added for each volume of the co-solvent mixture.

25. The method of claim 23, wherein about 0.08 mL of pyridine-HF and about 0.33 mL of DMSO are added for each mL of the co-solvent mixture.

26. The method of claim 23, wherein about 0.175 mL of DBU, about 0.25 mL of DMSO and about 0.075 mL of pyridine-HF are added for each mL of the co-solvent mixture.

27. The method of claim 23, wherein about 0.01-0.08 mL of pyridine-HF are added for each mL of the co-solvent mixture.

28. The method of claim 27, wherein DBU is added to the reaction mixture.

29. The method of claim 27, wherein about 0.25 mL of DMSO are added for each mL of the co-solvent mixture.

30. The method of claim 29, wherein the ratio of pyridine-HF to DMSO is about 3 parts pyridine-HF to 10 parts DMSO.

31. The method of claim 23, wherein said oligonucleotide comprises at least one ribonucleotide.

32. The method of claim 23, wherein the reaction is carried out in the presence of microwave radiation.

33. The method of claim 23, wherein the reaction is carried out at an elevated temperature.

34. The method of claim 33, wherein reaction is carried out at about 40° C., 45° C., 55° C., 60° C. or 65° C.

35. The method of claim 23, wherein said oligonucleotide consists of ribonucleotides and deoxyribonucleotides.

36. The method of claim 23, wherein said oligonucleotide consists of ribonucleotides and 2'-O-Methyl-ribonucleotides.

37. The method of claim 23, wherein said oligonucleotide comprises at least one modified nucleobase.

38. The method of claim 23, wherein said oligonucleotide comprises at least one backbone modification selected from phosphorothioate, phosphorodithioate, alkylphosphonate, and phosphoamidate.

39. The method of claim 23, wherein said oligonucleotide comprises at least one 2'-fluoro nucleotide.

* * * * *

SEQUENCE LISTING

```
<160> NUMBER OF SEQ ID NOS: 59

<210> SEQ ID NO 1
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: misc_feature
<222> LOCATION: (2)..(3)
<223> OTHER INFORMATION: Phosphorothioate linkage
<220> FEATURE:
<221> NAME/KEY: misc_feature
<222> LOCATION: (18)..(19)
<223> OTHER INFORMATION: Phosphorothioate linkage
<220> FEATURE:
<221> NAME/KEY: misc_feature
<222> LOCATION: (19)..(20)
<223> OTHER INFORMATION: Phosphorothioate linkage
<220> FEATURE:
<221> NAME/KEY: misc_feature
<222> LOCATION: (20)..(21)
<223> OTHER INFORMATION: Phosphorothioate linkage

<400> SEQUENCE: 1
gcggaucaaa ccucaccaat t                                              21

<210> SEQ ID NO 2
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: misc_feature
<222> LOCATION: (2)..(3)
<223> OTHER INFORMATION: Phosphorothioate linkage
<220> FEATURE:
```

```
<221> NAME/KEY: misc_feature
<222> LOCATION: (18)..(19)
<223> OTHER INFORMATION: Phosphorothioate linkage
<220> FEATURE:
<221> NAME/KEY: misc_feature
<222> LOCATION: (19)..(20)
<223> OTHER INFORMATION: Phosphorothioate linkage
<220> FEATURE:
<221> NAME/KEY: misc_feature
<222> LOCATION: (20)..(21)
<223> OTHER INFORMATION: Phosphorothioate linkage

<400> SEQUENCE: 2
uuggugaggu uugauccgct t                                              21

<210> SEQ ID NO 3
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 3
gcggaucaaa ccucaccaat t                                              21

<210> SEQ ID NO 4
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 4
uuggugaggu uugauccgct t                                              21

<210> SEQ ID NO 5
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 5
gcggaacaau ccugaccaat t                                              21

<210> SEQ ID NO 6
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 6
uuggucagga uuguuccgct t                                              21
```

```
<210> SEQ ID NO 7
<211> LENGTH: 10
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 7
caucgctgat                                                              10

<210> SEQ ID NO 8
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 8
cuuacgcuga guacuucgat t                                                 21

<210> SEQ ID NO 9
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 9
ucgaaguacu cagcguaagt t                                                 21

<210> SEQ ID NO 10
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 10
gcggaucaaa ccucaccaat t                                                 21

<210> SEQ ID NO 11
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 11
gcggaucaaa ccucaccaat t                                                 21
```

```
<210> SEQ ID NO 12
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 12
gcggaucaaa ccucaccaat t                                              21

<210> SEQ ID NO 13
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 13
uuggugaggu uugauccgct t                                              21

<210> SEQ ID NO 14
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 14
uuggugaggu uugauccgct t                                              21

<210> SEQ ID NO 15
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 15
uuggugaggu uugauccgct t                                              21

<210> SEQ ID NO 16
<211> LENGTH: 10
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 16
acgucgauat                                                           10
```

```
<210> SEQ ID NO 17
<211> LENGTH: 12
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 17
cgucaaggcg at                                                              12

<210> SEQ ID NO 18
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (20)..(21)
<223> OTHER INFORMATION: Phosphorothioate linkage

<400> SEQUENCE: 18
cuuacgcuga guacuucgat t                                                    21

<210> SEQ ID NO 19
<211> LENGTH: 22
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(2)
<223> OTHER INFORMATION: Phosphorothioate linkage

<400> SEQUENCE: 19
cuuacgcuga guacuucgat tt                                                   22

<210> SEQ ID NO 20
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
gucaucacac ugaauaccaa u                                                    21

<210> SEQ ID NO 21
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
```

```
<223> OTHER INFORMATION: 2'-fluoro modified sugar
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: modified_base
<222> LOCATION: (7)
<223> OTHER INFORMATION: 2'-fluoro modified sugar
<220> FEATURE:
<221> NAME/KEY: modified_base
<222> LOCATION: (11)
<223> OTHER INFORMATION: 2'-fluoro modified sugar
<220> FEATURE:
<221> NAME/KEY: modified_base
<222> LOCATION: (13)
<223> OTHER INFORMATION: 2'-fluoro modified sugar
<220> FEATURE:
<221> NAME/KEY: modified_base
<222> LOCATION: (18)
<223> OTHER INFORMATION: 2'-fluoro modified sugar
<220> FEATURE:
<221> NAME/KEY: modified_base
<222> LOCATION: (21)..(22)
<223> OTHER INFORMATION: 2'-fluoro modified sugar
<220> FEATURE:
<221> NAME/KEY: misc_feature
<222> LOCATION: (21)..(22)
<223> OTHER INFORMATION: Phosphorothioate linkage
<220> FEATURE:
<221> NAME/KEY: misc_feature
<222> LOCATION: (22)..(23)
<223> OTHER INFORMATION: Phosphorothioate linkage

<400> SEQUENCE: 21
uuggaucaaa uauaagauuc ccu                                              23

<210> SEQ ID NO 22
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: 2'-fluoro modified sugar
<220> FEATURE:
<221> NAME/KEY: modified_base
<222> LOCATION: (7)..(10)
<223> OTHER INFORMATION: 2'-fluoro modified sugar
<220> FEATURE:
<221> NAME/KEY: modified_base
<222> LOCATION: (14)..(17)
<223> OTHER INFORMATION: 2'-fluoro modified sugar
<220> FEATURE:
<221> NAME/KEY: modified_base
<222> LOCATION: (19)
<223> OTHER INFORMATION: 2'-fluoro modified sugar
<220> FEATURE:
<221> NAME/KEY: misc_feature
<222> LOCATION: (20)..(21)
<223> OTHER INFORMATION: Phosphorothioate linkage

<400> SEQUENCE: 22
ggacuacucu aaguucuact t                                                21

<210> SEQ ID NO 23
<211> LENGTH: 21
<212> TYPE: DNA
<213> ORGANISM: Artificial Sequence
<220> FEATURE:
```

-continued

```
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)
<223> OTHER INFORMATION: 2'-fluoro modified sugar
<220> FEATURE:
<221> NAME/KEY: modified_base
<222> LOCATION: (7)..(9)
<223> OTHER INFORMATION: 2'-fluoro modified sugar
<220> FEATURE:
<221> NAME/KEY: modified_base
<222> LOCATION: (14)
<223> OTHER INFORMATION: 2'-fluoro modified sugar
<220> FEATURE:
<221> NAME/KEY: modified_base
<222> LOCATION: (17)..(19)
<223> OTHER INFORMATION: 2'-fluoro modified sugar
<220> FEATURE:
<221> NAME/KEY: misc_feature
<222> LOCATION: (20)..(21)
<223> OTHER INFORMATION: Phosphorothioate linkage

<400> SEQUENCE: 23
guagaacuua gaguagucct t                                              21

<210> SEQ ID NO 24
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: 2'-fluoro modified sugar
<220> FEATURE:
<221> NAME/KEY: modified_base
<222> LOCATION: (7)..(10)
<223> OTHER INFORMATION: 2'-fluoro modified sugar
<220> FEATURE:
<221> NAME/KEY: modified_base
<222> LOCATION: (14)..(17)
<223> OTHER INFORMATION: 2'-fluoro modified sugar
<220> FEATURE:
<221> NAME/KEY: modified_base
<222> LOCATION: (19)
<223> OTHER INFORMATION: 2'-fluoro modified sugar
<220> FEATURE:
<221> NAME/KEY: misc_feature
<222> LOCATION: (20)..(21)
<223> OTHER INFORMATION: Phosphorothioate linkage

<400> SEQUENCE: 24
ggaucaucuc aagucuuact t                                              21

<210> SEQ ID NO 25
<211> LENGTH: 22
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)
```

-continued

```
<223> OTHER INFORMATION: 2'-fluoro modified sugar
<220> FEATURE:
<221> NAME/KEY: modified_base
<222> LOCATION: (7)..(9)
<223> OTHER INFORMATION: 2'-fluoro modified sugar
<220> FEATURE:
<221> NAME/KEY: modified_base
<222> LOCATION: (14)
<223> OTHER INFORMATION: 2'-fluoro modified sugar
<220> FEATURE:
<221> NAME/KEY: modified_base
<222> LOCATION: (17)..(18)
<223> OTHER INFORMATION: 2'-fluoro modified sugar
<220> FEATURE:
<221> NAME/KEY: misc_feature
<222> LOCATION: (21)..(22)
<223> OTHER INFORMATION: Phosphorothioate linkage

<400> SEQUENCE: 25
guaagacuug agaugauccc tt                                              22

<210> SEQ ID NO 26
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: modified_base
<222> LOCATION: (5)
<223> OTHER INFORMATION: 2'-fluoro modified sugar
<220> FEATURE:
<221> NAME/KEY: modified_base
<222> LOCATION: (9)
<223> OTHER INFORMATION: 2'-fluoro modified sugar
<220> FEATURE:
<221> NAME/KEY: misc_feature
<222> LOCATION: (20)..(21)
<223> OTHER INFORMATION: Phosphorothioate linkage

<400> SEQUENCE: 26
cgucugucug ucccggauct t                                               21

<210> SEQ ID NO 27
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: modified_base
<222> LOCATION: (10)
<223> OTHER INFORMATION: 2'-fluoro modified sugar
<220> FEATURE:
<221> NAME/KEY: modified_base
<222> LOCATION: (14)
<223> OTHER INFORMATION: 2'-fluoro modified sugar
<220> FEATURE:
<221> NAME/KEY: misc_feature
<222> LOCATION: (20)..(21)
```

```
<223> OTHER INFORMATION: Phosphorothioate linkage

<400> SEQUENCE: 27
gauccgggac agacagacgt t                                              21

<210> SEQ ID NO 28
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: 2'-fluoro modified sugar
<220> FEATURE:
<221> NAME/KEY: modified_base
<222> LOCATION: (7)..(10)
<223> OTHER INFORMATION: 2'-fluoro modified sugar
<220> FEATURE:
<221> NAME/KEY: modified_base
<222> LOCATION: (14)..(17)
<223> OTHER INFORMATION: 2'-fluoro modified sugar
<220> FEATURE:
<221> NAME/KEY: modified_base
<222> LOCATION: (19)
<223> OTHER INFORMATION: 2'-fluoro modified sugar
<220> FEATURE:
<221> NAME/KEY: misc_feature
<222> LOCATION: (20)..(21)
<223> OTHER INFORMATION: Phosphorothioate linkage

<400> SEQUENCE: 28
ggaucaucuc aagucuuact t                                              21

<210> SEQ ID NO 29
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: 2'-fluoro modified sugar
<220> FEATURE:
<221> NAME/KEY: modified_base
<222> LOCATION: (7)..(10)
<223> OTHER INFORMATION: 2'-fluoro modified sugar
<220> FEATURE:
<221> NAME/KEY: modified_base
<222> LOCATION: (14)..(17)
<223> OTHER INFORMATION: 2'-fluoro modified sugar
<220> FEATURE:
<221> NAME/KEY: modified_base
<222> LOCATION: (19)
<223> OTHER INFORMATION: 2'-fluoro modified sugar
<220> FEATURE:
<221> NAME/KEY: misc_feature
<222> LOCATION: (20)..(21)
<223> OTHER INFORMATION: Phosphorothioate linkage

<400> SEQUENCE: 29
ggacuacucu aaguucuact t                                              21

<210> SEQ ID NO 30
```

```
<211> LENGTH: 21
<212> TYPE: RNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: modified_base
<222> LOCATION: (7)..(8)
<223> OTHER INFORMATION: 2'-fluoro modified sugar
<220> FEATURE:
<221> NAME/KEY: modified_base
<222> LOCATION: (10)
<223> OTHER INFORMATION: 2'-fluoro modified sugar
<220> FEATURE:
<221> NAME/KEY: modified_base
<222> LOCATION: (12)..(14)
<223> OTHER INFORMATION: 2'-fluoro modified sugar
<220> FEATURE:
<221> NAME/KEY: modified_base
<222> LOCATION: (19)
<223> OTHER INFORMATION: 2'-fluoro modified sugar

<400> SEQUENCE: 30
ggaaucuuau auuugaucca a                                          21

<210> SEQ ID NO 31
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: modified_base
<222> LOCATION: (5)
<223> OTHER INFORMATION: 2'-fluoro modified sugar
<220> FEATURE:
<221> NAME/KEY: modified_base
<222> LOCATION: (9)
<223> OTHER INFORMATION: 2'-fluoro modified sugar
<220> FEATURE:
<221> NAME/KEY: misc_feature
<222> LOCATION: (20)..(21)
<223> OTHER INFORMATION: Phosphorothioate linkage

<400> SEQUENCE: 31
cgucugucug ucccggauct t                                          21

<210> SEQ ID NO 32
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)
<223> OTHER INFORMATION: 2'-O-methyl sugar
<220> FEATURE:
<221> NAME/KEY: modified_base
<222> LOCATION: (16)
<223> OTHER INFORMATION: 2'-O-methyl sugar
<220> FEATURE:
```

```
<221> NAME/KEY: modified_base
<222> LOCATION: (19)
<223> OTHER INFORMATION: 2'-O-methyl sugar
<220> FEATURE:
<221> NAME/KEY: modified_base
<222> LOCATION: (21)..(22)
<223> OTHER INFORMATION: 2'-O-methyl sugar
<220> FEATURE:
<221> NAME/KEY: misc_feature
<222> LOCATION: (21)..(22)
<223> OTHER INFORMATION: Phosphorothioate linkage
<220> FEATURE:
<221> NAME/KEY: misc_feature
<222> LOCATION: (22)..(23)
<223> OTHER INFORMATION: Phosphorothioate linkage

<400> SEQUENCE: 32
cguccuugaa gaagauggug cgc                                              23

<210> SEQ ID NO 33
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(22)
<223> OTHER INFORMATION: 2'-O-methyl sugar
<220> FEATURE:
<221> NAME/KEY: misc_feature
<222> LOCATION: (21)..(22)
<223> OTHER INFORMATION: Phosphorothioate linkage
<220> FEATURE:
<221> NAME/KEY: misc_feature
<222> LOCATION: (22)..(23)
<223> OTHER INFORMATION: Phosphorothioate linkage

<400> SEQUENCE: 33
auugguauuc agugugauga cac                                              23

<210> SEQ ID NO 34
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: 2'-O-methyl sugar
<220> FEATURE:
<221> NAME/KEY: modified_base
<222> LOCATION: (7)
<223> OTHER INFORMATION: 2'-O-methyl sugar
<220> FEATURE:
<221> NAME/KEY: modified_base
<222> LOCATION: (11)
<223> OTHER INFORMATION: 2'-O-methyl sugar
<220> FEATURE:
<221> NAME/KEY: modified_base
<222> LOCATION: (13)
<223> OTHER INFORMATION: 2'-O-methyl sugar
<220> FEATURE:
<221> NAME/KEY: modified_base
<222> LOCATION: (18)
<223> OTHER INFORMATION: 2'-O-methyl sugar
<220> FEATURE:
<221> NAME/KEY: modified_base
<222> LOCATION: (21)..(22)
<223> OTHER INFORMATION: 2'-O-methyl sugar
<220> FEATURE:
<221> NAME/KEY: misc_feature
<222> LOCATION: (21)..(22)
```

```
<223> OTHER INFORMATION: Phosphorothioate linkage
<220> FEATURE:
<221> NAME/KEY: misc_feature
<222> LOCATION: (22)..(23)
<223> OTHER INFORMATION: Phosphorothioate linkage

<400> SEQUENCE: 34
uuggaucaaa uauaagauuc ccu                                              23

<210> SEQ ID NO 35
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: modified_base
<222> LOCATION: (2)
<223> OTHER INFORMATION: 2'-O-methyl sugar
<220> FEATURE:
<221> NAME/KEY: modified_base
<222> LOCATION: (16)..(18)
<223> OTHER INFORMATION: 2'-O-methyl sugar
<220> FEATURE:
<221> NAME/KEY: misc_feature
<222> LOCATION: (20)..(21)
<223> OTHER INFORMATION: Phosphorothioate linkage

<400> SEQUENCE: 35
cuaugagccu gaagccuaat t                                                21

<210> SEQ ID NO 36
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: 2'-O-methyl sugar
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: modified_base
<222> LOCATION: (17)
<223> OTHER INFORMATION: 2'-O-methyl sugar
<220> FEATURE:
<221> NAME/KEY: misc_feature
<222> LOCATION: (20)..(21)
<223> OTHER INFORMATION: Phosphorothioate linkage

<400> SEQUENCE: 36
uuaggcuuca ggcucauagt t                                                21

<210> SEQ ID NO 37
<211> LENGTH: 21
<212> TYPE: DNA
<213> ORGANISM: Artificial Sequence
<220> FEATURE:
```

-continued

```
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: modified_base
<222> LOCATION: (2)
<223> OTHER INFORMATION: 2'-O-methyl sugar
<220> FEATURE:
<221> NAME/KEY: modified_base
<222> LOCATION: (16)..(18)
<223> OTHER INFORMATION: 2'-O-methyl sugar
<220> FEATURE:
<221> NAME/KEY: misc_feature
<222> LOCATION: (20)..(21)
<223> OTHER INFORMATION: Phosphorothioate linkage

<400> SEQUENCE: 37
cuacgaaccu gaagccuaat t                                             21

<210> SEQ ID NO 38
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: 2'-O-methyl sugar
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: modified_base
<222> LOCATION: (17)
<223> OTHER INFORMATION: 2'-O-methyl sugar
<220> FEATURE:
<221> NAME/KEY: misc_feature
<222> LOCATION: (20)..(21)
<223> OTHER INFORMATION: Phosphorothioate linkage

<400> SEQUENCE: 38
uuaggcuuca gguucguagt t                                             21

<210> SEQ ID NO 39
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: modified_base
<222> LOCATION: (2)
<223> OTHER INFORMATION: 2'-O-methyl sugar
<220> FEATURE:
<221> NAME/KEY: modified_base
<222> LOCATION: (16)..(18)
```

```
<223> OTHER INFORMATION: 2'-O-methyl sugar
<220> FEATURE:
<221> NAME/KEY: misc_feature
<222> LOCATION: (20)..(21)
<223> OTHER INFORMATION: Phosphorothioate linkage

<400> SEQUENCE: 39
cuacgaaccu gaagccuaat t                                              21

<210> SEQ ID NO 40
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: modified_base
<222> LOCATION: (2)
<223> OTHER INFORMATION: 2'-O-methyl sugar
<220> FEATURE:
<221> NAME/KEY: modified_base
<222> LOCATION: (16)..(18)
<223> OTHER INFORMATION: 2'-O-methyl sugar
<220> FEATURE:
<221> NAME/KEY: misc_feature
<222> LOCATION: (20)..(21)
<223> OTHER INFORMATION: Phosphorothioate linkage

<400> SEQUENCE: 40
cuaugagccu gaagccuaat t                                              21

<210> SEQ ID NO 41
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: modified_base
<222> LOCATION: (6)
<223> OTHER INFORMATION: 2'-O-methyl sugar
<220> FEATURE:
<221> NAME/KEY: modified_base
<222> LOCATION: (14)
<223> OTHER INFORMATION: 2'-O-methyl sugar
<220> FEATURE:
<221> NAME/KEY: modified_base
<222> LOCATION: (18)
<223> OTHER INFORMATION: 2'-O-methyl sugar
<220> FEATURE:
<221> NAME/KEY: misc_feature
<222> LOCATION: (20)..(21)
<223> OTHER INFORMATION: Phosphorothioate linkage

<400> SEQUENCE: 41
agaagcagga ccuuaucuat t                                              21

<210> SEQ ID NO 42
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: 2'-O-methyl sugar
<220> FEATURE:
<221> NAME/KEY: modified_base
<222> LOCATION: (10)
<223> OTHER INFORMATION: 2'-O-methyl sugar
<220> FEATURE:
<221> NAME/KEY: modified_base
<222> LOCATION: (12)..(14)
<223> OTHER INFORMATION: 2'-O-methyl sugar
<220> FEATURE:
<221> NAME/KEY: modified_base
<222> LOCATION: (19)
<223> OTHER INFORMATION: 2'-O-methyl sugar

<400> SEQUENCE: 42
ggaaucuuau auuugaucca a                                              21

<210> SEQ ID NO 43
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)
<223> OTHER INFORMATION: 2'-O-methyl sugar
<220> FEATURE:
<221> NAME/KEY: modified_base
<222> LOCATION: (5)
<223> OTHER INFORMATION: 2'-O-methyl sugar
<220> FEATURE:
<221> NAME/KEY: modified_base
<222> LOCATION: (14)
<223> OTHER INFORMATION: 2'-O-methyl sugar

<400> SEQUENCE: 43
gcaccaucuu cuucaaggac g                                              21

<210> SEQ ID NO 44
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(23)
<223> OTHER INFORMATION: 2'-O-methyl sugar
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: misc_feature
<222> LOCATION: (2)..(3)
<223> OTHER INFORMATION: Phosphorothioate linkage
<220> FEATURE:
<221> NAME/KEY: misc_feature
<222> LOCATION: (3)..(4)
<223> OTHER INFORMATION: Phosphorothioate linkage
<220> FEATURE:
<221> NAME/KEY: misc_feature
<222> LOCATION: (4)..(5)
<223> OTHER INFORMATION: Phosphorothioate linkage
```

```
<220> FEATURE:
<221> NAME/KEY: misc_feature
<222> LOCATION: (5)..(6)
<223> OTHER INFORMATION: Phosphorothioate linkage
<220> FEATURE:
<221> NAME/KEY: misc_feature
<222> LOCATION: (6)..(7)
<223> OTHER INFORMATION: Phosphorothioate linkage
<220> FEATURE:
<221> NAME/KEY: misc_feature
<222> LOCATION: (7)..(8)
<223> OTHER INFORMATION: Phosphorothioate linkage
<220> FEATURE:
<221> NAME/KEY: misc_feature
<222> LOCATION: (8)..(9)
<223> OTHER INFORMATION: Phosphorothioate linkage
<220> FEATURE:
<221> NAME/KEY: misc_feature
<222> LOCATION: (9)..(10)
<223> OTHER INFORMATION: Phosphorothioate linkage
<220> FEATURE:
<221> NAME/KEY: misc_feature
<222> LOCATION: (10)..(11)
<223> OTHER INFORMATION: Phosphorothioate linkage
<220> FEATURE:
<221> NAME/KEY: misc_feature
<222> LOCATION: (11)..(12)
<223> OTHER INFORMATION: Phosphorothioate linkage
<220> FEATURE:
<221> NAME/KEY: misc_feature
<222> LOCATION: (12)..(13)
<223> OTHER INFORMATION: Phosphorothioate linkage
<220> FEATURE:
<221> NAME/KEY: misc_feature
<222> LOCATION: (13)..(14)
<223> OTHER INFORMATION: Phosphorothioate linkage
<220> FEATURE:
<221> NAME/KEY: misc_feature
<222> LOCATION: (14)..(15)
<223> OTHER INFORMATION: Phosphorothioate linkage
<220> FEATURE:
<221> NAME/KEY: misc_feature
<222> LOCATION: (15)..(16)
<223> OTHER INFORMATION: Phosphorothioate linkage
<220> FEATURE:
<221> NAME/KEY: misc_feature
<222> LOCATION: (16)..(17)
<223> OTHER INFORMATION: Phosphorothioate linkage
<220> FEATURE:
<221> NAME/KEY: misc_feature
<222> LOCATION: (17)..(18)
<223> OTHER INFORMATION: Phosphorothioate linkage
<220> FEATURE:
<221> NAME/KEY: misc_feature
<222> LOCATION: (18)..(19)
<223> OTHER INFORMATION: Phosphorothioate linkage
<220> FEATURE:
<221> NAME/KEY: misc_feature
<222> LOCATION: (19)..(20)
<223> OTHER INFORMATION: Phosphorothioate linkage
<220> FEATURE:
<221> NAME/KEY: misc_feature
<222> LOCATION: (20)..(21)
<223> OTHER INFORMATION: Phosphorothioate linkage
<220> FEATURE:
<221> NAME/KEY: misc_feature
<222> LOCATION: (21)..(22)
<223> OTHER INFORMATION: Phosphorothioate linkage
<220> FEATURE:
<221> NAME/KEY: misc_feature
<222> LOCATION: (22)..(23)
<223> OTHER INFORMATION: Phosphorothioate linkage

<400> SEQUENCE: 44
acaaacacca uugucacacu cca                                         23

<210> SEQ ID NO 45
<211> LENGTH: 23
```

```
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(23)
<223> OTHER INFORMATION: 2'-O-methyl sugar
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: misc_feature
<222> LOCATION: (2)..(3)
<223> OTHER INFORMATION: Phosphorothioate linkage
<220> FEATURE:
<221> NAME/KEY: misc_feature
<222> LOCATION: (20)..(21)
<223> OTHER INFORMATION: Phosphorothioate linkage
<220> FEATURE:
<221> NAME/KEY: misc_feature
<222> LOCATION: (21)..(22)
<223> OTHER INFORMATION: Phosphorothioate linkage
<220> FEATURE:
<221> NAME/KEY: misc_feature
<222> LOCATION: (22)..(23)
<223> OTHER INFORMATION: Phosphorothioate linkage

<400> SEQUENCE: 45
acaaacacca uugucacacu cca                                             23

<210> SEQ ID NO 46
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(23)
<223> OTHER INFORMATION: 2'-O-methyl sugar
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: misc_feature
<222> LOCATION: (2)..(3)
<223> OTHER INFORMATION: Phosphorothioate linkage
<220> FEATURE:
<221> NAME/KEY: misc_feature
<222> LOCATION: (3)..(4)
<223> OTHER INFORMATION: Phosphorothioate linkage
<220> FEATURE:
<221> NAME/KEY: misc_feature
<222> LOCATION: (4)..(5)
<223> OTHER INFORMATION: Phosphorothioate linkage
<220> FEATURE:
<221> NAME/KEY: misc_feature
<222> LOCATION: (5)..(6)
<223> OTHER INFORMATION: Phosphorothioate linkage
<220> FEATURE:
<221> NAME/KEY: misc_feature
<222> LOCATION: (6)..(7)
<223> OTHER INFORMATION: Phosphorothioate linkage
<220> FEATURE:
<221> NAME/KEY: misc_feature
<222> LOCATION: (7)..(8)
<223> OTHER INFORMATION: Phosphorothioate linkage
<220> FEATURE:
<221> NAME/KEY: misc_feature
<222> LOCATION: (8)..(9)
<223> OTHER INFORMATION: Phosphorothioate linkage
<220> FEATURE:
<221> NAME/KEY: misc_feature
```

```
<222> LOCATION: (9)..(10)
<223> OTHER INFORMATION: Phosphorothioate linkage
<220> FEATURE:
<221> NAME/KEY: misc_feature
<222> LOCATION: (10)..(11)
<223> OTHER INFORMATION: Phosphorothioate linkage
<220> FEATURE:
<221> NAME/KEY: misc_feature
<222> LOCATION: (11)..(12)
<223> OTHER INFORMATION: Phosphorothioate linkage
<220> FEATURE:
<221> NAME/KEY: misc_feature
<222> LOCATION: (12)..(13)
<223> OTHER INFORMATION: Phosphorothioate linkage
<220> FEATURE:
<221> NAME/KEY: misc_feature
<222> LOCATION: (13)..(14)
<223> OTHER INFORMATION: Phosphorothioate linkage
<220> FEATURE:
<221> NAME/KEY: misc_feature
<222> LOCATION: (14)..(15)
<223> OTHER INFORMATION: Phosphorothioate linkage
<220> FEATURE:
<221> NAME/KEY: misc_feature
<222> LOCATION: (15)..(16)
<223> OTHER INFORMATION: Phosphorothioate linkage
<220> FEATURE:
<221> NAME/KEY: misc_feature
<222> LOCATION: (16)..(17)
<223> OTHER INFORMATION: Phosphorothioate linkage
<220> FEATURE:
<221> NAME/KEY: misc_feature
<222> LOCATION: (17)..(18)
<223> OTHER INFORMATION: Phosphorothioate linkage
<220> FEATURE:
<221> NAME/KEY: misc_feature
<222> LOCATION: (18)..(19)
<223> OTHER INFORMATION: Phosphorothioate linkage
<220> FEATURE:
<221> NAME/KEY: misc_feature
<222> LOCATION: (19)..(20)
<223> OTHER INFORMATION: Phosphorothioate linkage
<220> FEATURE:
<221> NAME/KEY: misc_feature
<222> LOCATION: (20)..(21)
<223> OTHER INFORMATION: Phosphorothioate linkage
<220> FEATURE:
<221> NAME/KEY: misc_feature
<222> LOCATION: (21)..(22)
<223> OTHER INFORMATION: Phosphorothioate linkage
<220> FEATURE:
<221> NAME/KEY: misc_feature
<222> LOCATION: (22)..(23)
<223> OTHER INFORMATION: Phosphorothioate linkage

<400> SEQUENCE: 46
acacacaaca cugucacauu cca                                            23

<210> SEQ ID NO 47
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: 2'-O-methyl sugar
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: misc_feature
<222> LOCATION: (2)..(3)
<223> OTHER INFORMATION: Phosphorothioate linkage
<220> FEATURE:
```

```
<221> NAME/KEY: misc_feature
<222> LOCATION: (19)..(20)
<223> OTHER INFORMATION: Phosphorothioate linkage
<220> FEATURE:
<221> NAME/KEY: misc_feature
<222> LOCATION: (20)..(21)
<223> OTHER INFORMATION: Phosphorothioate linkage
<220> FEATURE:
<221> NAME/KEY: misc_feature
<222> LOCATION: (21)..(22)
<223> OTHER INFORMATION: Phosphorothioate linkage

<400> SEQUENCE: 47
acaacaacac ugucacauuc ca                                              22

<210> SEQ ID NO 48
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 48
ggcucuuagc aaagucaagt t                                               21

<210> SEQ ID NO 49
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 49
ggcucuuagc aaagucaagt t                                               21

<210> SEQ ID NO 50
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 50
cuugacuuug cuaagagcct t                                               21

<210> SEQ ID NO 51
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 51
cuugacuuug cuaagagcct t                                               21
```

```
<210> SEQ ID NO 52
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: 2'-O-methyl sugar
<220> FEATURE:
<221> NAME/KEY: modified_base
<222> LOCATION: (10)
<223> OTHER INFORMATION: 2'-O-methyl sugar
<220> FEATURE:
<221> NAME/KEY: modified_base
<222> LOCATION: (12)..(14)
<223> OTHER INFORMATION: 2'-O-methyl sugar
<220> FEATURE:
<221> NAME/KEY: modified_base
<222> LOCATION: (19)
<223> OTHER INFORMATION: 2'-O-methyl sugar

<400> SEQUENCE: 52
ggaaucuuau auuugaucca t                                            21

<210> SEQ ID NO 53
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: 2'-O-methyl sugar
<220> FEATURE:
<221> NAME/KEY: modified_base
<222> LOCATION: (10)
<223> OTHER INFORMATION: 2'-O-methyl sugar
<220> FEATURE:
<221> NAME/KEY: modified_base
<222> LOCATION: (12)..(14)
<223> OTHER INFORMATION: 2'-O-methyl sugar
<220> FEATURE:
<221> NAME/KEY: modified_base
<222> LOCATION: (19)
<223> OTHER INFORMATION: 2'-O-methyl sugar

<400> SEQUENCE: 53
ggaaucuuau auuugaucca t                                            21

<210> SEQ ID NO 54
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(2)
<223> OTHER INFORMATION: Phosphorothioate linkage
<220> FEATURE:
```

```
<221> NAME/KEY: misc_feature
<222> LOCATION: (20)..(21)
<223> OTHER INFORMATION: Phosphorothioate linkage

<400> SEQUENCE: 54
ggaaucuuau auuugaucca t                                              21

<210> SEQ ID NO 55
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: misc_feature
<222> LOCATION: (20)..(21)
<223> OTHER INFORMATION: Phosphorothioate linkage

<400> SEQUENCE: 55
ggaaucuuau auuugaucca t                                              21

<210> SEQ ID NO 56
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: 2'-O-methyl sugar
<220> FEATURE:
<221> NAME/KEY: modified_base
<222> LOCATION: (10)
<223> OTHER INFORMATION: 2'-O-methyl sugar
<220> FEATURE:
<221> NAME/KEY: modified_base
<222> LOCATION: (12)..(14)
<223> OTHER INFORMATION: 2'-O-methyl sugar
<220> FEATURE:
<221> NAME/KEY: modified_base
<222> LOCATION: (19)..(20)
<223> OTHER INFORMATION: 2'-O-methyl sugar

<400> SEQUENCE: 56
ggaaucuuau auuugaucca a                                              21

<210> SEQ ID NO 57
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: 2'-O-methyl sugar
<220> FEATURE:
<221> NAME/KEY: modified_base
<222> LOCATION: (7)
<223> OTHER INFORMATION: 2'-O-methyl sugar
<220> FEATURE:
<221> NAME/KEY: modified_base
<222> LOCATION: (11)
```

```
<223> OTHER INFORMATION: 2'-O-methyl sugar
<220> FEATURE:
<221> NAME/KEY: modified_base
<222> LOCATION: (13)
<223> OTHER INFORMATION: 2'-O-methyl sugar
<220> FEATURE:
<221> NAME/KEY: modified_base
<222> LOCATION: (18)
<223> OTHER INFORMATION: 2'-O-methyl sugar
<220> FEATURE:
<221> NAME/KEY: modified_base
<222> LOCATION: (21)..(22)
<223> OTHER INFORMATION: 2'-O-methyl sugar
<220> FEATURE:
<221> NAME/KEY: misc_feature
<222> LOCATION: (21)..(22)
<223> OTHER INFORMATION: Phosphorothioate linkage
<220> FEATURE:
<221> NAME/KEY: misc_feature
<222> LOCATION: (22)..(23)
<223> OTHER INFORMATION: Phosphorothioate linkage

<400> SEQUENCE: 57
uuggaucaaa uauaagauuc ccu                                          23

<210> SEQ ID NO 58
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 58
aaagugcaca acauuauact t                                            21

<210> SEQ ID NO 59
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 59
guauaauguu gugcacuuut t                                            21
```